US008865868B2

(12) United States Patent
Behrens et al.

(10) Patent No.: US 8,865,868 B2
(45) Date of Patent: Oct. 21, 2014

(54) CONJUGATED PROTEINS WITH PROLONGED IN VIVO EFFICACY

(75) Inventors: Carsten Behrens, København N (DK); Patrick William Garibay, Holte (DK); Søren Østergaard, Brønshøj (DK); Henrik Sune Andersen, Lyngby (DK); Nils Langeland Johansen, København Ø (DK); Bernd Peschke, Måløv (DK); Sonja Bak, København NV (DK)

(73) Assignee: Novo Nordisk Healthcare AG, Zurich (CH)

( * ) Notice: Subject to any disclaimer, the term of this patent is extended or adjusted under 35 U.S.C. 154(b) by 351 days.

(21) Appl. No.: 13/055,871

(22) PCT Filed: Aug. 6, 2009

(86) PCT No.: PCT/EP2009/060186
§ 371 (c)(1),
(2), (4) Date: May 26, 2011

(87) PCT Pub. No.: WO2010/015668
PCT Pub. Date: Feb. 11, 2010

(65) Prior Publication Data
US 2011/0223151 A1 Sep. 15, 2011

Related U.S. Application Data

(60) Provisional application No. 61/088,157, filed on Aug. 12, 2008.

(30) Foreign Application Priority Data
Aug. 6, 2008 (EP) ..................................... 08161905

(51) Int. Cl.
| C07K 1/113 | (2006.01) |
| C07K 14/745 | (2006.01) |
| A61K 47/48 | (2006.01) |
| A61K 38/36 | (2006.01) |

(52) U.S. Cl.
CPC ..... *A61K 47/48023* (2013.01); *A61K 47/48246* (2013.01)
USPC .......... 530/381; 514/14.3; 530/382; 530/383; 530/384

(58) Field of Classification Search
None
See application file for complete search history.

(56) References Cited

U.S. PATENT DOCUMENTS

| 4,683,202 A | 7/1987 | Mullis |
| 5,156,956 A | 10/1992 | Motoki et al. |
| 5,252,469 A | 10/1993 | Andou et al. |
| 5,438,040 A | 8/1995 | Ekwuribe |
| 5,545,618 A | 8/1996 | Buckley et al. |
| 5,646,272 A | 7/1997 | Kramer et al. |
| 5,731,183 A | 3/1998 | Kobayashi et al. |
| 5,736,356 A | 4/1998 | Sano et al. |
| 5,834,250 A | 11/1998 | Wells et al. |
| 5,849,535 A | 12/1998 | Cunningham et al. |
| 5,891,840 A | 4/1999 | Cady et al. |
| 5,951,972 A | 9/1999 | Daley et al. |
| 6,004,931 A | 12/1999 | Cunningham et al. |
| 6,057,292 A | 5/2000 | Cunningham et al. |
| 6,136,536 A | 10/2000 | Tomkinson et al. |
| 6,143,523 A | 11/2000 | Cunningham et al. |
| 6,268,343 B1 | 7/2001 | Knudsen et al. |
| 6,358,705 B1 | 3/2002 | Kjeldsen et al. |
| 6,528,486 B1 | 3/2003 | Larsen et al. |
| 6,608,183 B1 | 8/2003 | Cox, III |
| 7,153,930 B1 | 12/2006 | Morrison et al. |
| 2001/0011071 A1 | 8/2001 | Knudsen et al. |
| 2002/0115590 A1* | 8/2002 | Johannessen et al. ............ 514/2 |
| 2002/0142964 A1 | 10/2002 | Nissen et al. |
| 2003/0162949 A1 | 8/2003 | Cox |
| 2003/0165996 A1 | 9/2003 | Halkier et al. |
| 2004/0001827 A1 | 1/2004 | Dennis |
| 2004/0053370 A1 | 3/2004 | Glaesner et al. |
| 2005/0260237 A1 | 11/2005 | Byun et al. |
| 2006/0094655 A1 | 5/2006 | Guyon et al. |
| 2006/0183197 A1 | 8/2006 | Andersen et al. |
| 2007/0203058 A1 | 8/2007 | Lau et al. |
| 2007/0244202 A1 | 10/2007 | Murase |
| 2008/0095837 A1 | 4/2008 | Dinh et al. |
| 2009/0156478 A1 | 6/2009 | Lau et al. |
| 2011/0306551 A1* | 12/2011 | Zundel et al. ................ 514/14.1 |

FOREIGN PATENT DOCUMENTS

| EA | 008438 | 6/2007 |
| EP | 243929 A2 | 11/1987 |
| EP | 534568 A2 | 3/1993 |
| EP | 555649 A2 | 8/1993 |

(Continued)

OTHER PUBLICATIONS

Kim et al., 2003, "Development and Characterization of a Glucagon-Like Peptide 1-Albumin Conjugate," Diabetes 52:751-759.
Makino et al., 2005, "Semisynthesis of Human Ghrelin: Condensation of a Boc-Protected Recombinant Peptide With a Synthetic O-Acylated Fragment," Biopolymers 79(5):238-247.
Okada, 2001, "Synthesis of Peptides by Solution Methods," Current Organic Chemistry 5(1):1-43.
Ostrovsky, 1975, "Comparative Characteristics of The Hydrophobic Nature of Certain Proteins by Their Interaction with 2-P Toluidino," Ukrayins'kyi Biokhimichnyi Zhurnal 47(6):701-707.

(Continued)

*Primary Examiner* — Jeffrey E Russel
(74) *Attorney, Agent, or Firm* — Jianjie Hu

(57) ABSTRACT

The invention relates to conjugated proteins, in particular but not exclusively, blood coagulation factors, to processes for preparing the conjugated proteins which contain the steps of reacting a protein or glycoprotein, such as factor VIIa or human growth hormone, with a water insoluble albumin binder in the presence of an optionally substituted cyclodextrin molecule, to pharmaceutical compositions comprising the protein conjugates and to the use of the protein conjugates in therapy, in particular but not exclusively, for the treatment of diseases alleviated by blood coagulation factors such as the prophylactic treatment of hemophilia.

9 Claims, No Drawings

(56) References Cited

FOREIGN PATENT DOCUMENTS

| | | |
|---|---:|---|
| EP | 785276 A1 | 7/1997 |
| EP | 950665 A1 | 10/1999 |
| EP | 1329458 A2 | 7/2003 |
| EP | 05102171.5 | 3/2005 |
| EP | 1704165 A1 | 9/2006 |
| JP | 2000-500505 A | 1/2000 |
| JP | 2002-504527 A | 2/2002 |
| JP | 2002-508162 A | 3/2002 |
| JP | 2003-505347 | 2/2003 |
| JP | 2003-199569 A | 7/2003 |
| JP | 2004-528014 A | 9/2004 |
| JP | 2004-535442 A | 11/2004 |
| JP | 2006273834 A | 10/2006 |
| JP | 2010-116407 A | 5/2010 |
| RU | 2006107600 A | 10/2007 |
| WO | 90/04788 A1 | 5/1990 |
| WO | 90/11296 | 10/1990 |
| WO | 91/11457 A1 | 8/1991 |
| WO | 92/05271 A1 | 4/1992 |
| WO | 92/09690 A2 | 6/1992 |
| WO | 94/10200 A1 | 5/1994 |
| WO | 96/06931 A1 | 3/1996 |
| WO | 96/12505 A1 | 5/1996 |
| WO | 96/22366 A1 | 7/1996 |
| WO | 96/29342 | 9/1996 |
| WO | 97/11178 A1 | 3/1997 |
| WO | 98/08871 | 3/1998 |
| WO | 98/08872 A1 | 3/1998 |
| WO | 98/38285 A2 | 9/1998 |
| WO | 99/43341 | 9/1999 |
| WO | 99/43361 A1 | 9/1999 |
| WO | 99/43705 A1 | 9/1999 |
| WO | 99/43708 | 9/1999 |
| WO | 9943707 | 9/1999 |
| WO | 00/34331 | 6/2000 |
| WO | 00/69911 | 11/2000 |
| WO | 01/04156 | 1/2001 |
| WO | 01/09163 A2 | 2/2001 |
| WO | WO 01/12155 | 2/2001 |
| WO | 0151071 | 7/2001 |
| WO | WO 01/58935 | 8/2001 |
| WO | 0258725 | 1/2002 |
| WO | 02/46227 A2 | 6/2002 |
| WO | 02/055532 | 7/2002 |
| WO | 02/055532 A2 | 7/2002 |
| WO | 02/087597 A1 | 11/2002 |
| WO | 02098446 A1 | 12/2002 |
| WO | 03/002136 | 1/2003 |
| WO | 03/013573 A1 | 2/2003 |
| WO | 03/040309 A2 | 5/2003 |
| WO | 03/044056 A2 | 5/2003 |
| WO | 03/087139 A2 | 10/2003 |
| WO | WO 03/093465 | 11/2003 |
| WO | 2004/022593 A2 | 3/2004 |
| WO | 2004/064788 A2 | 8/2004 |
| WO | 2004/065621 A1 | 8/2004 |
| WO | 2004/074315 A2 | 9/2004 |
| WO | 2004/099246 A2 | 11/2004 |
| WO | 2005/014049 A2 | 2/2005 |
| WO | WO 2005/014035 | 2/2005 |
| WO | 2005/027978 | 3/2005 |
| WO | 2005/028516 A2 | 3/2005 |
| WO | WO 2005/027978 | 3/2005 |
| WO | 2005/035553 A2 | 4/2005 |
| WO | 2005/058958 A2 | 6/2005 |
| WO | 2005/070468 A2 | 8/2005 |
| WO | 2006/005667 A2 | 1/2006 |
| WO | WO 2006/013202 | 2/2006 |
| WO | 2006/037810 A2 | 4/2006 |
| WO | 2006/048777 A2 | 5/2006 |
| WO | 2006/097536 A2 | 9/2006 |
| WO | 2006/097537 | 9/2006 |
| WO | 2006/097537 A2 | 9/2006 |
| WO | 2006/097538 A1 | 9/2006 |
| WO | 2006/122982 A1 | 11/2006 |
| WO | 2006/134173 A2 | 12/2006 |
| WO | 2006/134174 A2 | 12/2006 |
| WO | 2007/020290 A1 | 2/2007 |
| WO | 2007/093594 A1 | 8/2007 |
| WO | 2008/014430 A1 | 1/2008 |
| WO | WO 2008/003750 | 1/2008 |
| WO | 2008/020075 A1 | 2/2008 |
| WO | 2008/027854 A2 | 3/2008 |
| WO | 2008/101240 A1 | 8/2008 |
| WO | WO 2009/030771 | 3/2009 |
| WO | 2010/015668 A1 | 2/2010 |
| WO | 2010/029159 A1 | 3/2010 |
| WO | 2010/084173 A1 | 7/2010 |
| WO | 2010/102886 A1 | 9/2010 |

OTHER PUBLICATIONS

Picó, 1990, "Use of 1-Anilino-8-Naphthalene Sulfonate as a Reporter Molecule to Study The Bile Salts-Bovine Serum Albumin Binding," Studia Biophysica 136(1):21-26, Abstract XP-008039734.

Rudinger, 1976, "Characteristics of the Amino Acids As Components of a Peptide Hormone Sequence," Peptides Hormones, JA Parsons Edition, University Park Press, Jun. 1976, pp. 1-7.

Schinzel et al., 1991, "The Phosphate Recognition Site of *Escherichia coli* Maltodextrin Phosphorylase," Federation of European Biochemical Society Jul. 1991, 286(1, 2):125-128.

Sheffield, 2001, "Modification of Clearance of Therapeutic and Potentially Therapeutic Proteins," Current Drug Targets Cardiovascular & Haematological Disorders 1(1):1-22.

Sigma Genosys (Web Site), Designing Custom Peptides, pp. 1-2, Accessed Dec. 16, 2004.

Voet et al., 1995, Biochemistry 2nd ed., John Wiley & Sons, Inc., pp. 235-241.

Wallace, 1995, "Peptide Ligation and Semisynthesis," Current Opinion in Biotechnology 6(4):403-410.

Zobel et al., 2003, "Phosphate Ester Serum Albumin Affinity Tags Greatly Improve Peptide Half-Life in Vivo," Bioorganic & Medicinal Chemistry Letters 13:1513-1515.

Knudsen, L.B. et al., "Potent Derivatives of Glucagon-Like Peptide-1 With Pharmacokinetic Properperties Suitable for Once Daily Administration", Journal of Medicinal Chemistry, 2000 vol. 43, pp. 1664-1669.

Deacon, C.F. et al., "Dipeptidyl peptidase IV resistant analogues of glucagon-like peptide-1 which have extended metabolic stability and improved biological activity." 1998, Diabetologia, vol. 41, pp. 271-278.

Kurtzhals, P, et al., "Albumin Binding of Insulins Acylated With Fatty Acids: Characterization of the Ligand-Protein Interaction and Correlation Between Binding Affinity and Timing of the Insulin Effect In Vivo," Biochem J, 1995, vol. 312, pp. 725-731.

Watanabe et al., "Structure-Activity Relationships of Glucagon-Like Peptide-1 (7-36) Amide: Insulinotropic Activities in Perfused Rat Pancreases, and Receptor Binding and Cyclic AMP Production in RINm5F Cells," Journal of Endocrinology, 1994, vol. 140, pp. 45-52.

Jung-Guk Kim et al. Diabetes Development and Characterization of a Glucagon-Like Peptide 1-Albumin Conjugate/ The Ability to Activate the Glucagon-Lile Peptide 1 Receptor In Vivo 2003 52-751-759.

Definition of Moiety, from http://dictionary.reference.com/browse/moiety, pp. 1-2. accessed Aug. 26, 2010.

Small Bowel Syndrome from e-Medicine, pp. 1-12, accessed Sep. 24, 2008.

Alam K S M et al, Journal of Biotechnology, "Expression and Purification of a Mutant Human Growth Hormone That is Resistant to Proteolytic Cleavage by Thrombin, Plasmin and Human Plasma In Vitro", 1998, vol. 65, No. 2-3, pp. 183-190.

Chantalet L et al, Protein and Peptide Letters, "The Crystal Structure of Wild-Type Growth Hormone at 2.5A Resolution", 1995, vol. 2, No. 2, pp. 333-340.

Carey et al, The Liver: Biology and Pathobiology 2nd Edition, Raven Press Ltd, "Enterohepatic Circulation", 1988, vol. 33, pp. 573-616.

Devos A. M. et al, Science, "Human Growth Hormone and Extracelleular Domain of its Receptor: Crystal Structure of the Complex", 1992, vol. 255, pp. 306-312.

(56) References Cited

OTHER PUBLICATIONS

Garcia-Barros,et al, Journal of Endocrinology, "Proteolytic Processing of Human Growth Hormone (GH)by Rat Tissues In Viitro: Influence of Sex and Age", 2000, vol. 23, pp. 748-754.

Lewis.U.J, Annual Review of Physiology, "Variants of Growth Hormone and Prolactin and Their Posttranslational Modifications", 1984, vol. 46, pp. 33-42.

Needeleman,et al Journal of Molecular Biology a General Method Applicable to the Search for Similarities in the Amino Acid Sequence of Two Proteins 1970 48-443-453.

Palmberger.et al European Journal of Pharmaceutics and Biopharmaceutics : Official Thiolated Polymers: Evaluation of the Influenece of the Amount of Covalently Attached L-Cysteine to Poly(Acrylic Acid) 2007 66-405-412.

Partlow.K.C.et al Biomaterials Exploiting Lipid Raft Transport With Membrane Targeted Nanoparticles:A Strategy for Cytosolic Drug Delivery 2008 29-3367-3375.

Petersen,et al Protein Engineering Amino Acid Neighbours and Detailed Conformational Analysis of Cysteines in Proteins 1999 12 7 535-548.

S.Y.Chae,et al Bioconjugate Chemistry Preparation, Characterization and Application of Biotinylated and Biotin-Pegylated Glucagon-Like Peptide-1 Analogues for Enhanced Oral Delivery 2008 19-334-341.

Said, Hamid M; Mohammed, Zainab M. Current Opinion in Gastroenterology Intestinal Absorption of Watersoluble Vitamins: An Update 2006 22 2 140-146.

Saiki,et al Science Primer-Directed Enzymatic Amplification of DNA With a Thermostable DND Polymerase 1988 239 4839 487-491.

Takatsuka.et al European Journal of Pharmaceutics and Biopharmaceutics : Official Enhancement of Intestinal Absorption of Poorly Absorbed Hydrophilic Compounds by Simultaneous Use of Mucolytic Agent and Non-Ionic Surfacant 2006 62-52-58.

Von Heijne.G Academic Press Sequence Analysis of Molecular Biology.Treasure Torve or Trivial Pursuit 1987-188.

Zhiwen Zhang et al, Science, A New Strategy for the Synthesis of Glycoproteins, 2004 vol. 303, pp. 371-373.

Filikov et al, "Computational Stabilization of Human Growth Hormone," Protein Science, 2002, vol. 11, No. 6, pp. 1452-1461.

Kasimova, MR et al., "NMR Studies of the Bacbone Flixibility and Structure of Human Growth Hormone: A Comparison of High and Low pH Conformations," Journal of Molecular Biology, 2002, vol. 318, pp. 679-695.

Dennis, MS et al., Journal of Biological Chemistry, "Albumin Binding as a General Strategy for Improving the Pharmacokinetics of Proteins", 2002, vol. 277, No. 28 pp. 35035-35043.

Pasut, G et al., Expert Opinion on Therapeutic Patents, "Protein, Peptide and Non-Peptide Drug Pegylation . . . " 2004, vol. 14, No. 6, pp. 859-894.

Bebernitz et al., Journal of Medicinal Chemistry, "Reduction in Glucose Levels in STZ Diabetic Rats by 4-(2,2-Dimethyl-1-Oxopropyl) Benzoic Acid: A Prodrug Approach for Targeting the Liver" 2001 vol. 44 pp. 512-523.

Beljaars et al., Journal of Drug Targeting, "Neoglyco-and Neopeptide Albumins for Cell-Specific Delivery of Drugs to Chronically Diseased Livers" 2001 vol. 115 pp. 189-240.

Biessen et al., Journal of Medicinal Chemistry, "Synthesis of Cluster Galactosides With High Affinity for the Hepatic Asialoglycoprotein Receptor" 1995 vol. 38 Part 9 pp. 1538-1546.

Hatori et al., Journal of the Controlled Release, "Controlled Biodistribution of Galactosylated Liposomes and Incorporated Probucol in Hepatocyte-Selective Drug Targeting" 2000 vol. 69 pp. 369-377.

Kim et al., Journal of Drug Targeting, "Evaluation of the Bile Acid Transporter in Enhancing Intestinal Permeability to Renininhibitory Peptides" 1993 vol. 1 pp. 347-359.

Kramer et al., Journal of Biological Chemistry, "Liver-Specific Drug Targeting by Coupling to Bile Acids", 1992 vol. 267 Part 26 pp. 18598-18604.

Kramer et al., Journal of the Controlled Release, "Modified Bile Acids as Carriers for Peptides and Drugs", 1997 vol. 46 Part 1-2 pp. 17-30.

Kramer et al., Journal of Biological Chemistry, "Intestinal Absorption of Peptides by Coupling to Bile Acids" 1994 vol. 269 Part 14 pp. 10621-10627.

Kullack-Ublick et al., Gastroenterology, "Chlorambucil-Taurocholate is Transported by Bile Acid Carriers Expressed in Human Hepatocellular Carcinomas" 1997, vol. 113 pp. 1295-1305.

Leeson et al., Journal of Medicinal Chemistry, "Selective Thyromimetics. Cardiac-Sparing Thyroid Hormone Analogues Containing 3'-Arylmet Hyl Substituents" 1989 vol. 32 Part 2 pp. 320-326.

Nezasa et al., Drug Metabolism and Disposition, "Liver-Specific Distribution of Rosuvastatin in Rats: Comparison With Pravastatin and Simvastatin" 2002 vol. 30 Part 11 pp. 1158-1163.

Pecher et al., Biophysical Chemistry, "The Effect of Additional Disulfide Bonds on the Stability and Folding of Ribonuclease" 2009 vol. 141 Part 1 pp. 21-28.

Starke et al., Bioorganic & Medicinal Chemistry Letters, "Bile Acid-Oldigodeoxynucleotide Conjugates: Synthesis and Liver Excretion in Rats", 2001 vol. 11 pp. 945-949.

Swaan, PW et al., Bioconjugate Chemistry, "Enhanced Transepithelial Transport of Peptides by" 1997 vol. 8 Part 4 pp. 520-525.

Wess et al., Tetrahedron Letters, "Modified Bile Acids: Preparation of 7A, 12A-Dihydroxy-3a-AND 7A, L2A-Dihydroxy-3A-(2-Hydroxyethoxy)-SIJ-Cholanic Acid and Their Biological Activity" 1992, vol. 33 Part 2 pp. 195-198.

Inflammatory Bowel Disease from e-Medicine, pp. 1.24, Accessed Sep. 24, 2008.

Ngo JT et al., "Computational Complexity, Protein Structure Prediction, and the Levinthal Paradox," The Protein Folding Problem and Tertiary Structure Prediction, K. Mere Jr. and S. LeGrand Edition, 1994, pp. 433-495.

Residue definition from www.dictionary.com, pp. 1-6, Accessed May 5, 2009.

Green, Brian D. et al Biological Chemistry. Degradation, Receptor Binding, Insulin . . . 2004 385 2 169-177.

Greenwald Journal of the Controlled Release PEG Drugs: An Overview 2001 74-159-171.

Ji, J. et al. Biomaterials Stearyl Poly (Ethylene Oxide) Grafted Surfaces for Preferential Adsorption of Albumin. 2001 22-3015-3023.

Knudsen, L.B. Journal of Medicinal Chemistry Glucagon-Like Peptide-1 . . . 2004 47-4128-4134.

Simonovsky et al. Journal of Biomaterials Science, Polymer Edition Poly(Ether Urethane)s Incorporating Long Alkyl Side-Chains With Terminal Carboxyl Groups as Fatty Acid Mimics: Synthesis, Structural Characterization and Protein Adsorption 2005 16 12 1463-1483.

Soltero and Ekwurlbe Innovations in Pharmaceutical Technology the Oral Delivery of Protein and Peptide Drugs. 2001 1-106-110.

Still, J. Gordon, Diabetes/Metabolism Research Reviews, Development of Oral Insulin: Progress and Current Status, 2002, vol. 18, Suppl 1, pp. S29-S37.

Veronese F. M Biomaterials Peptide and Protein Pegylation: A Review of Porblems and Solutions 2001 22 5 405-417.

English abstract of JP 2004535442, (Nov. 25, 2004).

English abstract of RU 2006107600, (Oct. 27, 2007).

English abstract of JP 2010116407, (May 27, 2010).

English abstract of JP 2004528014, (Sep. 16, 2004).

Berendsen, 1998, "A Glimpse of the Holy Grail?" Science 282:642-643.

Bradley et al., 2002, "Limits of Cooperativity in a Structually Modular Protein: Response of the Notch Ankyrin Domain to Analogous Alanine Substitutions in Each Repeat," Journal of Molecular Biology 324:373-386.

Chuang et al., 2002, "Pharmaceutical Strategies Utilizing Recombinant Human Serum Albumin," Pharmaceutical Research 19(5):569-577.

Han, 2002, "Targeted Prodrug Design to Optimize Drug Delivery," AAPS Pharmsci 2(1):1-11.

Hodgson et al., 2004, "The Synthesis of Peptides and Proteins Containing Non-Natural Amino Acids," Chemical Reviews 33(7):422-430.

(56) References Cited

OTHER PUBLICATIONS

Holz et al., 2003, "Glucagon-Like Peptide-1 Synthetic Analogs: New Therapeutic Agents for Use in the Treatment of Diabetes Mellitus," Current Medicinal Chemistry 10(22):2471-2483.
Frostell-Karlsson et al., Journal of Medicinal Chemistry, "Albumin Binding Property", 2000, vol. 43, No. 10, pp. 1986-1992.
Berge et al., Journal of Pharmaceutical Sciences, "Pharmaceutical Salts", 1977, vol. 66, No. 1, pp. 1-19.
Masters, "Applications of Spray Drying," in Spray-Drying Handbook (5.sup.th ed; Longman Scientific and Technical), pp. 491-676 (1991).
Altschul et al, -, "Blast Manual" downloaded Jan. 10, 2013.
Altschul et al., Journal of Molecular Biology "BLASTP, BLASTN, and FASTA", 1990, vol. 215, Number-, pp. 403-410.
B. Lee and F.M. Richards, Journal of Molecular Biology, "The Interpretation of Protein Structures: Estimation of Static Accessibility", 1971, vol. 55, Number -, pp. 379-400.
B. Peschke et al., Bioorganic & Medicinal Chemistry, "C-Terminally Pegylated HGH Derivatives", 2007, vol. 15, Number-, pp. 4382-4395.
Broadhead et al., Drug Delivery, "The Spray Drying of Pharmaceuticals", 1992, vol. 18, No. 11 & 12, pp. 1169-1206.
C. A. Lipinski et al., Advanced Drug Delivery Reviews, "Experimental and Computational Approaches to Estimate Solubility and Permeability in Drug Discovery and Development Settings", 1997, vol. 23, pp. 3-25.
Carpenter and Crowe, Cryobiology, "Modes of Stabilization of a Protein by Organic Solutes During Dessication", 1988, vol. 25, Number-, pp. 459-470.
Dayhoff et al., -, "Atlas of Protein Sequence and Structure", 1978, vol. 5, No. 3, Pages-.
G. T. Hermanson, -, "Bioconjugate Techniques, Elsevier", 2008, vol. 2, Number-, Pages-.
I. Moriguchi, S. Hirono, I. Nakagome, H. Hirano, Chemical & Pharmaceutical Bulletin, "Comparison of Reliability of LOGP Values for Drugs Calculated by Several Methods", 1994, vol. 42, Number-, pp. 976-978.
Kurtzhals, P et al., Biochemical Journal, "Albumin Binding of Insulins Acylated With Fatty Acides . . . ", 1995, vol. 312, Number-, pp. 725-731.
Kaempfer, Journal of General Microbiology, "Genus Streptomyces", 1991, vol. 137, Number-, pp. 1831-1892.
M. M. Kurfurst, Analytical Biochemistry, "-", 1992, vol. 200(2), Number-, pp. 244-248.
Mumenthaler et al. Pharmaceutical Research, "Feasibility Study on Spray-Drying Protein Pharmaceuticals: Recombinant Human Growth Hormone and Tissue-Type Plasminogen Activator", 1994, vol. 11, No. 1, pp. 41263.
Chene, N., "Growth hormones. II. Structure-function relationships," Reprod. Nutr. Dev., 1989. , 29 1-25.
Roser, Biopharmaceutical, "Trehalsoe Drying: A Novel Replacement for Freeze Drying", 1991, vol. 4, Number-, pp. 47-53.
Sato, H, Advanced Drug Delivery Reviews, "Enzymatic Procedure for Site-Specific Pegylation of Proteins", 2002, vol. 54, Number-, pp. 487-504.
T. Fujita; J. Iwasa and C. Hansch, Journal of the American Chemical Society, "A New Substituent Constant, PI, Derived From Partition Coefficients", 1964, vol. 86, Number-, pp. 5175-5180.
Wada, E et al., Biotechnology Letters, "Enzymatic Modification of . . . ", 2001, vol. 23, Number-, pp. 1367-1372.
Williams and Polli, Journal of Parenteral Science & Technology, "The Lyophilization of Pharmaceuticals: A Literature Review", 1984, vol. 38, No. 2, pp. 48-59.
Gregory J. Russel-Jones and David H. Alpers, Membrane Transporters as Drug Targets, 1999, Chapter 17, New York.
Alexander Deitrs,et al, Journal of the American Chemical Society, "Adding Amino Acids With Novel Reactivity to the Genetic Code of *Saccharomyces cerevisiae*", 2003, vol. 125, 39, pp. 11782-11783.

Altschul SF, Madden TL, Schäffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402.
Beaucage&CaruthersTetrahedron Lettersdeoxynucleoside Phosphoramidites—A New Class of Key Intermediates for Deoxypolynucleotide Synthesis 1859-1862, 1981, vol. 22, No. 20.
Cabrita,et al, Biotechnology Annual ReviewProtein Expression and Refolding—A Practical Guide to Getting the Most Out of Inclusion Bodies, 2004, vol. 10, pp. 31-50.
Carillo,et al, Journal of Applied Mathametics "The Multiple Sequence Alignment Problem in Biology" 1988 vol. 48 Part 5 pp. 1073-1082.
Chalasani et al, Journal of the Controlled Releasea Novel Vitamin B12-Nanosphere Conjugate Carrier System for Peroral Delivery of Insulin, 2007, vol. 117, pp. 421-429.
Chin et al, Science, An Expanded Eukaryotic Genetic Code, 2003, vol. 301,pp. 964-967.
De Vos, A.M.et al Science Human Growth Hormone and Extracellular Domain OD its Receptor Crystal Structure of the Complex 1992 255 5042 306-312.
Devereux et alNucleic Acids Researcha Comprehensive Set of Sequence Analysis Programs for the VAX, 1984, vol. 12, No. 1, pp. 387-395.
Dombkowski A, Bioinformatics, Disulfide by Design:A Computational Method for the Rational Design of Disulfide Bonds in Proteins, 2003, vol. 19, No. 14, pp. 1852-1853.
Greene, et al Protective Groups in Organic Chemistry Synthesis Protective Groups in Organic Synthesis 2006 9-0-471.
M. Gribskov, J. Devereux, Sequence Analysis Primer, Stockton Press, NewYork and Macmillan, Basingstroke (1991), pp. 90-157.
Griffin,et al Humana Press, Totowa New Jersey "Methods in Molecular Biology vol. 24: Computer Analysis of Sequence Data Part I" 1994.
Gumbleton.M, Advanced Drug Delivery Reviews, Caveolae as Potential Macromolecule Trafficking Compartments Within Alveolar Epithelium, 2001, vol. 49, No. 3, pp. 281-300.
H. Li & Z. M. Qian, Medicinal Research Reviews. Transferrin/ Transferrin Receptor-Mediated Drug Delivery, 2002, vol. 22, No. 3, pp. 225-250.
Henikoff,et al Proceedings of the National Academy of Sciences of the USA Amino Acid Substitution Matrices Form Protein Blocks 1992 89-10915-10919.
Kondoh.et al, Molecular Pharmacology, A Novel Strategy for the Enhancement of Drug Absorption Using a Claudin Modulator, 2005 vol. 67, No. 3, pp. 749-756.
Lee et al, Biotechnology and Applied Biochemistry, Expression and Characterization of Human Growth Hormone-FC Fusion Proteins for Transcytosis Induction, 2007, vol. 46, pp. 211-217.
Lei Wang,et al, Science, Expanding the Genetic Code of *Escherichia coli*, 2001, vol. 292, pp. 498-500.
Leitner.V.M.et al European Journal of Pharmaceutics and Biopharmaceutics : Official Thiolated Ploymers: Evidence for the Formation of Disulphide Bonds With Mucus Glycoproteins 2003 56-207-214.
Lesk.A.M Oxford University Press Computational Molecular Biology: Sources and Methods for Sequence Analysis 1988-254.
Leuben.H.L.et al International Journal of Pharmaceutics Mucoadhesive Polymers in Personal Peptide Drug Delivery.V.Effect of Poly(Acrylates)on the Enzymatic of Peptide Drugs by Intestinal Brush Border Membrane Vesicles 1996, vol. 141, Nos. 1-2, pp. 39-52.
Liang & Young, Biochemical and Biophysical Research Communications, Insulin-Cell Penetrating Peptide Hybrids With Improved Intestinal Absorption Efficiency, 2005, vol. 335, pp. 734-738.
Lueben.H.L.et al Pharmaceutical Research Mucoadhesive Polymers in Peroral Peptide Drug Delivery .VI.Carbomer and Chitosan Improve the Intestinal Absorption of the Peptide Drug Buserelin In Vivo, 1996, vol. 13, No. 11, pp. 1668-1672.
Masuda.N,et al Biochimica et Biophysica Acta Molecular Cloning of CDNA Encoding 2O KDA Variant Human Growth Hormone and the Alternative Splicing Mechanism 1988 949 1 125-131.

(56) References Cited

OTHER PUBLICATIONS

Matthes, et al EMBO Journal Simultaneous Rapid Chemical Synthesis of Over 100 Oligonucleotides on a Microscale 1984 3 4 801-805.

Szente et al., "Solubilization of Fatty Acids and Similar Lipids by Methylated Cyclodextrins," Proceedings of the International Symposium on Cyclodextrins, Jan. 1, 1992, pp. 340-344.

Szejtil, Jozsef, Cyclodextrin Technology (A book), Published by Springer, 1998, p. 271.

Szente et al., "Fatty Acid-Cyclodextrin Complexes: Properties and Applications", Journal of Inclusion Phenomena and Molecular Recognition in Chemistry, 1993, vol. 16, pp. 339-354.

* cited by examiner

CONJUGATED PROTEINS WITH PROLONGED IN VIVO EFFICACY

CROSS REFERENCE TO RELATED APPLICATIONS

This application is a 35 U.S.C. §371 national stage application of International Patent Application PCT/EP2009/060186 (published as WO 2010/015668), filed Aug. 6, 2009, which claimed priority of European Patent Application 08161905.8, filed Aug. 6, 2008; this application further claims priority under 35 U.S.C. §119 of U.S. Provisional Application 61/088,157, filed Aug. 12, 2008.

FIELD OF THE INVENTION

The invention relates to conjugated proteins, in particular but not exclusively, blood coagulation factors, to processes for preparing said conjugates, to pharmaceutical compositions comprising said conjugates and to the use of the conjugates in therapy, in particular but not exclusively, for the treatment of diseases alleviated by blood coagulation factors such as the prophylactic treatment of hemophilia.

BACKGROUND OF THE INVENTION

Blood coagulation is a process consisting of a complex interaction of various blood components (or factors) that eventually gives rise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VII(a)).

For patients with severe hemophilia, there is a trend away from on-demand treatment towards prophylactic regimens to prevent bleeding and subsequent joint damage. However, with their short circulating half-life, coagulation factors such as FVIII, FIX and FVIIa in particular, are not ideal for long term prophylactic treatment, as both high doses and frequent injections are required for maintaining pharmacological relevant plasma levels. Current focus is therefore directed towards development of long acting analogues that are better suited for prophylactic use.

Pegylation is an established method for prolonging the circulating half-life of proteins. However, due to the large interaction interface of coagulation factors within the cell membrane, other coagulation factors and co factors there are limited possibilities for chemical modification without a detrimental loss of activity.

There is thus a great need for providing blood coagulation factors with increased plasma half-lives for the prophylactic treatment of hemophilia.

WO 2005/027978 (Novo Nordisk A/S) describes derivatives of glucagon-like-peptide-1 (GLP-1) which have a protracted profile of action wherein said polypeptides are linked to an albumin binding residue via a hydrophilic spacer.

The invention therefore provides novel protein conjugates with improved pharmacological properties as well as methods for their production.

SUMMARY OF THE INVENTION

According to a first aspect of the invention, there is provided a process for preparing a conjugated protein or glycoprotein which comprises the steps of reacting a protein or glycoprotein with a water insoluble albumin binder in the presence of an optionally substituted cyclodextrin molecule.

According to a second aspect of the invention there is provided a protein conjugate which comprises a protein or glycoprotein linked to an albumin binding residue via a hydrophilic spacer, or a pharmaceutically acceptable salt, solvate or prodrug thereof.

According to a further aspect of the invention there is provided a protein conjugate of the formula (I):

$$(A\text{—}W\text{—}B)_y\text{—}P \qquad (I)$$

wherein
P represents a protein or glycoprotein;
B represents a hydrophilic spacer;
W is a chemical group linking A and B;
A represents an albumin binding residue; and
y represents an integer selected from 1, 2, 3, 4, 5, 6, 7, 8, 9 or 10;
or a pharmaceutically acceptable salt, solvate or prodrug thereof.

According to a third aspect of the invention there is provided a process for preparing a conjugated blood coagulation factor which comprises the steps of reacting a blood coagulation factor as defined herein with a modifier group as defined herein.

According to a further aspect of the invention there is provided a conjugated blood coagulation factor comprising a blood coagulation factor as defined herein conjugated to a modifier group as defined herein.

According to a further aspect of the invention there is provided a method of treating hemophilia which comprises administering to a patient a therapeutically effective amount of a conjugated blood coagulation factor as defined herein.

DEFINITIONS

The term "protein", "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, y-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (a-aminoisobutyric acid), Abu (α-aminobutyric acid), Tle (tert-butylglycine), β-alanine, 3-aminomethyl benzoic acid and anthranilic acid. It will be appreciated that the term "conjugated" used herein with respect to a protein or glycoprotein refers to the specific conjugation with an albumin binding residue in accordance with the invention. It will also be appreciated that the protein or glycoprotein used in the conjugation process of the invention may already be conjugated with other moieties such as a sugar moiety.

The term "glycoprotein" as used herein refers to proteins that contain oligosaccharide chains (glycans) covalently attached to their polypeptide side-chains. It will be appreciated that when a glycoprotein is used in the conjugation process of the invention, the albumin binding residue may be linked to said glycoprotein via a glycan residue.

In the present context, the term "growth hormone compound" as used herein means growth hormone of mammalian origin, such as human, bovine, or porcine growth hormone, and recombinant growth hormone, such as recombinant human, bovine, or porcine growth hormone, and variants of such growth hormones. As used herein "GH" and "growth hormone compound" are interchangeable. When GH is a variant of growth hormone of mammalian origin, such as hGH and recombinant hGH, said variant is understood to be the compound obtained by substituting one or more amino acid residues in the growth hormone, e.g. hGH, sequence with another natural or unnatural amino acid; and/or by adding one or more natural or unnatural amino acids to the growth hormone, e.g. hGH, sequence; and/or by deleting one or more amino acid residue from the growth hormone, e.g. hGH, sequence, wherein any of these steps may optionally be followed by further derivatization of one or more amino acid residues. In particular, such substitutions are conservative in the sense that one amino acid residue is substituted by another amino acid residue from the same group, i.e. by another amino acid residue with similar properties. Amino acids may conveniently be divided in the following groups based on their properties: Basic amino acids (such as arginine, lysine, histidine), acidic amino acids (such as glutamic acid and aspartic acid), polar amino acids (such as glutamine, cysteine and asparagine), hydrophobic amino acids (such as leucine, isoleucine, proline, methionine and valine), aromatic amino acids (such as phenylalanine, tryptophan, tyrosine) and small amino acids (such as glycine, alanine, serine and threonine). Typically, the GH has at least 80% identity with hGH, and typically, has at least 20% of the growth hormone activity of hGH as determined in assay I herein.

In the present context, the term "albumin binding residue" as used herein means a residue which binds noncovalently to human serum albumin. The albumin binding residue attached to the protein or glycoprotein typically has a binding affinity towards human serum albumin that is below about 10 μM or even below about 1 μM. A range of albumin binding residues are known among linear and branched lipophillic moieties containing 12-40 carbon atoms, compounds with a cyclopentanophenanthrene skeleton, and/or peptides having 10-45 amino acid residues etc. Albumin binding properties can be measured by surface plasmon resonance as described in *J. Biol. Chem.* 277(38), 35035-35042, (2002).

The term "hydrophilic spacer" as used herein means a spacer that separates a protein or glycoprotein and an albumin binding residue with a chemical moiety which comprises at least 5 nonhydrogen atoms where 30-50% of these are either N or O.

The term "water insoluble" refers to a moiety having a cLogP>0.

The term "water soluble" refers to a moiety having a cLogP<0.

In the present context, the term "transamination" and related terms are intended to indicate a reaction wherein the amide nitrogen in the side chain of glutamine is exchanged with nitrogen from another compound, in particular nitrogen from another nitrogen containing nucleophile.

In the present context, the term "not accessible" is intended to indicate that something is absent or de facto absent in the sense that it cannot be reached. When it is stated that functional groups are not accessible in a protein to be conjugated it is intended to indicate that said functional group is absent from the protein or, if present, in some way prevented from taking part in reactions. By way of example, said functional group could be buried deep in the structure of the protein so that it is shielded from participating in the reaction. It is recognised that whether or not a functional group is accessible depends on the reaction conditions. It may be envisaged that, e.g. in the presence of denaturing agents or at elevated temperatures the protein may unfold to expose otherwise not accessible functional groups. It is to be understood that "not accessible" means "not accessible at the reaction condition chosen for the particular reaction of interest".

The term "alkane" or "alkyl" is intended to indicate a saturated, linear, branched and/or cyclic hydrocarbon. Unless specified with another number of carbon atoms, the term is intended to indicate hydrocarbons with from 1 to 30 (both included) carbon atoms, such as 1 to 20 (both included), such as from 1 to 10 (both included), e.g. from 1 to 5 (both included). The terms alkyl and alkylene refer to the corresponding radical and bi-radical, respectively.

The term "$C_{1-6}$ alkyl" refers to a straight chained or branched saturated hydrocarbon having from one to six carbon atoms inclusive. Examples of such groups include, but are not limited to, methyl, 2-propyl, 1-butyl, 2-butyl, 2-methyl-2-propyl, 2-methyl-1-butyl and n-hexyl.

The term "$C_{3-10}$ cycloalkyl" typically refers to cyclopropyl, cyclobutyl, cyclopentyl, cyclohexyl, cycloheptyl, cyclooctyl, cyclononyl, and cyclodecanyl.

The term "alkene" is intended to indicate linear, branched and/or cyclic hydrocarbons comprising at least one carbon-carbon double bond. Unless specified with another number of carbon atoms, the term is intended to indicate hydrocarbons with from 2 to 30 (both included) carbon atoms, such as 2 to 20 (both included), such as from 2 to 10 (both included), e.g. from 2 to 5 (both included). The terms alkenyl and alkenylene refer to the corresponding radical and bi-radical, respectively.

The term "alkyne" is intended to indicate linear, branched and/or cyclic hydrocarbons comprising at least one carbon-carbon triple bond, and it may optionally comprise one or more carbon-carbon double bonds. Unless specified with another number of carbon atoms, the term is intended to indicate hydrocarbons with from 2 to 30 (both included) carbon atoms, such as 2 to 20 (both included), such as from 2 to 10 (both included), e.g. from 2 to 5 (both included). The terms alkynyl and alkynylene refer to the corresponding radical and bi-radical, respectively.

The term "homocyclic aromatic compound" is intended to indicate aromatic hydrocarbons, such as benzene and naphthalene.

The term "heterocyclic compound" is intended to indicate a cyclic compound comprising 5, 6 or 7 ring atoms from which 1, 2, 3 or 4 are hetero atoms selected from N, O and/or S. Examples include heterocyclic aromatic compounds, such as thiophene, furan, pyran, pyrrole, imidazole, pyrazole, isothiazole, isooxazole, pyridine, pyrazine, pyrimidine, pyridazine, as well as their partly or fully hydrogenated equivalents, such as piperidine, pirazolidine, pyrrolidine, pyrroline, imidazolidine, imidazoline, piperazine and morpholine.

The terms "hetero alkane", "hetero alkene" and "hetero alkyne" are intended to indicate alkanes, alkenes and alkynes as defined above, in which one or more hetero atom or group have been inserted into the structure of said moieties. Examples of hetero groups and atoms include —O—, —S—, —S(O)—, —S(O)$_2$—, —C(O)—, —C(S)— and —N(R*)—, wherein R* represents hydrogen or $C_1$-$C_6$-alkyl. Examples of heteroalkanes include.

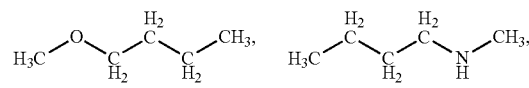

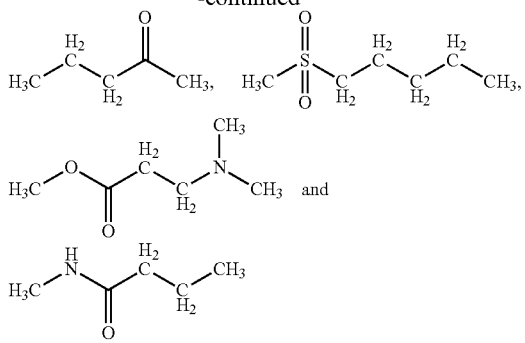

The term "radical" or "biradical" is intended to indicate a compound from which one or two, respectively, hydrogen atoms have been removed. When specifically stated, a radical may also indicate the moiety formed by the formal removal of a larger group of atoms, e.g. hydroxyl, from a compound.

The term "halogen" is intended to indicate members of the seventh main group of the periodic table, e.g. F, Cl, Br and I.

In the present context, the term "aryl" is intended to indicate a carbocyclic aromatic ring radical or a fused aromatic ring system radical wherein at least one of the rings are aromatic. Typical aryl groups include phenyl, biphenylyl, naphthyl, and the like.

The term "heteroaryl" or "hetaryl", as used herein, alone or in combination, refers to an aromatic ring radical with for instance 5 to 7 member atoms, or to a fused aromatic ring system radical with for instance from 7 to 18 member atoms, wherein at least one ring is aromatic, containing one or more heteroatoms as ring atoms selected from nitrogen, oxygen, or sulfur heteroatoms, wherein N-oxides and sulfur monoxides and sulfur dioxides are permissible heteroaromatic substitutions. Examples include furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like.

The asterisk marking as used in the chemical structures herein indicates the presence of an open bond suitable for attachment.

The term "conjugate" as a noun is intended to indicate a modified protein, i.e. a protein with a moiety bonded to it in order to modify the properties of said protein. As a verb, the term is intended to indicate the process of bonding a moiety to a protein to modify the properties of said protein.

As used herein, the term "prodrug" indicates biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

As used herein, the term "biohydrolyzable ester" is an ester of a drug substance (in casu, a compound according to the invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable ester is orally absorbed from the gut and is transformed to a compound according to the present invention in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in casu, a compound according to the present invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable amide is orally absorbed from the gut and is transformed to a compound according to the present invention in plasma. Many examples of such are known in the art and include by way of example lower alkyl amides, α-amino acid amides, alkoxyacyl amides, and alkylaminoalkylcarbonyl amides.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in *J. Pharm. Sci.* 66, 2, (1977) which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relieve the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal; in particular a human being, but it may also include animals, such as dogs, cats, cows, sheep and pigs.

The term "analogue" as used herein referring to a polypeptide means a modified peptide wherein one or more amino acid residues of the peptide have been substituted by other amino acid residues and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. All amino acids for which the optical isomer is not stated are to be understood to mean the L-isomer.

The term "functional in vivo half-life" is used in its normal meaning, i.e., the time at which 50% of the biological activity of the modified protein or a reference molecule is still present in the body/target organ, or the time it takes for the activity of the modified protein or reference molecule to drop to 50% of its peak value. As an alternative to determining functional in vivo half-life, "in vivo plasma half-life" may be determined, i.e., the time at which 50% of the modified proteins or reference molecules circulate in the plasma or bloodstream prior to being cleared. Determination of plasma half-life is often more simple than determining functional half-life and the magnitude of plasma half-life is usually a good indication of the magnitude of functional in vivo half-life. Alternative terms to plasma half-life include serum half-life, circulating half-life, circulatory half-life, serum clearance, plasma clearance, and clearance half-life. The functionality to be retained is normally selected from procoagulant, proteolytic, co-factor binding, receptor binding activity, or other type of biological activity associated with the particular protein.

Measurement of in vivo biological half-life can be carried out in a number of ways as described in the literature. An example using modified FVIIa (coagulation factor VIIa) of an assay for the measurement of in vivo half-life of rFVIIa and variants thereof is described in FDA reference number 96-0597. Briefly, FVIIa clotting activity is measured in plasma drawn prior to and during a 24-hour period after administration of the modified protein. The median apparent volume of distribution at steady state is measured and the median clearance determined.

The term "increased" as used about the functional in vivo half-life or plasma half-life indicates that the relevant half-life of the modified protein is statistically significantly increased relative to that of a reference molecule, such as an otherwise identical protein which has, however, not been subjected to the method of the invention. Thus, the half-life is determined under comparable conditions. For instance the relevant half-life may be increased by at least about 25%, such as by at least about 50%, e.g., by at least about 100%, 150%, 200%, 250%, or 500%. In some embodiments, the modified proteins of the present invention exhibit an increase in half-life of at least about 0.25 h, preferably at least about 0.5 h, more preferably at least about 1 h, and most preferably at least about 2 h, relative to the half-life of the un-modified protein.

The term "bioavailability" refers to the proportion of an administered dose of a conjugate that can be detected in plasma at predetermined times after administration. Typically, bioavailability is measured in test animals by administering a dose of between about 25-250 μg/kg of the preparation; obtaining plasma samples at predetermined times after administration; and determining the content of protein in the samples using a suitable bioassay, or immunoassay, or an equivalent assay. The data are typically displayed graphically as [protein] v. time and the bioavailability is expressed as the area under the curve (AUC). Relative bioavailability of a test preparation refers to the ratio between the AUC of the test preparation and that of the un-modified protein.

The term "immunogenicity" of a preparation refers to the ability of the preparation, when administered to a human, to elicit a deleterious immune response, whether humoral, cellular, or both. In any human sub-population, there may exist individuals who exhibit sensitivity to particular administered proteins. Immunogenicity may be measured by quantifying the presence of anti-protein antibodies and/or protein responsive T-cells in a sensitive individual, using conventional methods known in the art. In some embodiments, the modified proteins of the present invention exhibit a decrease in immunogenicity in a sensitive individual of at least about 10%, preferably at least about 25%, more preferably at least about 40% and most preferably at least about 50%, relative to the immunogenicity for that individual of the un-modified protein.

Immunogenicity of a drug also relates to the fact that proteinaceous drugs may be immunogenic in non-sensitive subjects, meaning that repeated administrations of the drug leads to continuous boosting of an immune response against the drug. This is in most cases undesirable because the immune response will interfere with the activity of the drug, whereby it becomes necessary to administer increasing dosages of the drug over time in order to provide a therapeutic effect. In some embodiments, the modified proteins of the present invention exhibit a decrease in immunogenicity in non-sensitive subjects of at least about 10%, preferably at least about 25%, more preferably at least about 40% and most preferably at least about 50%, relative to the immunogenicity for that individual of the un-modified protein.

The term "protease protected" as used herein referring to a protein means a protein which has been chemically modified in order to render said compound resistant to the plasma peptidases or proteases. Proteases in plasma are known to be involved in the degradation of several peptide hormones and also play a role in degradation of larger proteins.

Resistance of a protein to degradation by for instance dipeptidyl aminopeptidase IV (DPPIV) is determined by the following degradation assay: Aliquots of the protein (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis.

One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed. The experiment can optionally be run in the presence of albumin, in order to study shielding properties exerted by albumin complexation.

The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

The term "identity" as known in the art, refers to a relationship between the sequences of two or more proteins, as determined by comparing the sequences. In the art, "identity" also means the degree of sequence relatedness between proteins, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM *J. Applied Math.*, 48, 1073, (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., *Nucl. Acid. Res.*, 12, 387, (1984); Genetics Computer Group, University of Wisconsin, Madison, Wis.), BLASTP, BLASTN, and FASTA (Altschul et al., *J. Mol. Biol.*, 215, 403-410, (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two proteins for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., *Proc. Natl. Acad. Sci. USA*, 89, 10915-10919, (1992) for the BLOSUM 62 comparison matrix) is also used by the algorithm.

Preferred parameters for a protein sequence comparison include the following: Algorithm: Needleman et al., *J. Mol. Biol*, 48, 443-453, (1970); Comparison matrix: BLOSUM 62 from Henikoff et al., *Proc. Natl. Acad. Sci. USA*, 89, 10915-10919, (1992); Gap Penalty: 12, Gap Length Penalty: 4, Threshold of Similarity: 0.

The GAP program is useful with the above parameters. The aforementioned parameters are the default parameters for protein comparisons (along with no penalty for end gaps) using the GAP algorithm.

DETAILED DESCRIPTION OF THE INVENTION

According to a first aspect of the invention, there is provided a process for preparing a conjugated protein or glycoprotein which comprises the steps of reacting a protein or glycoprotein with a water insoluble albumin binder in the presence of an optionally substituted cyclodextrin molecule.

In one embodiment, the protein conjugate is a protein conjugate of the formula (I):

$$(A-W-B)_y-P \qquad (I)$$

wherein
P represents a protein or glycoprotein;
B represents a hydrophilic spacer;
W is a chemical group linking A and B;
A represents an albumin binding residue; and
y represents an integer selected from 1, 2, 3, 4, 5, 6, 7, 8, 9 or 10;
or a pharmaceutically acceptable salt, solvate or prodrug thereof, such that said A—W—B— moiety comprises a water insoluble moiety.

The invention results in modified proteins or glycoproteins having improved pharmacologic properties compared to the un-modified protein or glycoprotein. For example, the improved pharmacologic property is selected from the group consisting of increased bioavailability, increased functional in vivo half-life, increased in vivo plasma half-life, reduced immunogenicity, increased protease resistance, increased affinity for albumin, improved affinity for a receptor, increased storage stability, decreased functional in vivo half-life and decreased in vivo plasma half-life.

Cyclodextrins (also known as cycloamyloses) make up a family of cyclic oligosaccharides, composed of 5 or more α-D-glucopyranoside units linked 1→4 as in amylose (a fragment of starch). Typical cyclodextrins contain a number of glucose monomers ranging from six to eight units in a ring, creating a cone shape. Examples of such cyclodextrins include α-cyclodextrin (α-CD; six membered sugar ring molecule), β-cyclodextrin (β-CD; seven sugar ring molecule) and γ-cyclodextrin (γ-CD; eight sugar ring molecule) as shown below:

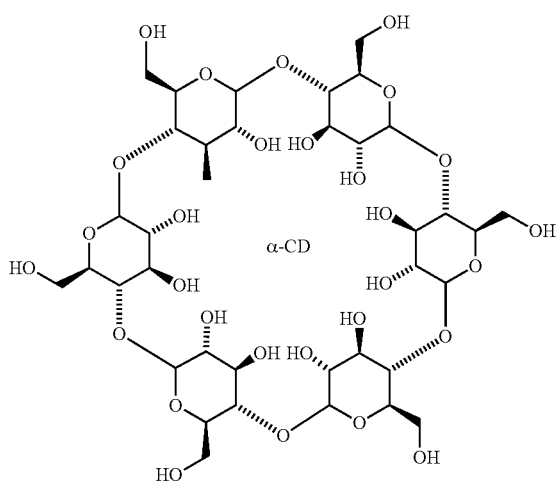

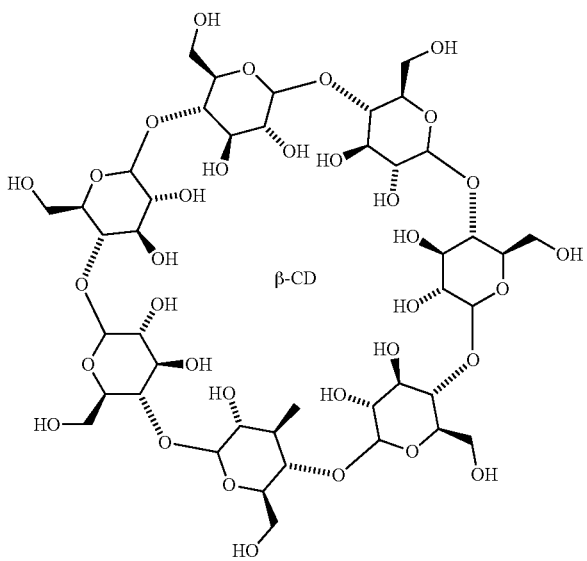

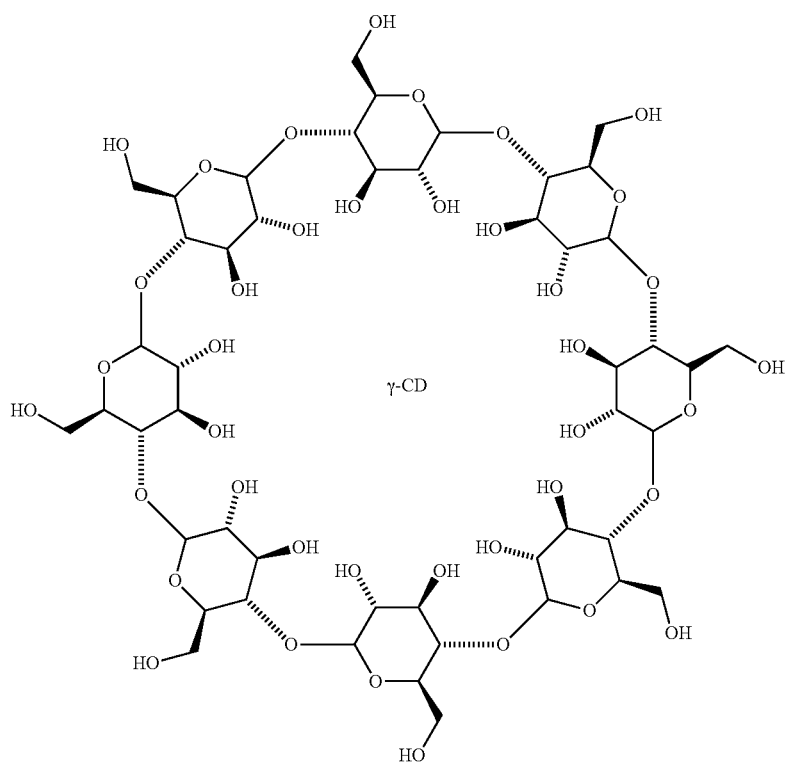

In one embodiment, the cyclodextrin molecule comprises optionally substituted β-cyclodextrin.

Optional substituents for cyclodextrin include one or more $C_{1-6}$ alkyl groups (e.g. methyl, ethyl or propyl) each of which may be optionally substituted by one or more hydroxyl groups (e.g. hydroxyethyl-cyclodextrin or hydroxypropyl-cyclodextrin). In one embodiment, the optionally substituted cyclodextrin comprises 2-hydroxyethyl-β-cyclodextrin.

The optionally substituted cyclodextrin molecule may be added at a concentration of between 1% and 10% (e.g. 5%).

In one embodiment, the conjugation reaction comprises reaction in an aqueous buffered solution, such as a Hepes buffer (e.g. 50 mM Hepes, 100 mM NaCl and 10 mM $CaCl_2$). In one embodiment, the conjugation reaction comprises reaction at a constant pH (e.g. pH 7.0) and a constant temperature (e.g. 25° C.). The advantage of conducting the conjugation reaction at a constant pH and temperature is to reduce the likelihood of denaturing the blood coagulation factor.

Besides clot factors the invention also applies to large proteins that are not related to, or are only remotely related to clot factors. Large proteins are in this context proteins with molecular masses above 10.000 Da.

Thus in one embodiment, P represents a protein with a molecular mass above 10,000 Da.

In another embodiment, P represents a protein with a molecular mass above 20,000 Da.

In another embodiment, P represents a protein with a molecular mass above 30,000 Da.

In another embodiment, P represents a protein with a molecular mass above 40,000 Da.

Proteins and peptides within the scope of P include, but are not limited to, hemoglobin, serum proteins such as blood factors including Factors VII, FX, FII, FV, protein C, protein S, tPA, PAI-1, tissue factor, FXI, FXII, and FXIII, as well as sequence FVIII and FIX variants thereof; immunoglobulins, cytokines such as interleukins, alpha-, beta-, and gamma-interferons, colony stimulating factors including granulocyte colony stimulating factors, platelet derived growth factors and phospholipase-activating protein (PUP).

Other proteins and peptides of general biological and therapeutic interest include insulin, plant proteins such as lectins and ricins, tumor necrosis factors and related alleles, soluble forms of tumor necrosis factor receptors, interleukin receptors and soluble forms of interleukin receptors, growth factors such as tissue growth factors, such as TGFa's or TGFps and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

In an embodiment of the invention the peptide is aprotinin, tissue factor pathway inhibitor or other protease inhibitors, insulin or insulin precursors, human or bovine growth hormone, interleukin, glucagon, oxyntomodulin, GLP-1, GLP-2, IGF-I, IGF-II, tissue plasminogen activator, transforming growth factor γ or β, platelet-derived growth factor, GRF (growth hormone releasing factor), human growth factor, immunoglobulins, EPO, TPA, protein C, blood coagulation factors such as FVII, FVIII, FIX, FX, FII, FV, protein C, protein S, PAI-1, tissue factor, FXI, FXII, and FXIII, exendin-3, exentidin-4, and enzymes or functional analogues thereof. In the present context, the term "functional analogue" is meant to indicate a protein with a similar function as the native protein. The protein may be structurally similar to the native protein and may be derived from the native protein by addition of one or more amino acids to either or both the C and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Furthermore the protein may be acylated in one or more positions, see, e.g., WO 98/08871, which discloses acylation of GLP-1 and analogues thereof, and WO 98/08872, which discloses acylation of GLP-2 and analogues thereof. An example of an acylated GLP-1 derivative is Lys26 ($N^{epsilon}$-tetradecanoyl)-GLP-1 (7-37) which is GLP-1 (7-37) wherein the epsilon-amino group of the Lys residue in position 26 has been tetradecanoylated.

The proteins or portions thereof can be prepared or isolated by using techniques known to those of ordinary skill in the art such as tissue culture, extraction from animal sources, or by recombinant DNA methodologies. Transgenic sources of the proteins, peptides, amino acid sequences and the like are also contemplated. Such materials are obtained from transgenic animals, i.e., mice, pigs, cows, etc., wherein the protein is expressed in milk, blood or tissues. Transgenic insects and baculovirus expression systems are also contemplated as sources. Moreover, mutant versions, of proteins, such as mutant TNF's and/or mutant interferons are also within the scope of the invention. Other proteins of interest are allergen proteins such as ragweed, Antigen E, honeybee venom, mite allergen, and the like.

In one embodiment, P represents a blood coagulation factor. Examples of suitable blood coagulation factors include: I (fibrinogen), II (prothrombin), tissue factor, V (proaccelerin), VI, VII, VIII, IX (Christmas factor), X (Stuart-Prower factor), XI plasma thromboplastin antecedent), XII (Hageman factor), XIII (fibrin-stabilizing factor), von Willebrand factor, prekallikrein, high molecular weight kininogen (HMWK), fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2) and cancer procoagulant. In a further embodiment, the blood coagulation factor is selected from FVII, FX, FII, FV, protein C, protein S, tPA, PAI-1, tissue factor, FXI, FXII, and FXIII, as well as sequence FVIII, FIX variants thereof.

In a further embodiment, the blood coagulation factor is FVII (i.e. FVIIa).

In an alternative embodiment, P represents a growth hormone (GH).

In one embodiment, y represents an integer selected from 1, 2 or 3. This embodiment is particularly suited to embodiments wherein P represents a growth hormone because said growth hormone has 3 attachment points for such an A—W—B— moiety, namely N-term, Gln40 and Gln141.

In one embodiment, y represents an integer selected from 1, 2, 3, 4, 5 or 6. In a further embodiment, y represents 2. In an alternative embodiment, y represents 1.

The above embodiments as well as the embodiments to be described hereunder should be seen as referring to any one of the aspects described herein as well as any one of the embodiments described herein unless it is specified that an embodiment relates to a certain aspect or aspects of the present invention.

In one embodiment of the present invention the hydrophilic spacer B has a cLogP<0 as defined in *J. Am. Chem. Soc.*, 86 (1964) 5175-5180 "A New Substituent Constant, π, Derived from Partition Coefficients", and as can be calculated using the Sybyl software package from Tripos (Tripos Associates, 1699 South Hanley Road, St. Louis, Mo. 63144-2319 USA).

In a further embodiment of the conjugate of formula (I), the hydrophilic spacer B has the formula

wherein $X_1$ is —$W_1$—[(CHR$^1$)$_{l1}$—$W_2$]$_{m1}$—{[(CH$_2$)$_{n1}$E1]$_{m2}$-[(CHR$^2$)$_{l2}$—$W_3$]$_{m3}$}$_{n2}$—, $X_2$ is —[(CHR$^3$)$_{l3}$—$W_4$]$_{m4}$—{[(CH$_2$)$_{n3}$E2]$_{m5}$-[(CHR$^4$)$_{l4}$—$W_5$]$_{m5}$}$_{n4}$—, $X_3$ is —[(CHR$^5$)$_{l5}$—$W_6$]$_{m7}$—, $X_4$ is F-D1-(CH$_2$)$_{l6}$-D2-, I1, I2, I3, I4, I5 and I6 independently are selected from 0-16, m1, m3, m4, m6 and m7 independently are selected from 0-10, m2 and m5 independently are selected from 0-25, n1, n2, n3 and n4 independently are selected from 0-16, F is aryl, heteroaryl, pyrrolidine-2,5-dione, wherein the aryl and heteroaryl groups are optionally substituted with halogen, —CN, —OH, —C(O)OH, —C(O)NH$_2$, —S(O)$_2$OH or C$_{1-6}$-alkyl, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or heteroaryl; wherein the alkyl, aryl and heteroaryl groups optionally are substituted with halogen, —C(O)OH, —C(O)NH$_2$, —S(O)OH, —S(O)$_2$OH, —CN or —OH, D1, D2, E1 and E2 independently are selected from —O—, —NR$^6$—, —N(COR$^7$)— or a valence bond; wherein R$^6$ and R$^7$ independently represent hydrogen or C$_{1-6}$-alkyl, W$_1$ to W$_6$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1.

In a further embodiment W$_1$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_1$ is selected from —C(O)NH—, —NHC(O)— or —C(O)NHS(O)$_2$—.

In a further embodiment W$_2$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_2$ is selected from —C(O)NH—, —NHC(O)— or —C(O)NHS(O)$_2$—.

In a further embodiment W$_3$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_3$ is selected from —C(O)NH—, —NHC(O)— or —C(O)NHS(O)$_2$—.

In a further embodiment W$_4$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_4$ is selected from —C(O)NH—, —NHC(O)— or —C(O)NHS(O)$_2$—.

In a further embodiment W$_5$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_5$ is selected from —C(O)NH—, —NHC(O)— or —C(O)NHS(O)$_2$—.

In a further embodiment W$_6$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_6$ is selected from —C(O)NH—, —NHC(O)— or —C(O)NHS(O)$_2$—.

In a further embodiment R$^1$ selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^1$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^2$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^2$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^3$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^3$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^4$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^4$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^5$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^5$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment E1 is selected from —O— or —NR$^6$— or a valence bond. Typically, E1 is selected from —O—.

In a further embodiment E2 is selected from —O— or —NR$^6$— or a valence bond. Typically, E2 is selected from —O—.

In a further embodiment E1 and E2 are both —O—.

In a further embodiment E1 and E2 are both —NR$^6$—.

In a further embodiment F is phenyl, pyrrolidine-2,5-dione or a valence bond.

In a further embodiment D1 is selected from —O— or —NR$^6$— or a valence bond. Typically, D1 is selected from —NR$^6$—.

In a further embodiment D2 is selected from —O— or —NR$^6$— or a valence bond. Typically, D1 is selected from —NR$^6$—.

In a further embodiment I1 is 0-6, such as 0, 1, 2, 3, 4, 5 or 6.

In a further embodiment I2 is 0-6, such as 0, 1, 2, 3, 4, 5 or 6.

In a further embodiment I3 is 0-6, such as 0, 1, 2, 3, 4, 5 or 6.

In a further embodiment I4 is 0-6, such as 0, 1, 2, 3, 4, 5 or 6. In a further embodiment I5 is 0-6, such as 0, 1, 2, 3, 4, 5 or 6.

In a further embodiment I6 is 0-6, such as 0, 1, 2, 3, 4, 5 or 6.

In a further embodiment m1 is 0-6, such as 0, 1, 2, 3, 4, 5 or 6.

In a further embodiment m2 is 0-10, such as 0, 1, 2, 3, 4, 5, 6, 7, 8, 9, or 10.

In a further embodiment m3 is 0-6, such as 0, 1, 2, 3, 4, 5 or 6.

In a further embodiment m4 is 0-6, such as 0, 1, 2, 3, 4, 5 or 6.

In a further embodiment m5 is 0-10, such as 0, 1, 2, 3, 4, 5, 6, 7, 8, 9, or 10.

In a further embodiment m6 is 0-6, such as 0, 1, 2, 3, 4, 5 or 6.

In a further embodiment m7 is 0-6, such as 0, 1, 2, 3, 4, 5 or 6.

In a further embodiment n1 is 0-10, such as 0, 1, 2, 3, 4, 5, 6, 7, 8, 9 or 10.

In a further embodiment n2 is 0-10, such as 0, 1, 2, 3, 4, 5, 6, 7, 8, 9 or 10.

In a further embodiment n3 is 0-10, such as 0, 1, 2, 3, 4, 5, 6, 7, 8, 9 or 10.

In a further embodiment n4 is 0-10, such as 0, 1, 2, 3, 4, 5, 6, 7, 8, 9 or 10.

In a further embodiment X$_1$ is —W$_1$—[(CHR$^1$)$_{l1}$—W$_2$]$_{m1}$—{[(CH$_2$)$_{n1}$O]$_{m2}$—[(CHR$^2$)$_{l2}$—W$_3$]$_{m3}$}$_{n2}$— and X$_2$ is —[(CHR$^3$)$_{l3}$—W$_4$]$_{m4}$—{[(CH$_2$)$_{n3}$O]$_{m5}$—[(CHR$^4$)$_{l4}$—W$^5$]$_{m6}$}$_{n4}$—, wherein —{[(CH$_2$)$_{n1}$O]$_{m2}$—[(CHR$^2$)$_{l2}$—W$_3$]$_{m3}$}$_{n2}$— and —{[(CH$_2$)$_{n3}$O]$_{m5}$—[(CHR$^4$)$_{l4}$—W$_5$]$_{m6}$}$_{n4}$— are selected from,

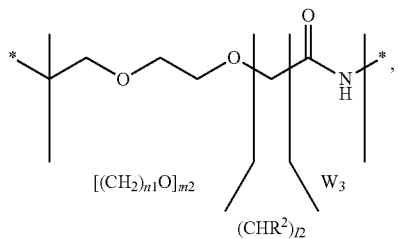
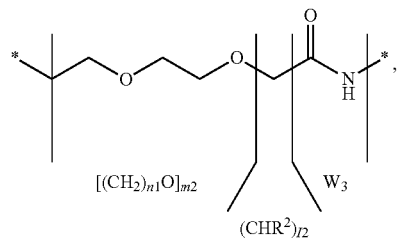
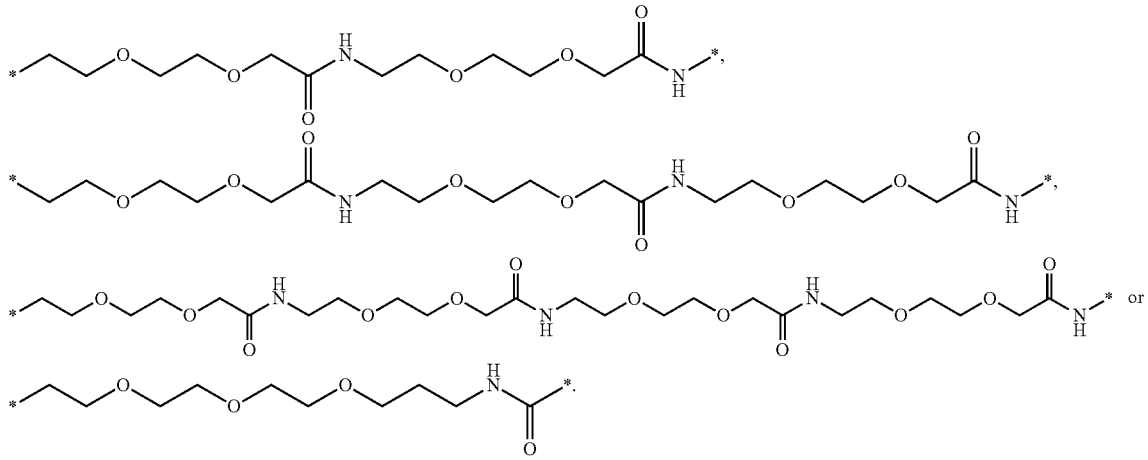

In a further embodiment the molar weight of said hydrophilic spacer is in the range from 80 Daltons (D) to 1500 D or in the range from 500 D to 1100 D.

In a still further embodiment W has the formula

—W$_7$—Y—, wherein
Y is —(CH$_2$)$_{I7}$—C$_{3-10}$-Cycloalkyl-W$_8$— or a valence bond,
I7 is 0-6,
W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1,
W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

In an embodiment of W, Y is —(CH$_2$)$_{I7}$-cyclohexyl-W$_8$—.
In a further embodiment Y is a valence bond.
In an embodiment W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_7$ is selected from —C(O)NH—, —NHC(O)—, —C(O)NHS(O)$_2$.

In a further embodiment W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_8$ is selected from —C(O)NH—, —NHC(O)—, —C(O)NHS(O)$_2$.

In a further embodiment I7 is 0 or 1.
In a further embodiment the hydrophilic spacer B of the present invention is selected from

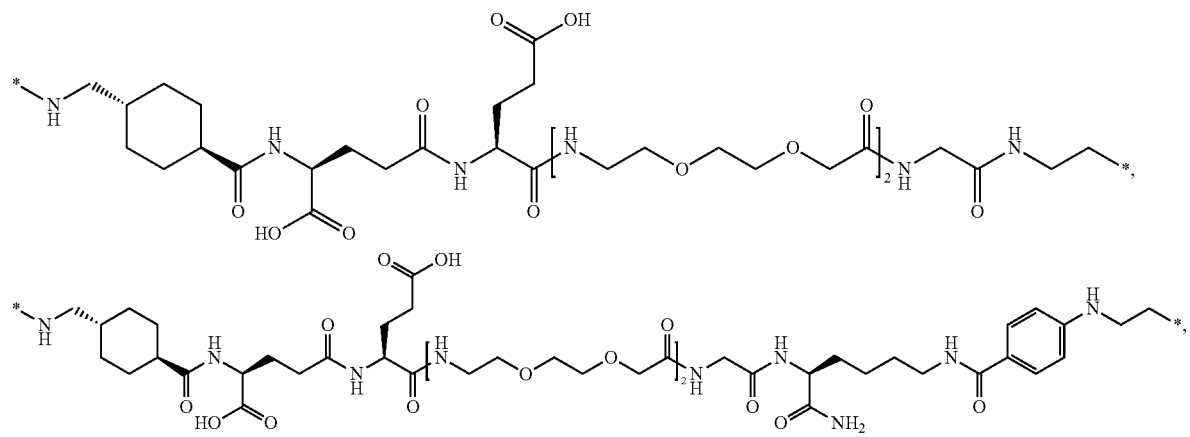

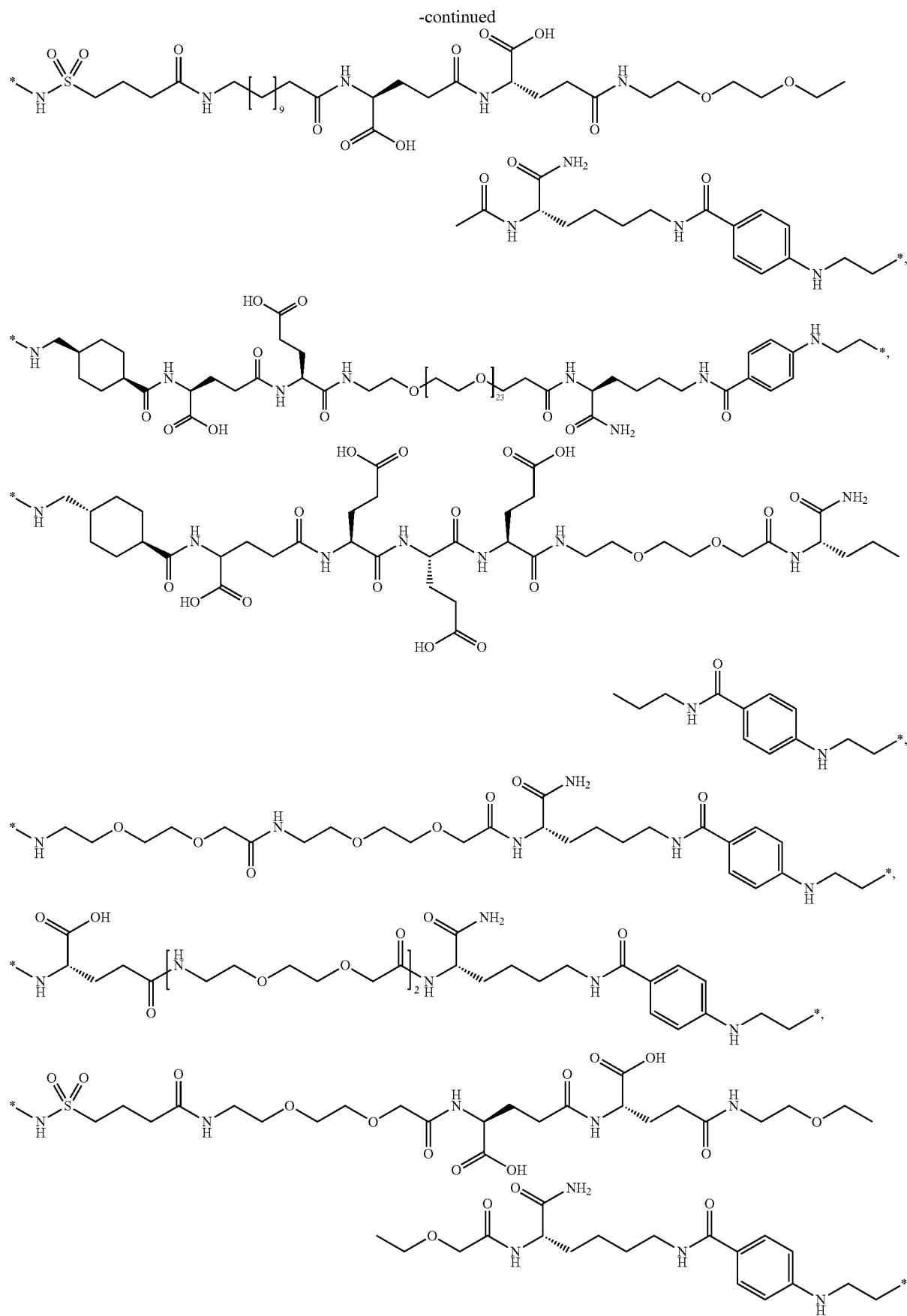

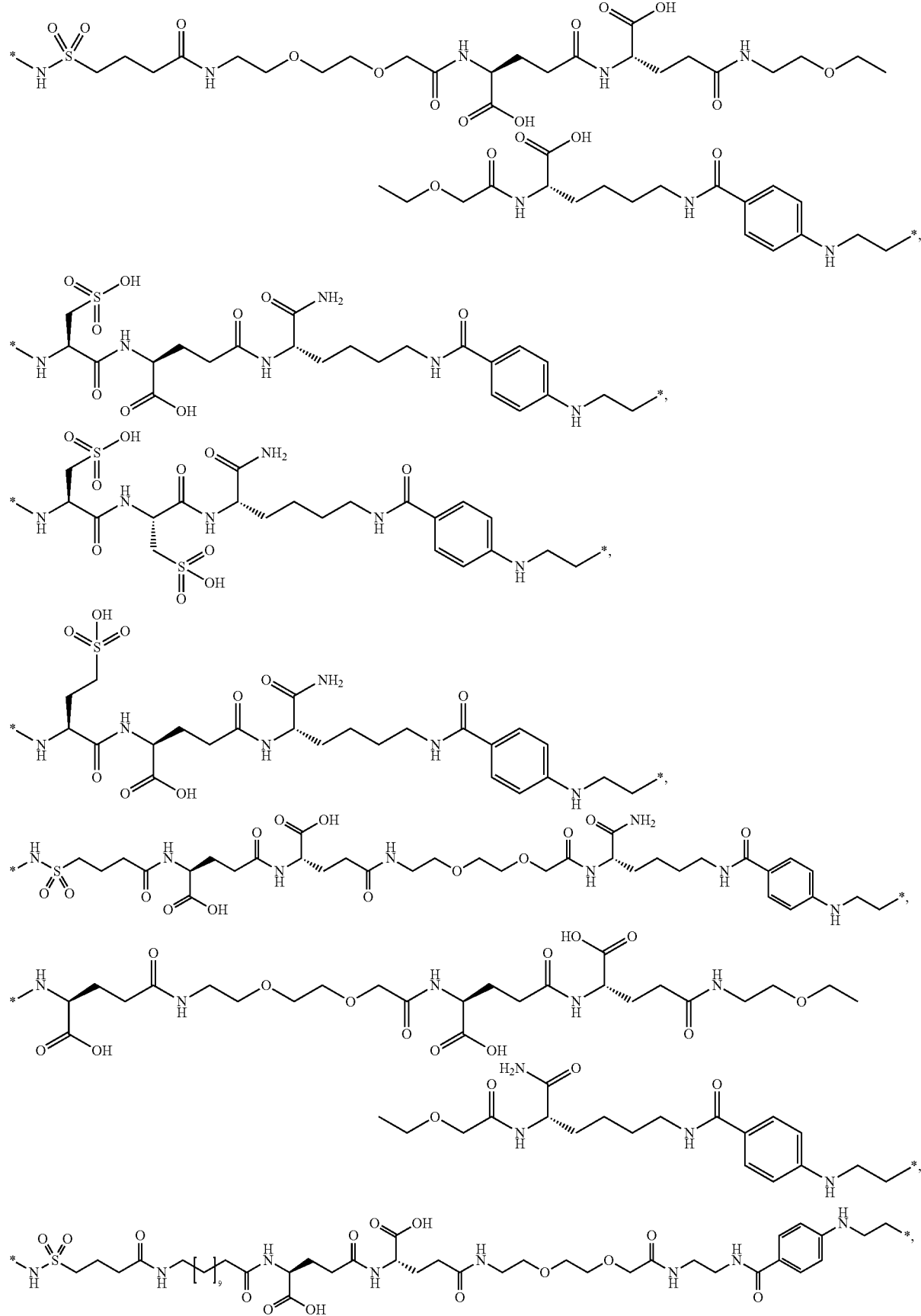

-continued

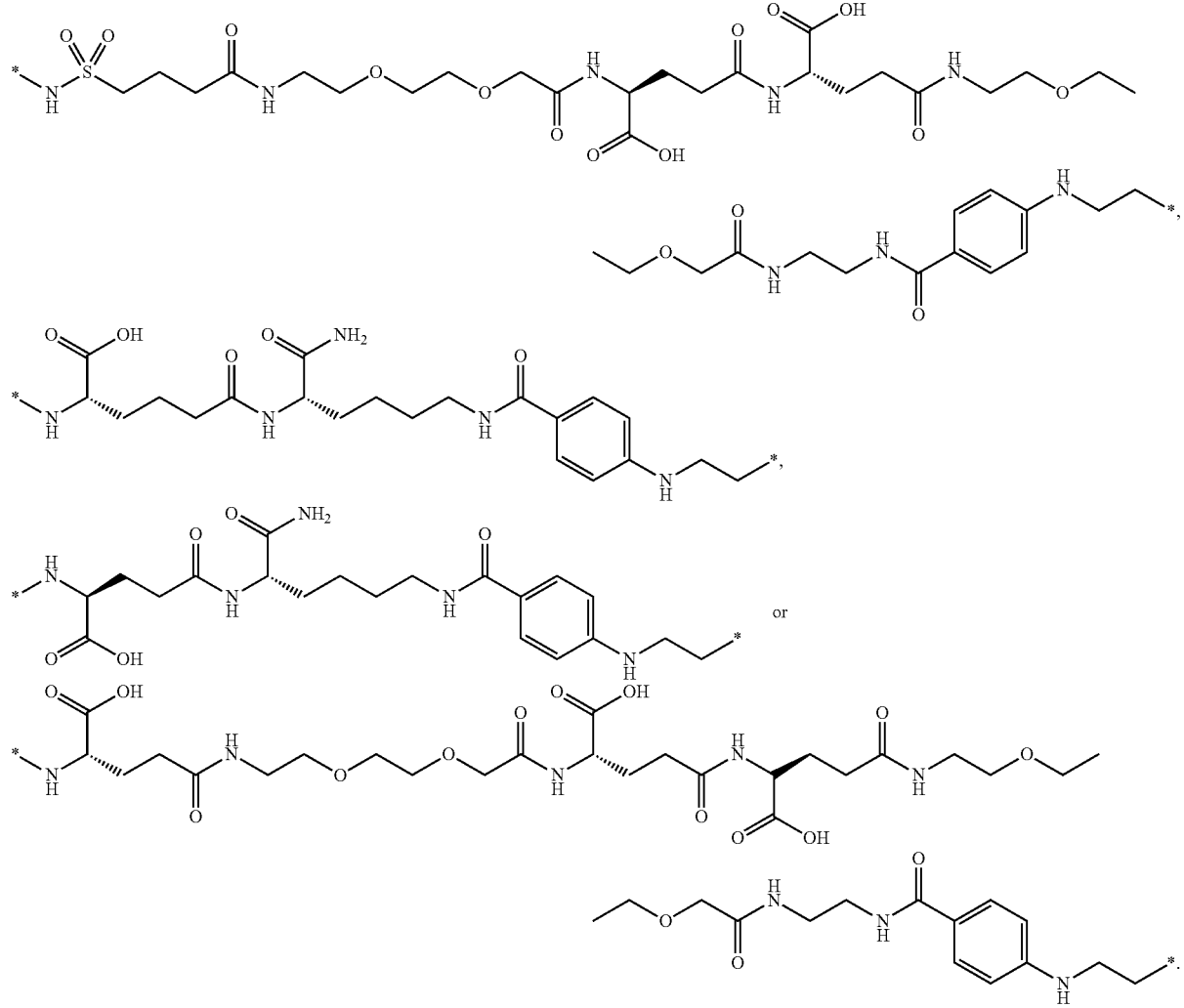

The albumin binding residue (substituent A in formula (I) above) attached to P is a lipophilic residue, which binds non-covalently to albumin. Typically, the albumin binding residue is negatively charged at physiological pH, and has a binding affinity towards human serum albumin that is below about 10 µM or even below about 1 µM.

Albumin binders used in this invention are typically fatty acid derivatives with low solubility in aqueous solution. Solubility of an albumin binder can be described by its log P value. Log P, also known as the partition coefficient, is the logarithm of the ratio of concentrations of a compound in the two phases of a mixture of two immiscible solvents at equilibrium. Typically one of the solvents is water while the second is selected from octan-1-ol, chloroform, cyclohexane and propylene glycol dipelargonate (PGDP). Log P values measured in these different solvents show differences principally due to hydrogen bonding effects. Octanol can donate and accept hydrogen bonds whereas cyclohexane is inert. Chloroform can donate hydrogen bonds whereas PGDP can only accept them.

In one embodiment of the invention, the albumin binder has a Log P of >−3 in either octan-1-ol, chloroform, cyclohexane and propylene glycol dipelargonate (PGDP).

In a further embodiment, the albumin binder has a log P above −4 in either octan-1-ol, chloroform, cyclohexane and propylene glycol dipelargonate (PGDP). In a yet further embodiment, the albumin binder has a log P above −5 in either octan-1-ol, chloroform, cyclohexane and propylene glycol dipelargonate (PGDP).

Alternatively, or cLogP can be calculated for the albumin binder part using published algorithms (*J. Am. Chem. Soc.*, 86 (1964) 5175-5180 "A New Substituent Constant, π, Derived from Partition Coefficients", C. A. Lipinski et al. *Advanced Drug Delivery Reviews*, 23 (1997) 3-25, "Experimental and Computational Approaches to Estimate Solubility and Permeability in Drug Discovery and Development Settings" and I. Moriguchi, S. Hirono, I. Nakagome, H. Hirano, *Chem. and Pharm. Bull.*, 42 (1994) 976-978 "Comparison of Reliability of logP Values for Drugs Calculated by Several Methods".

In one embodiment of the invention, the albumin binder has a cLog P of >1 in either octan-1-ol, chloroform, cyclohexane and propylene glycol dipelargonate (PGDP). In a further embodiment of the invention, the albumin binder has a cLog P of >2 in either octan-1-ol, chloroform, cyclohexane and propylene glycol dipelargonate (PGDP). In a yet further embodiment of the invention, the albumin binder has a cLog P of >3 in either octan-1-ol, chloroform, cyclohexane and propylene glycol dipelargonate (PGDP). In a yet further embodiment, the albumin binder has a clog P of >4 in either octan-1-ol, chloroform, cyclohexane and propylene glycol dipelargonate (PGDP). In a yet further embodiment, the albumin binder has a clog P of >5 in either octan-1-ol, chloroform, cyclohexane and propylene glycol dipelargonate (PGDP).

In a further embodiment the albumin binding residue is selected from a straight chain alkyl group, a branched alkyl group, a group which has a ω-carboxylic acid group or a ω-carboxylic acid isoster. Typically, the albumin binding residue has from 6 to 40 carbon atoms. In a further embodiment the albumin binding residue has from 8 to 26 carbon atoms. In a further embodiment the albumin binding residue has from 8 to 20 carbon atoms.

In a further embodiment A has 14 to 26 carbon atoms and comprises a ω-carboxylic acid group. In a further embodiment A has 14 to 26 carbon atoms and comprises a ω-carboxylic acid isoster, such as a tetrazol.

Albumin binding properties can be measured by surface plasmon resonance as described in J. Biol. Chem. 277(38), 35035-35042, 2002.

In a further embodiment A is selected from

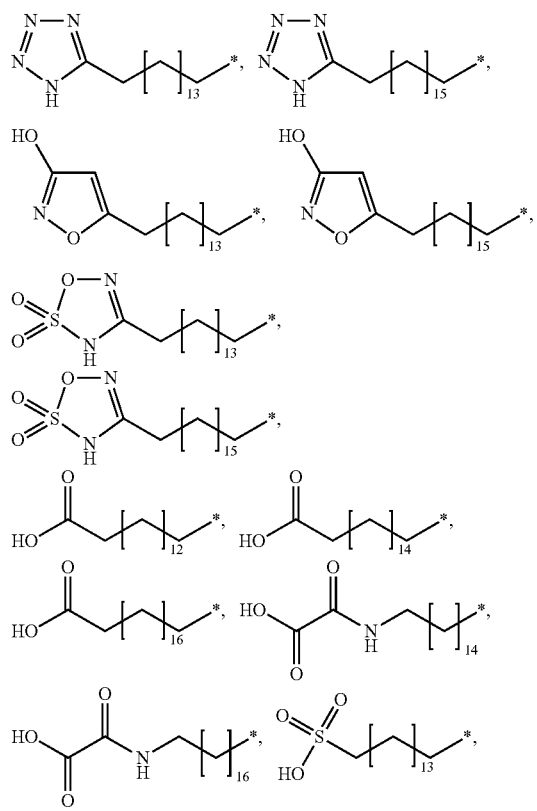

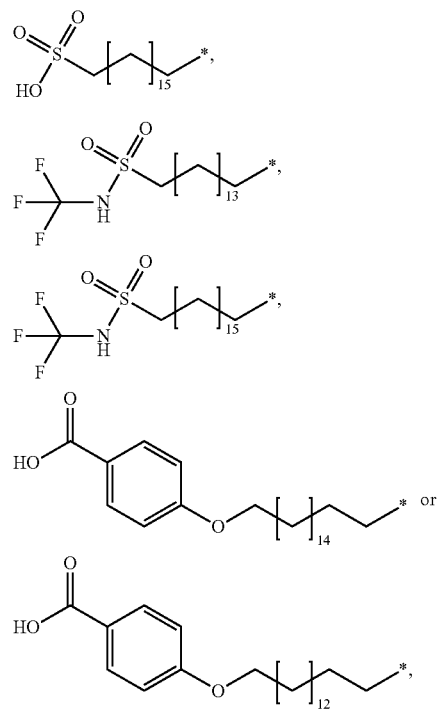

wherein * denotes the attachment to B through W.

In one embodiment the albumin binding residue A is attached to the glutamine residue of protein P via hydrophilic spacer B.

In another embodiment the albumin binding residue A is attached to a cystein residue of protein P via hydrophilic spacer B.

In another embodiment the albumin binding residue A is attached to the N-terminal residue of protein P via hydrophilic spacer B.

In another embodiment the albumin binding residue A is attached to the C-terminal residue of protein P via hydrophilic spacer B.

In another embodiment the albumin binding residue A is attached to a lysine residue of protein P via hydrophilic spacer B.

In yet another embodiment the albumin binding residue A is attached to an oxidized glycan residue of glycoprotein P via hydrophilic spacer B.

In one embodiment, A-W—B— is

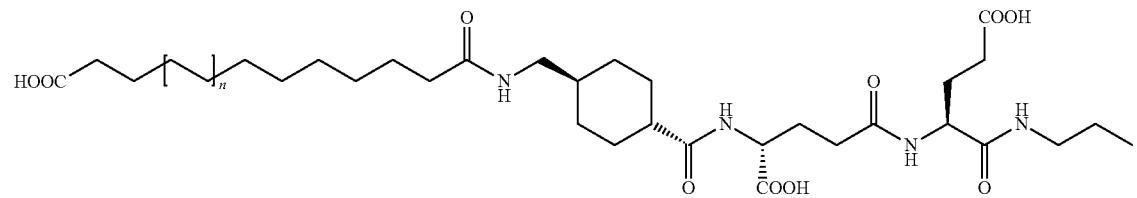

-continued
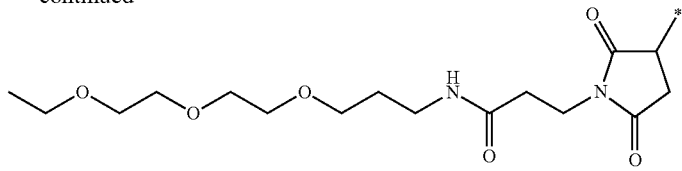
n = 5
In one embodiment, P is FVIIa-C407, and A-W—B—P is
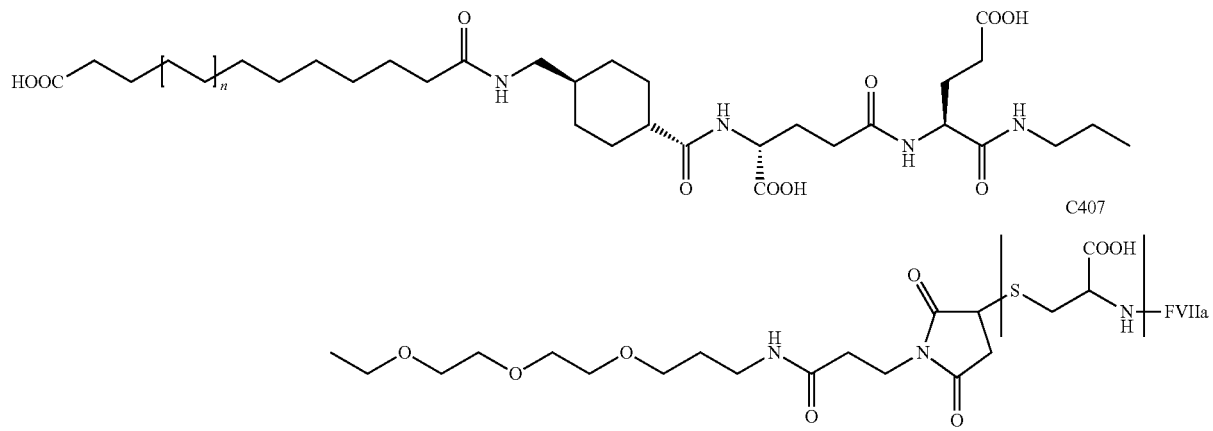
n = 5
In one embodiment, A-W—B= is
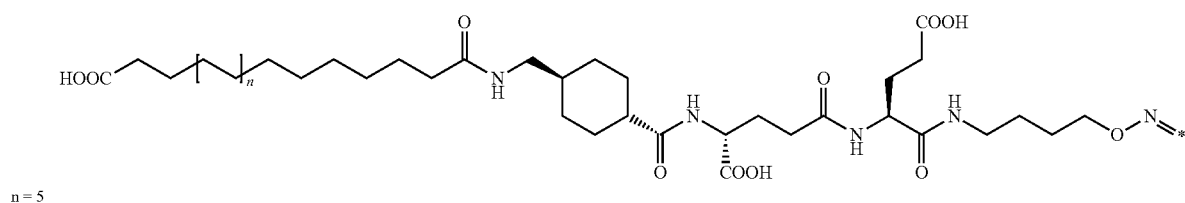
n = 5
In one embodiment, P is glycooxidized FVIIa, and A-W—B=P is
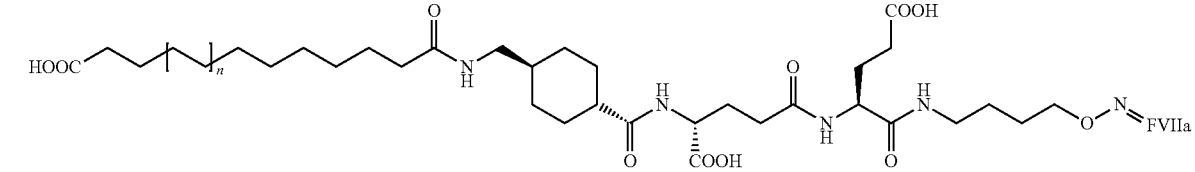
n = 5

In one embodiment, P is glycooxidized FVIIa, y=2 and (A-W—B=)$_y$P is
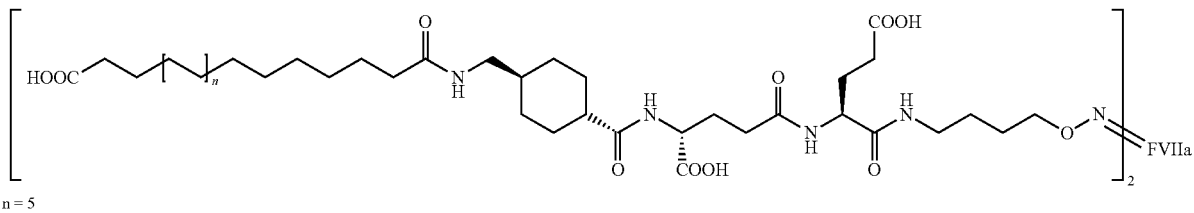
In one embodiment, P is glycooxidized FVIIa, y=3 and (A-W—B=)$_y$P is
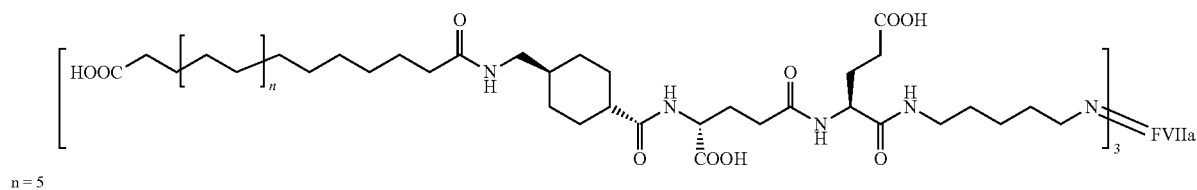
In one embodiment, A-W—B— is
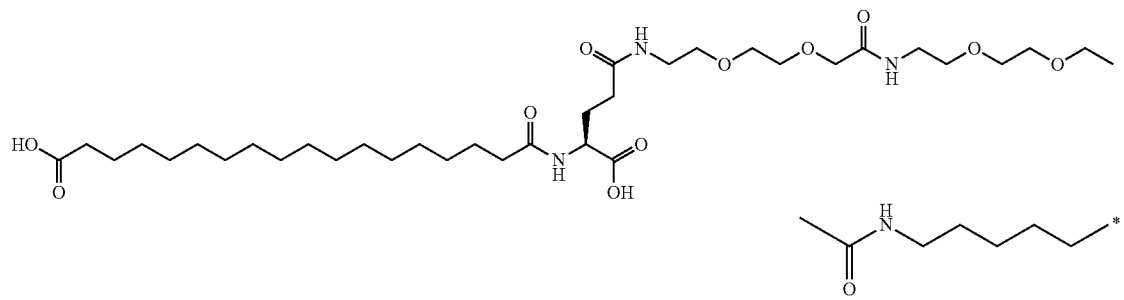
In one embodiment, P is hGH, and A-W—B—P is
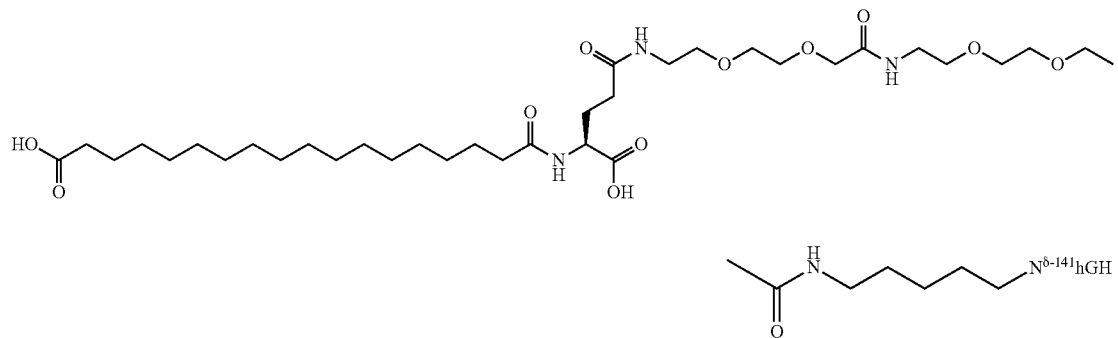

In one embodiment, P is hGH, y=2 and (A-W—B)$_y$—P is
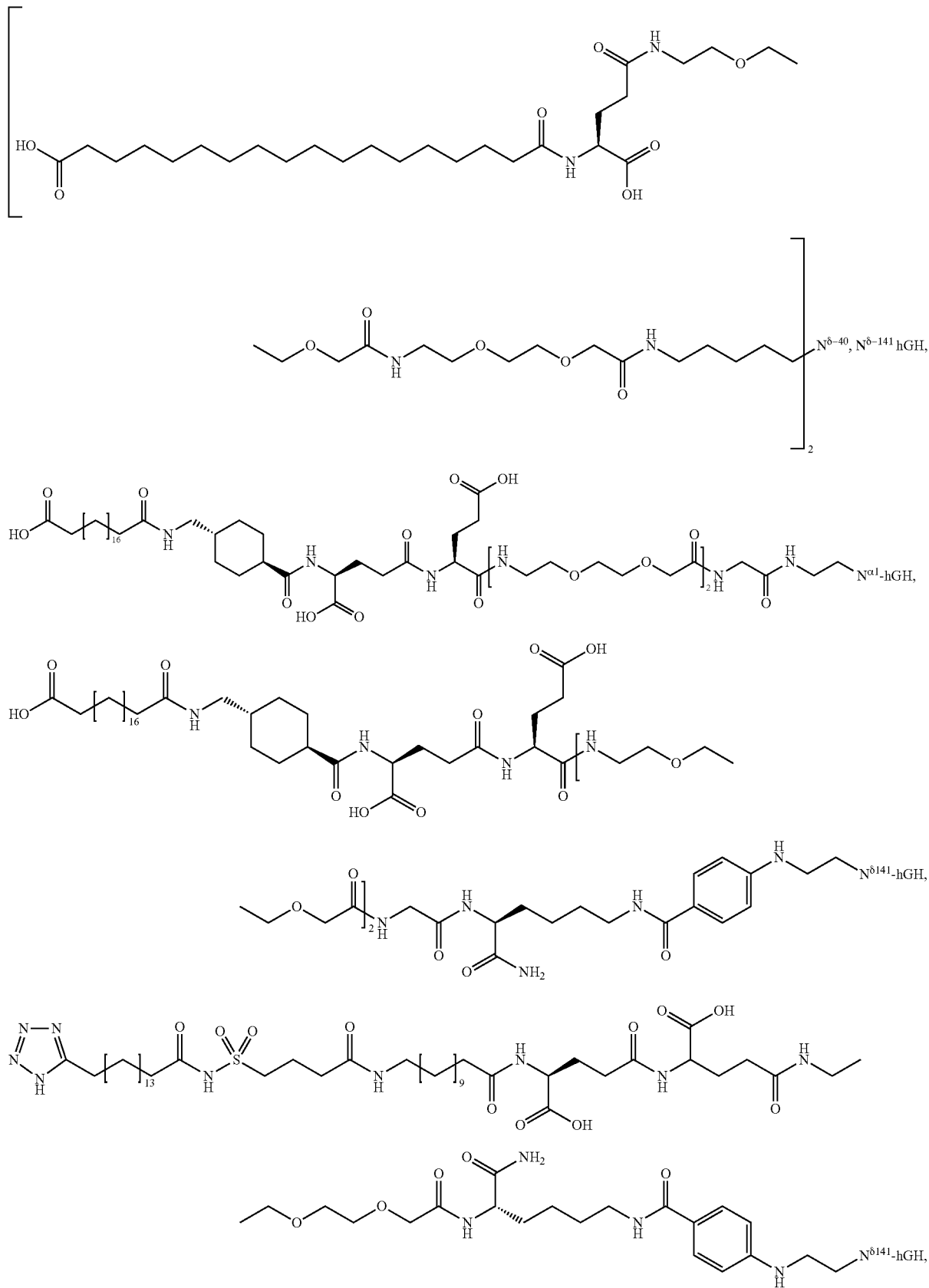

-continued
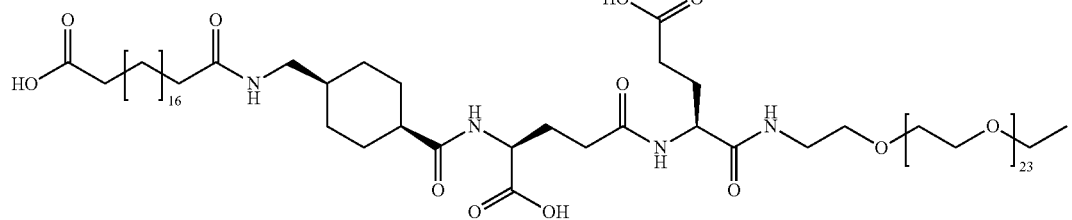
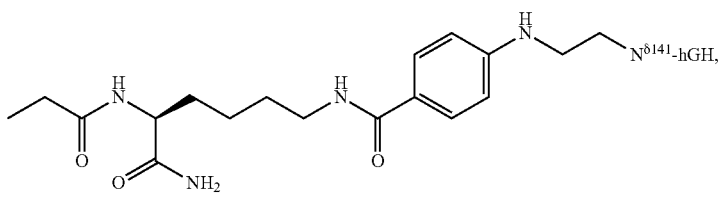
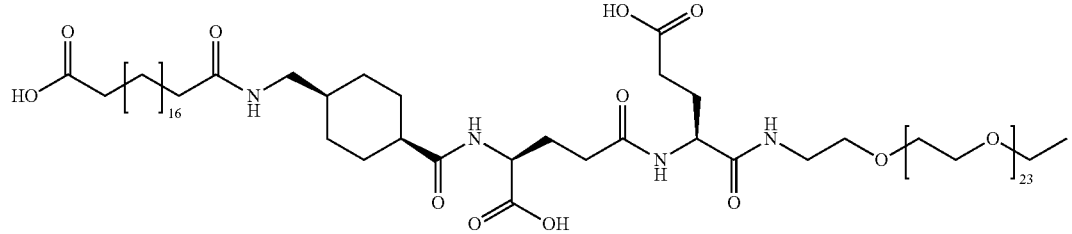
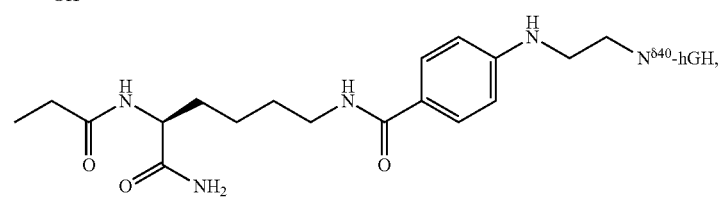
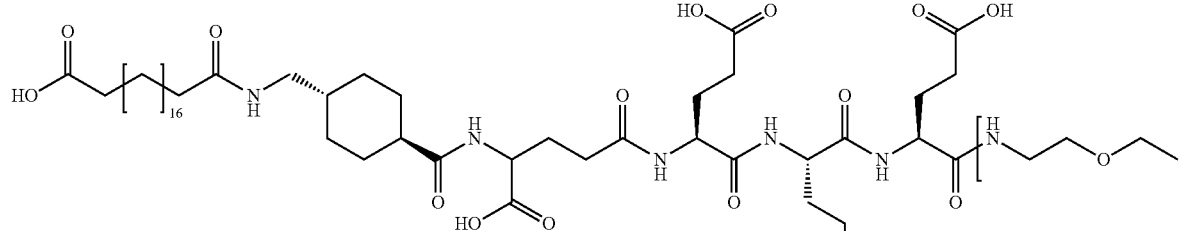
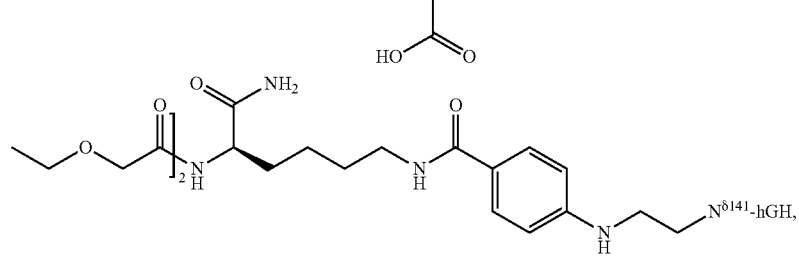
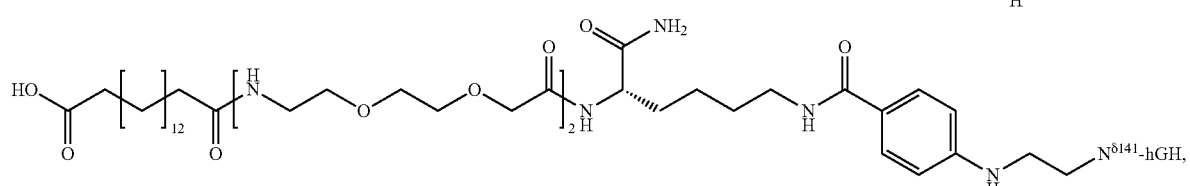
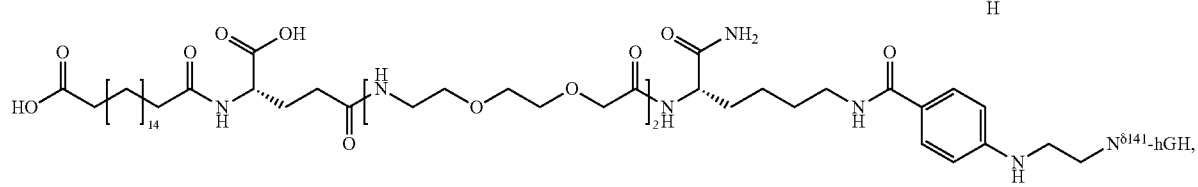

-continued
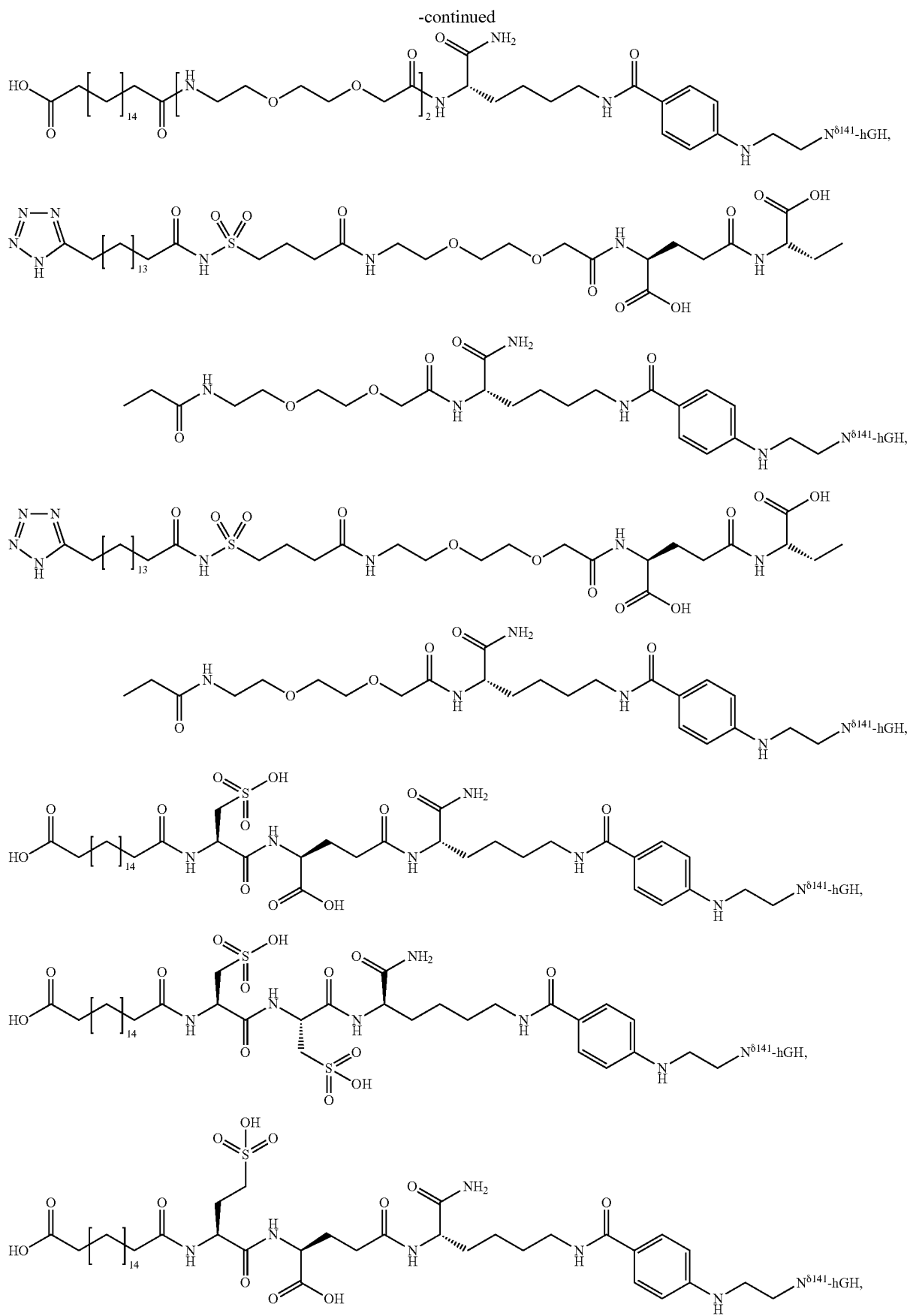

-continued
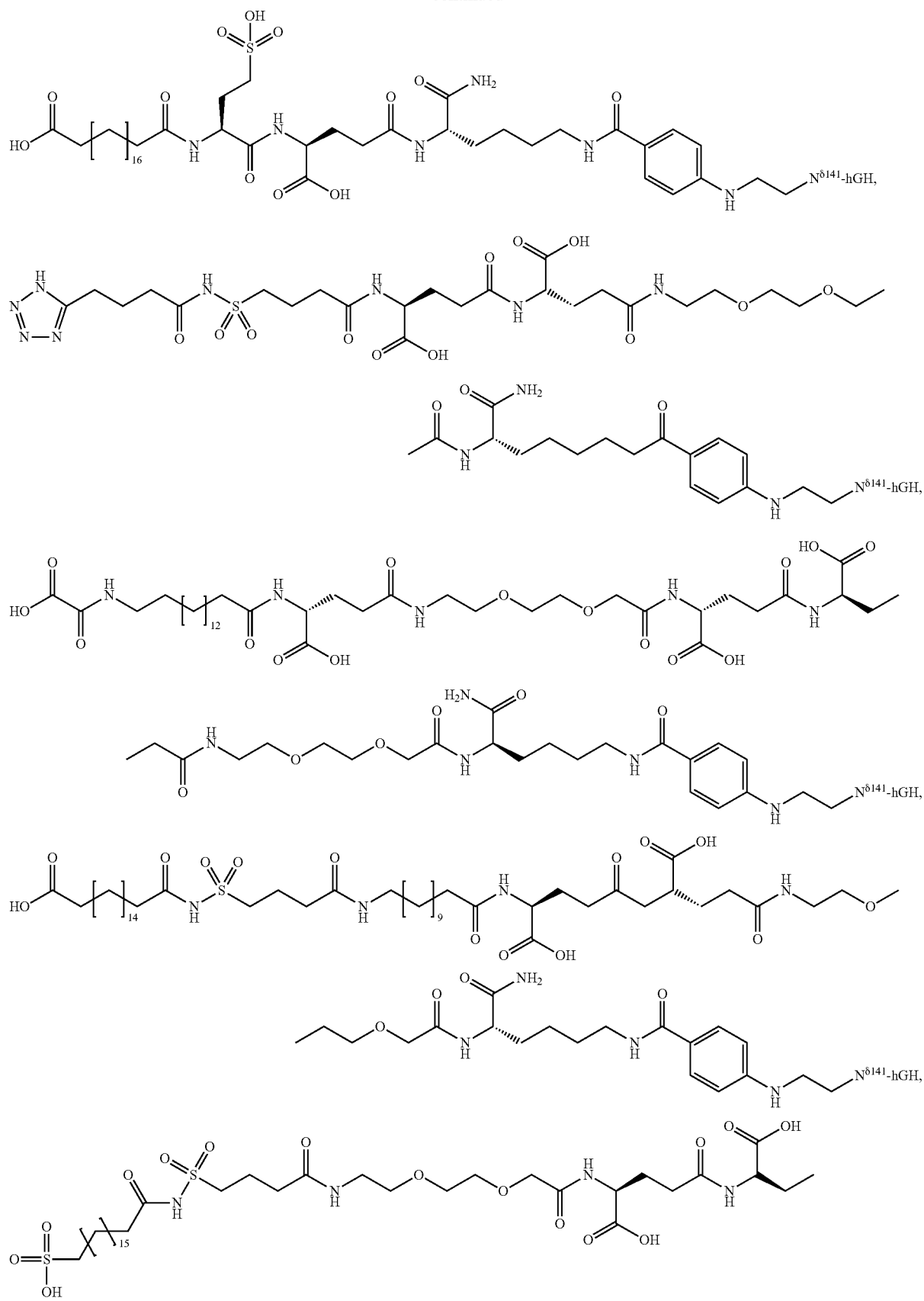

-continued
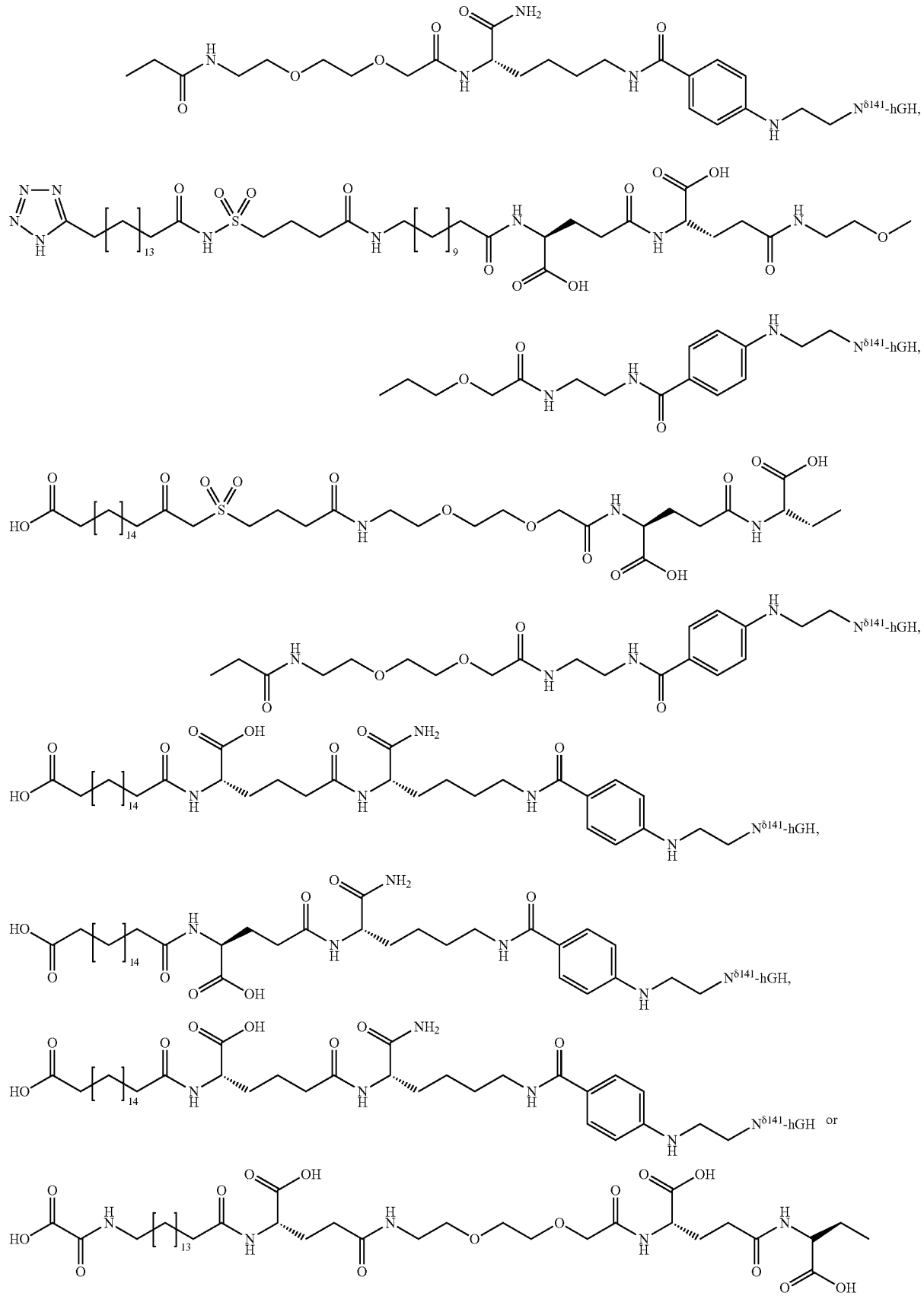

-continued

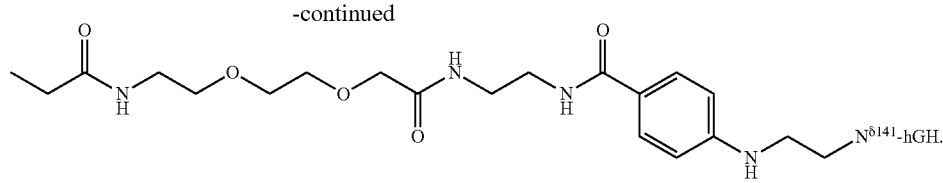

According to a further aspect of the invention there is provided a protein conjugate as defined herein for use in therapy.

In a further aspect the invention relates to a pharmaceutical composition comprising a protein conjugate as defined herein, optionally in combination with a pharmaceutical acceptable excipient.

According to a further aspect of the invention there is provided a protein conjugate which comprises a protein or glycoprotein linked to an albumin binding residue via a hydrophilic spacer, or a pharmaceutically acceptable salt, solvate or prodrug thereof.

According to a further aspect of the invention there is provided a process for preparing a conjugated blood coagulation factor which comprises the steps of reacting a blood coagulation factor as defined herein with a modifier group as defined herein.

The process of the invention results in modified blood coagulation factors having improved pharmacologic properties compared to the un-modified blood coagulation factor. For example, the improved pharmacologic property is selected from the group consisting of increased bioavailability, increased functional in vivo half-life, increased in vivo plasma half-life, reduced immunogenicity, increased protease resistance, increased affinity for albumin, improved affinity for a receptor, increased storage stability, decreased functional in vivo half-life and decreased in vivo plasma half-life.

In one embodiment, the process additionally comprises the addition of a solubilising agent. When the modifier group comprises a fatty acid, the presence of such a solubilising agent provides the advantage of increasing the solubility of the fatty acids in aqueous solution and therefore increasing the effectiveness of the conjugation reaction.

In one embodiment the solubilising agent comprises an optionally substituted cyclodextrin molecule.

Thus, according to a further aspect of the invention, there is provided a process for preparing a conjugated protein or glycoprotein which comprises the steps of reacting a protein or glycoprotein as defined herein with an albumin binder as defined herein in the presence of an optionally substituted cyclodextrin molecule. In one embodiment, the albumin binder comprises a water-insoluble albumin binder and the protein or glycoprotein comprises a water soluble protein or glycoprotein.

Some clot factors (e.g. FVIIa, FIXa, FXa, FIIa) act as proteases in the blood cascade, and it is well known that they are degraded by auto catalysis upon prolonged standing in solution.

Therefore, in addition to the use of a solubilising agent when the modifier comprises a fatty acid, the reaction mixture may additionally contain a reversible blocking agent that inhibits the active site of the protease type clot factors (e.g. FVIIa, FIXa, FXa, FVIIa, etc.).

Therefore, in one embodiment the conjugation between the clot factor and the modifier group is conducted under conditions where the functional site of the clot factor (i.e. the protease site) is blocked by a helper molecule such as a serine protease inhibitor. Preferably, the helper molecule is one, which specifically recognizes the protease site in a reversible manner, and easily can be removed during the subsequent purification steps. For example, benzamidine is a suitable reversible active site inhibitor for FVIIa.

According to a further aspect of the invention there is provided a conjugated protein or glycoprotein obtainable by a process as hereinbefore defined.

According to a further aspect of the invention there is provided a conjugated blood coagulation factor obtainable by a process as hereinbefore defined.

According to a further aspect of the invention there is provided a conjugated blood coagulation factor comprising a blood coagulation factor as defined herein conjugated to a modifier group as defined herein.

Examples of suitable blood coagulation factors include: I (fibrinogen), II (prothrombin), tissue factor, V (proaccelerin), VI, VII, VIII, IX (Christmas factor), X (Stuart-Prower factor), XI (plasma thromboplastin antecedent), XII (Hageman factor), XIII (fibrin-stabilizing factor), von Willebrand factor, prekallikrein, high molecular weight kininogen (HMWK), fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2) and cancer procoagulant.

The invention also encompasses non natural engineered proteins with coagulation activities, such as tissue factor (TF) analogues, TF fusion proteins or TF chimeras having increased affinity for activated platelets, for example, TF-Annexin V, TF-antibody fusion proteins and other TF-fusion proteins including chimeras where the non-TF component increases binding affinity to epitopes expressed on activated platelets. Other examples of proteins with coagulation activity include tissue factor pathway inhibitor antagonists, including anti TFPI antibodies or fragments thereof, as well as thrombin activatable Factor X. Further examples include FVIII-mimicking bispecific MAB.

In one embodiment, the blood coagulation factor is factor VIIa (FVIIa), factor VIII (FVIII) or factor IX (FIX). In a further embodiment, the blood coagulation factor is factor VIIa (FVIIa).

In one embodiment the blood coagulation factor is a factor VIIa (FVIIa), a factor VIII (FVIII) or a factor IX (FIX) analogue. In a further embodiment, the blood coagulation factor is a factor VIIa (FVIIa) analogue.

In one embodiment, the modifier group exhibits a protraction effect by binding to albumin. Albumin, which is present in large amount in blood, binds small molecular fatty acids with micro to nanomolar affinities. If the fatty acid is attached to a larger molecule such as a peptide, the conjugate may bind specifically to albumin present in the blood. Albumin may then function as a large carrier molecule, that by its size protect the peptide from renal clearance or proteolytical attack. The principle is well documented for smaller peptides such as GLP-1 and insulin, but unexpectedly we have found that this type of modifier group also protract larger proteins such as clot factors of similar size to albumin, i.e. proteins that by themself should be large enough to evade renal clearance.

Furthermore, it is surprising that complexes between large proteins of comparable size may be held together by lipophilic forces exerted by modifier groups as defined herein and in particular those comprising a compound of formula I.

Thus as indicated above, the attachment of albumin binders to proteins or peptides has been shown to potentially increase the plasma half life of said proteins or peptides. A class of typical albumin binders are derived from fatty acids, because albumin is capable of binding to highly hydrophobic molecules.

Therefore, compounds having a —$(CH_2)_{12}$— moiety are possible albumin binders in the context of this invention. If an albumin binder, which is defined as above, is attached to a protein or peptide and results in an increased plasma half life of said protein or peptide, it is understood that the albumin binder is a moiety, which increases the plasma half life as described in this invention, contributes to the overall increase of plasma half life by either binding to albumin and/or by other protraction mechanisms such as unspecific binding to lipid layers, etc.

In some embodiments, the preparations of the present invention exhibit a relative bioavailability of at least about 110%, preferably at least about 120%, more preferably at least about 130% and most preferably at least about 140% of the bioavailability of the corresponding un-modified protein. The bioavailability may be measured in any mammalian species, preferably dogs, and the predetermined times used for calculating AUC may encompass different increments from 10 min-8 h. Bioavailability may, for example, be measured in a dog model as follows: The experiment is performed as a four leg cross-over study in 12 Beagle dogs divided in four groups. All animals receive a test preparation A and a reference preparation B at a dose of about 90 μg/kg in a suitable buffer such as glycylglycine buffer (pH 5.5) containing sodium chloride (2.92 mg/ml), calcium chloride dihydrate (1.47 mg/ml), mannitol (30 mg/ml) and polysorbate 80. Blood samples are drawn at 10, 30, and 60 minutes and 2, 3, 4, 6 and 8 hours following the initial administration. Plasma is obtained from the samples and protein is quantified by ELISA.

In one embodiment the modifier group comprises a fatty acid derivative. In a further embodiment, the modifier group comprises a C12, C14, C16, C18 and C20 fatty acid derivative. Without being bound by theory, and as previously mentioned, it is believed that albumin, which is present in large amount in blood, binds small molecular fatty acids with micro to nanomolar affinities. Albumin thereby functions as a carrier molecule, which protects the peptide from renal clearance, neutralising antibodies, receptor mediated clearance or proteolytical attack. Therefore, the present invention provides conjugated blood coagulation factor analogues having increased in vivo plasma half-lives when compared to the corresponding non-conjugated factor.

In one embodiment the modifier group comprises a compound of formula (II):

wherein $R^1$ represents hydrogen, —COOH, tetrazolyl, or —C(=O)—NHS(=O)$_2$—$R^2$;

n is an integer selected from any one of 7, 8, 9, 10, 11, 12, 13, 14, 15, 16, 17, 18, 19, 20, 21, 22, 23, 24, 25; and $R^2$ represents $C_{1-6}$alkyl, phenyl, $C_{1-6}$alkylphenyl, $C_{1-20}$alkyltetrazolyl or $C_{1-20}$alkylcarboxyl.

In one embodiment $R^1$ represents —COOH and n represents an integer selected from 12 to 18 (e.g. 12, 14, 16 or 18).

In one embodiment the modifier group comprises a compound of formula (III):

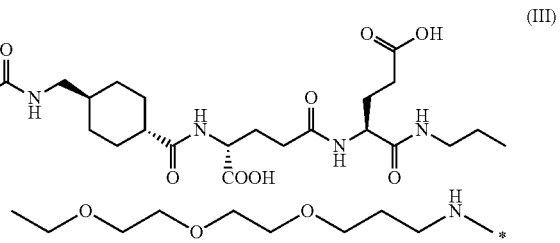

In one embodiment, the modifier group and/or blood coagulation factor additionally comprise a conjugation moiety configured to facilitate conjugation. For example, in one embodiment the modifier group comprises a conjugation moiety selected from a hydroxylamine moiety. Such hydroxylamine moiety will be suitable for conjugation to a variety of functionalized blood coagulation factors (e.g. oxidized derivatives of blood coagulation factors). Such oxidized derivatives of blood coagulation factors may be prepared by direct oxidation (e.g. with periodic acid) when glycan moieties are present on the blood coagulation factor (as described in WO 2008/025856), or suitably excised to allow for oxidation with galactose oxidase (as described in WO 2005/014035). In the event that an exposed galactose or sialic acid residue is not present on the blood coagulation factor they can be galactosylated or sialylated before oxidation using galactosyltransferase or sialyltransferase.

In an alternative embodiment the modifier group comprises a conjugation moiety selected from a maleimide or haloacetate moiety. Such maleimide and haloacetate moieties will be suitable for conjugation to a variety of functionalized blood coagulation factors (e.g. a blood coagulation factor having a free or partly free cysteine residue). It will be appreciated that blood coagulation factors may be engineered to hold a free, or partly free cysteine residue (as described in WO 2006/134174). In certain cases, cysteine residues may be partly blocked by a mixed disulfide to e.g. glutathione. In such cases, it may be removed before conjugation by careful adjustment of the redox potential (GSSG/GSH) in the presence of glutaredoxin. Surface exposed cysteines may also be de-blocked chemically by use of e.g. phosphine based reducing agents such as tricarboxyethylphosphine or tris(3-sulfonato phenyl)phosphine (as described in US2006/0115876). Free thiols on the clot factor may also be reacted with activated sulfides such as thiopyridyl activated sulfides, to form mixed disulfides.

In alternative embodiments the blood coagulation factor may be conjugated to the modifier group using N-terminal serine oxidation followed by e.g. oximation (as described in WO 2006/122982), C-terminal transpeptidation using carboxypeptidase (as described in WO 2005/035553) and suitably designed modifier group derivatives, by use of transglutaminase (as described in WO 2005/070468) or by direct acylation on lysine side chains using e.g. NHS ester or hydrozybenzotriazolyl ester activated modifier groups.

The conjugated blood coagulation factors of the invention and pharmaceutical compositions comprising the conjugated blood coagulation factors may be used in the treatment of diseases alleviated by administration of blood coagulation factors (e.g. FVII(a), FVIII or FIX), such as a bleeding disorder e.g. hemophilia, a blood disease, hemarthrosis, hematomas, mucocutaneous bleeding, inherited blood disease, familial bleeding disorder, familial blood disease or factor replacement therapy. In one embodiment, the disease alleviated by administration of a blood coagulation factor is hemophilia, such as hemophilia B or Christmas disease.

Thus according to a further aspect of the invention there is provided a method of treating hemophilia which comprises administering to a patient a therapeutically effective amount of a conjugated blood coagulation factor as defined hereinbefore.

There is also provided a conjugated blood coagulation factor as defined hereinbefore for use in the treatment of hemophilia.

There is also provided the use of a conjugated blood coagulation factor as defined hereinbefore in the manufacture of a medicament for the treatment of hemophilia.

There is also provided a pharmaceutical composition comprising a conjugated blood coagulation factor as defined hereinbefore for use in the treatment of hemophilia.

It is to be understood, that therapeutic and prophylactic (preventive) regimes represent separate aspects of the present invention. In particular, it should be understood that the present invention provides conjugated blood coagulation factors with increased plasma half-lives which make them desirable for the prophylactic treatment of hemophilia. Such prophylactic treatment of hemophilia constitutes a preferred embodiment of the invention.

According to a further aspect of the invention, there is provided a pharmaceutical formulation comprising a conjugated blood coagulation factor as hereinbefore defined.

The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In one embodiment of the invention the pharmaceutical formulation is an aqueous solution.

In one embodiment the pharmaceutical formulation is a freeze-dried formulation, whereto the physician or the patient adds solvents and/or diluents prior to use.

In one embodiment the pharmaceutical formulation is a dried formulation (e.g. freeze-dried or spray-dried) ready for use without any prior dissolution.

In one embodiment the invention relates to a pharmaceutical formulation comprising an aqueous solution of a conjugated blood coagulation factor of the present invention, and a buffer, wherein said conjugated blood coagulation factor is present in a concentration from 0.1-100 mg/ml, and wherein said formulation has a pH from about 2.0 to about 10.0.

In one embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In one embodiment of the invention the buffer is selected from the group consisting of sodium acetate, sodium carbonate, citrate, glycylglycine, (2-hydroxyethyl)-1-piperazineethanesulfonic acid (HEPES), 3-(N-morpholino)propanesulfonic acid (MOPS); 2-(N-morpholino)ethanesulfonic acid (MES); N-cyclohexyl-3-aminopropanesulfonic acid (CAPS); N-Cyclohexyl-2-aminoethanesulfonic acid (CHES); histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In one embodiment of the invention the formulation further comprises an active site inhibitor.

In one embodiment of the invention the formulation further comprises a pharmaceutically acceptable preservative. In one embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorhexidine, sodium dehydroacetate, chlorocresol, ethyl p-hydroxybenzoate, benzethonium chloride, chlorphenesine (3p-chlorphenoxypropane-1,2-diol) or mixtures thereof.

In one embodiment of the invention the preservative is present in a concentration from 0.1 mg/ml to 20 mg/ml. In one embodiment of the invention the preservative is present in a concentration from 0.1 mg/ml to 5 mg/ml. In one embodiment of the invention the preservative is present in a concentration from 5 mg/ml to 10 mg/ml. In one embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In one embodiment of the invention the formulation further comprises an isotonic agent. In one embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely affect the stabilizing effects achieved using the methods of the invention. In one embodiment, the sugar or sugar alcohol concentration is between about 1 mg/ml and about 150 mg/ml. In one embodiment of the invention the isotonic agent is present in a concentration from 1 mg/ml to 50 mg/ml. In one embodiment of the invention the isotonic agent is present in a concentration from 1 mg/ml to 7 mg/ml. In one embodiment of the invention the isotonic agent is present in a concentration from 8 mg/ml to 24 mg/ml. In one embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a chelating agent. In one embodiment of the invention the chelating agent is selected from salts of ethylenediaminetetraacetic acid (EDTA), citric acid, and aspartic acid, and mixtures thereof. In one embodiment of the invention the chelating agent is present in a concentration from 0.1 mg/ml to 5 mg/ml. In one embodiment of the invention the chelating agent is present in a concentration from 0.1 mg/ml to 2 mg/ml. In one embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In one embodiment of the invention the formulation further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or mixtures thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In one embodiment of the invention the amino acids or amino acid analogues are used in a concentration, which is sufficient to prevent or delay aggregation of the protein.

In one embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or mixtures thereof) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In one embodiment of the invention the formulation further comprises a stabilizer selected from the group of high molecular weight polymers or low molecular compounds. In one embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In one embodiment of the invention the formulation further comprises a surfactant. In one embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)—derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), nonionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, $20^{th}$ edition, 2000.

It is possible that other ingredients may be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a conjugated blood coagulation factor of the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the peptide of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of a peptide of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres and nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the peptide of the present invention in the form of a nasal or pulmonal spray. As a still further option, the pharmaceutical compositions containing the peptide of the present invention can also be adapted to transdermal administration, e.g. by needle-free injection or from a patch, optionally an iontophoretic patch, or transmucosal, e.g. buccal, administration.

The term "stabilized composition" refers to a composition with increased physical stability, increased chemical stability or increased physical and chemical stability.

The term "physical stability" of the protein composition as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition is classified physical unstable with respect to protein aggregation, when it shows visual turbidity in daylight. Alternatively, the turbidity of the composition can be evaluated by simple turbidity measurements well-known to the skilled person. Physical stability of the aqueous protein compositions can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein composition as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

In one embodiment of the invention the pharmaceutical composition comprising the protein conjugate of formula (I) is stable for more than 6 weeks of usage and for more than 3 years of storage.

In another embodiment of the invention the pharmaceutical composition comprising the protein conjugate of formula (I) is stable for more than 4 weeks of usage and for more than 3 years of storage.

In a further embodiment of the invention the pharmaceutical composition comprising the protein conjugate of formula (I) is stable for more than 4 weeks of usage and for more than two years of storage.

In an even further embodiment of the invention the pharmaceutical composition comprising the protein conjugate of formula (I) is stable for more than 2 weeks of usage and for more than two years of storage.

In an even further embodiment of the invention the pharmaceutical composition comprising the protein conjugate of formula (I) is stable for more than 1 week of usage and for more than six months of storage.

General Methods of Preparation

A-W—B— moieties may be attached to proteins enzymatically, or via a chemical reactive group. The choice of reactive group depends on the functionality present on the albumin binder, and the functionality at the protein to modify.

(a) Chemical Reactive Groups

Activated Esters

Activated esters are in general reactive towards amino functions, such as epsilon aminogroups on lysine residues, and the amino group present in the N-terminal of the peptide/protein chain.

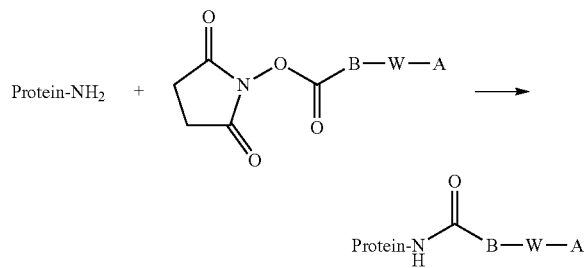

Suitable activated esters include N-hydroxysuccimidyl esters, but other activated esters are known to the skilled person, such as hydroxybenzotriazole esters, 3,4-dihydro-3-hydroxy-4-oxo-1,2,3-benzotriazine, 7-azabenzotriazol-1-yl esters or the like.

In one embodiment, a protein is acylated with a water insoluble albumin binder derivatized as activated ester in aqueous solution in the presence of cyclodextrin or a cyclodextrin derivative.

Coupling to Free Thiol Groups

Proteins may contain free thiol groups that can be reacted with maleimide derivatized albumin binders as depicted below:

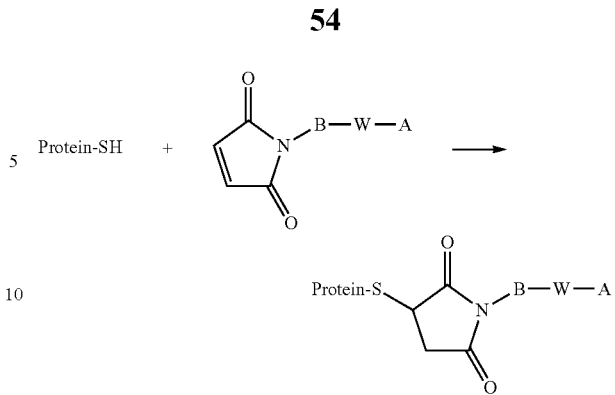

Other thiol reactive groups include haloacetamides, for example iodoacetamides or bromoacetamides, and S-thiopyridyl groups.

In one embodiment, a protein containing a free thiol group is reacted with a water-insoluble albumin binder functionalized with a maleimide group, in aqueous solution in the presence of cyclodextrin or a cyclodextrin derivative.

Coupling to Aldehyde Groups

Aldehyde functionalities can be generated on a protein by mild oxidation of N-terminal serine or threonine residues, or by mild oxidation of glycan moieties on a glycoprotein as described in WO 2008/025856 A2. Albumin binders functionalized with hydroxylamine, hydrazine or hydrazides can subsequently be coupled to the protein as depicted below:

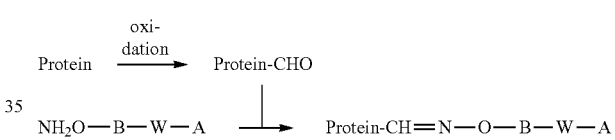

In one embodiment, a protein is oxidized so it contains an aldehyde functionality, and subsequently reacted with a water-insoluble albumin binder functionalized with a hydroxylamine group, in aqueous solution in the presence of cyclodextrin or a cyclodextrin derivative.

(b) Enzymatic Couplings

Albumin binders may be coupled to proteins using enzymes.

Galactose Oxidase

Glycoproteins containing galactose terminals may be oxidized enzymatically using galactose oxidase (EC. 1.1.3.9) as described in WO 2005/014035 A2. Galactose residues on glycoproteins are frequently not directly accessible for enzymatic oxidation, as they are blocked by the presence of sialic acids. In such cases, the sialic acids needs to be removed by the use of sialidases/neuraminidases or by mild acid hydrolysism before oxidation is possible.

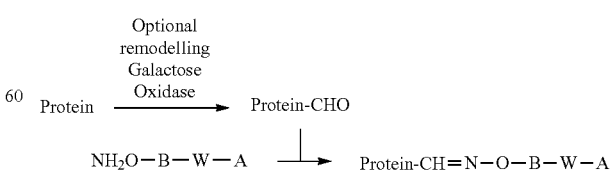

In one embodiment, a glycoprotein is oxidized using galactose oxidase so it contains aldehyde functionality, and subsequently reacted with a water-insoluble albumin binder functionalized with a hydroxylamine group, in aqueous solution in the presence of cyclodextrin or a cyclodextrin derivative.

Transglutaminase

Transglutaminase (E.C.2.3.2.13) is also known as protein-glutamine-γ-glutamyltransferase and catalyses the general reaction

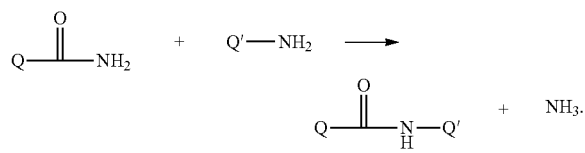

Q-C(O)—NH$_2$ (amine acceptor) may represent a glutamine residue containing peptide or protein and Q'-NH$_2$ (amine donor) represents an amine-containing nucleophile. Alternatively, Q-C(O)—NH$_2$ and Q'-NH$_2$ may represent an amine acceptor and a lysine-containing peptide or protein, respectively. In the present invention, however, Q-C(O)—NH$_2$ represents a glutamine residue containing protein and Q'-NH$_2$ represents an amine-containing nucleophile as indicated above.

Examples of useful transglutaminases include microbial transglutaminases, such as e.g. those from *Streptomyces mobaraense, Streptomyces cinnamoneum* and *Streptomyces griseocarneum* (all disclosed in U.S. Pat. No. 5,156,956, which is incorporated herein by reference), and from *Streptomyces lavendulae* (disclosed in U.S. Pat. No. 5,252,469, which is incorporated herein by reference) and *Streptomyces ladakanum* (JP 2003/199569, which is incorporated herein by reference). It should be noted that members of the former genus *Streptoverticillium* are now included in the genus *Streptomyces* (Kaempfer, *J. Gen. Microbiol.* 137, 1831-1892 (1991)). Other useful microbial transglutaminases have been isolated from *Bacillus subtilis* (disclosed in U.S. Pat. No. 5,731,183, which is incorporated herein by reference) and from various Myxomycetes. Other examples of useful microbial transglutaminases are those disclosed in WO 96/06931 (e.g. transglutaminase from *Bacilus lydicus*) and WO 96/22366, both of which are incorporated herein by reference. Useful non-microbial transglutaminases include guinea-pig liver transglutaminase, and transglutaminases from various marine sources like the flat fish *Pagrus major* (disclosed in EP-0555649, which is incorporated herein by reference), and the Japanese oyster *Crassostrea gigas* (disclosed in U.S. Pat. No. 5,736,356, which is incorporated herein by reference).

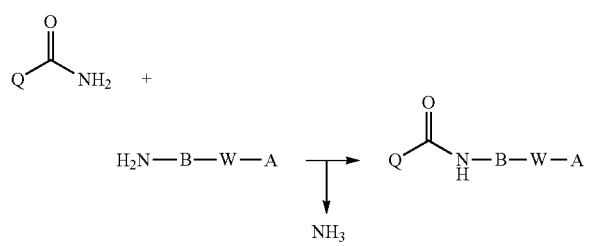

In one embodiment, a protein is treated with transglutaminase and a water-insoluble albumin binder derivatized with an amine handle, in aqueous solution in the presence of cyclodextrin or a cyclodextrin derivative.

Carboxypeptidase Y

Proteins may be modified in their C-terminal by use of carboxypeptidase Y (EC.3.4.16.5), and suitable modified substrates as described in WO 2007/093594. A two step procedure as described by B. Peschke et al. "C-Terminally PEGylated hGH derivatives" *Bioorg. Med. Chem.* 15 (2007) 4382-4395, where C terminal alanine is enzymatically exchanged with N$^\epsilon$-(4-acetylbenzoyl)lysine, followed by reaction with albumin binder derivative A-W—B—ONH$_2$ is shown as illustration:

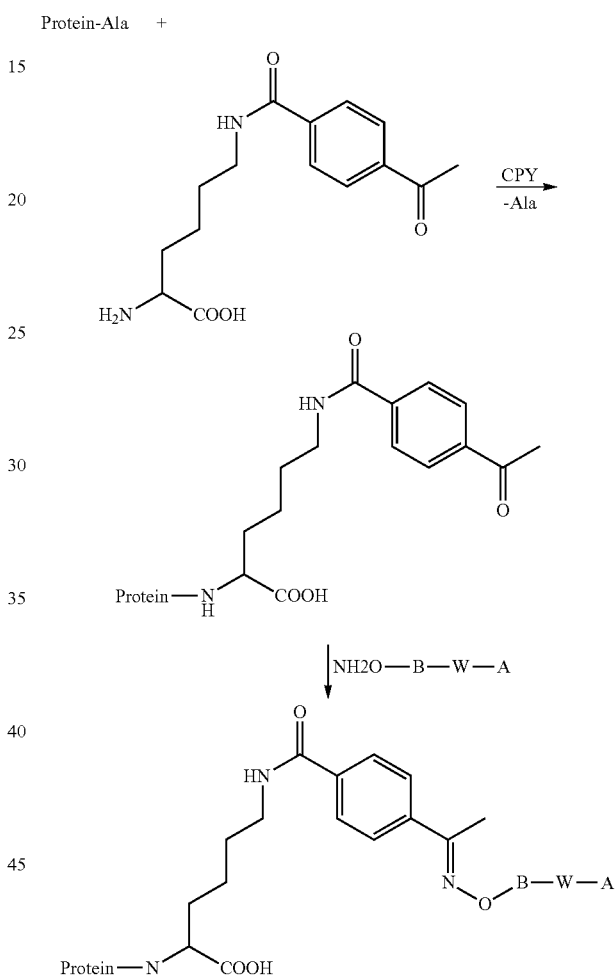

In one embodiment, a protein is treated with carboxypeptidase Y and N$^\epsilon$-(4-acetylbenzoyl)lysine, followed by a water-insoluble albumin binder derivatized with an aminoxy handle, in aqueous solution in the presence of cyclodextrin or a cyclodextrin derivative.

The invention will now be described with reference to the following non-limited Examples:

EXAMPLES

Abbreviations Used amu=atomic mass units
hr(s)=hour(s)
Hz=hertz
L=liter(s)

M=molar
mbar=millibar
mg=milligram(s)
min=minute(s)
mL=milliliter(s)
mM=millimolar
mm=milimeter(s)
mmol=millimole(s)
nmol=nanomole(s)
mol=mole(s)
MW=Molecular weight
N=normal
nm=nanometer(s)
sec=second(s)
ppm=parts per million
ESI=electrospray ionization
i.v.=intravenous
m/z=mass to charge ratio
MS=mass spectrometry
HPLC=high pressure liquid chromatography
RP=reverse phase
HPLC-MS=high pressure liquid chromatography-mass spectrometry
NMR=nuclear magnetic resonance spectroscopy
p.o.=per oral
rt or RT=room temperature
s.c.=subcutaneous
tr=retention time
Boc=tert butyloxycarbonyl
OtBu=tert butyl ester
tBu=tert butyl
Boc-4-ABZ-OH=4-tert-Butoxycarbonylamino-benzoic acid
$CH_3CN$=acetonitrile
DCM=dichloromethane, $CH_2Cl_2$, methylenechloride
DIC=diisopropylcarbdiimide
DIPEA=N,N-diisopropylethylamine
DMF=N,N-dimethylformamide
DMSO=dimethylsulfoxide
DTT=dithiothreitol
EDAC=1-ethyl-3-(3-dimethylaminopropyl)carbodiimide hydrochloride
$Et_2O$=diethyl ether
EtOAc=ethyl acetate
Fmoc=9H-fluoren-9-ylmethoxycarbonyl
Fmoc-Glu-O-t-Bu=N-Fmoc-glutamic acid-1-t-butyl ester
Fmoc-Lys(Mtt)-OH=(S)-6-[(Diphenyl-p-tolyl-methyl)-amino]-2-(9H-fluoren-9-ylmethoxycarbonylamino)-hexanoic acid
Fmoc-OEG-OH=(2[2-(Fmoc-amino)ethoxy]ethoxy)acetic acid
$H_2O$=water
HBTU=2-(1H-Benzotriazol-1-yl-)-1,1,3,3 tetramethyluronium hexafluorophosphate
HOAt=1-Hydroxy-7-azabenzotriazole
HOBt=1-hydroxybenzotriazole
MeCN=acetonitrile
MeOH=methanol
NaCl=sodium chloride
NaOH=sodium hydroxide
NMP=N-methylpyrrolidin-2-one
OEG=(2[2-(amino)ethoxy]ethoxy)acetic acid
OtBu=tert butyl ester
TFA=trifluoroacetic acid
THF=tetrahydrofuran
TIS=triisopropylsilane
Trt=triphenylmethyl
TSTU=O—(N-Succinimidyl)-1,1,3,3-tetramethyl uranium tetrafluoroborate
$CDCl_3$=deuterio chloroform
$CD_3OD$=tetradeuterio methanol
DMSO-$d_6$=hexadeuterio dimethylsulfoxide The TGase used in the examples is microbial transglutaminase from *Streptoverticillium mobaraense* according to U.S. Pat. No. 5,156,956.

The examples also contain the following general methods:

Capillary Electrophoresis

Capillary electrophoresis was carried out using an Agilent Technologies 3DCE system (Agilent Technologies). Data acquisition and signal processing were performed using Agilent Technologies 3DCE ChemStation. The capillary was a 64.5 cm (56.0 cm efficient length) 50 µm i.d. "Extended Light Path Capillary" from Agilent. UV detection was performed at 200 nm (16 nm Bw, Reference 380 nm and 50 nm Bw). The running electrolyte was phosphate buffer 50 mM pH 7 (method A). The capillary was conditioned with 0.1M NaOH for 3 min, then with Milli-Q water for 2 min and with the electrolyte for 3 min. After each run, the capillary was flushed with milli-Q water for 2 min, then with phosphoric acid for 2 min, and with milli-Q water for 2 min. The hydrodynamic injection was done at 50 mbar for 4.0 sec. The voltage was +25 kV. The capillary temperature was 30° C. and the runtime was 10.5 min.

Maldi-Tof Mass Spectrometry

Molecular weights were determined using the Autoflex Maldi-Tof instrument (Bruker). Samples were prepared using alfa-cyano-4-hydroxy-cinnamic acid as matrix.

RP-HPLC

RP-HPLC analysis was performed on a Agilent 1100 system using a Vydac 218TP54 4.6 mm×250 mm 5 µm C-18 silica column (The Separations Group, Hesperia). Detection was by UV at 214 nm, 254 nm, 280 nm and 301 nm. The column was equilibrated with 0.1% trifluoracetic acid/$H_2O$ and the sample was eluted by a suitable gradient of 0 to 90% acetonitrile against 0.1% trifluoracetic acid/$H_2O$.

LC-MS

LC-MS analysis was performed on a PE-Sciex API 100 or 150 mass spectrometer equipped with two Perkin Elmer Series 200 Micropumps, a Perkin Elmer Series 200 autosampler, a Applied Biosystems 785A UV detector and a Sedex 75 Evaporative Light scattering detector. A Waters Xterra 3.0 mm×50 mm 5µ C-18 silica column was eluted at 1.5 ml/min at room temperature. It was equilibrated with 5% MeCN/0.1% TFA/$H_2O$ and eluted for 1.0 min with 5% MeCN/0.1% TFA/$H_2O$ and then with a linear gradient to 90% MeCN/0.1%/0 TFA/$H_2O$ over 7 min. Detection was by UV detection at 214 nm and Evaporative light Scattering. A fraction of the column eluate was introduced into the ionspray interface of a PE-Sciex API 100 mass spectrometer. The mass range 300-2000 amu was scanned every 2 seconds during the run.

Quantification of Protein

Protein concentrations were estimated by measuring absorbance at 280 nm using a NanoDrop ND-1000 UV-spectrophotometer.

Enzymatic Peptide Mapping for Determination of Site(s) of Derivatization

Peptide mapping was performed using Asp-N digestion of the reduced and alkylated protein. First the protein was treated with DTT and iodoacetamide according to standard procedures. The alkylated product was purified using HPLC. Subsequently the alkylated purified product was digested overnight with endoprotease Asp-N (Boehringer) at an enzyme:substrate ratio of 1:100. The digest was HPLC separated using a C-18 column and standard TFA/MeCN buffer system. The resulting peptide map was compared to that of un-derivatized hGH and fractions with different retention times were collected and further analyzed using Maldi-tof mass spectrometry.

SDS Page

SDS poly-acrylamide gel electrophoresis was performed using NuPAGE 4%-12% Bis-Tris gels (Invitrogen NP0321BOX). The gels were silver stained (Invitrogen LC6100) or Coomassie stained (Invitrogen LC6065) and where relevant also stained for PEG with barium iodide as described by M. M. Kurfurst in *Anal. Biochem.* 200(2), 244-248, (1992).

Protein Chromatography

Protein chromatography was performed on an Äkta Explorer chromatographic system and columns from GE Health Care. Anion exchange was done using a Q-Sepharose HP 26/10 column. Starting buffer was 20 mM triethanolamine buffer pH 8.5 and eluting buffer was starting buffer+0.2 M NaCl. The compounds were typically eluted with a gradient of 0-75% eluting buffer over 15 column volumes. Desalting and buffer exchange was performed using a HiPrep 26/10 column.

Example A

Preparation of Conjugated Factor VIIa

Step (a)—Preparation of Albumin Binder (1)

Albumin binder (1) was assembled by conventional solid phase synthesis using 2-chlorotritylchloride resin: Resin was swelled in DCM then added a 10-fold excess of 4,7,10-trioxa-1,13-diamine. After washing, Fmoc-Glu(OtBu)OH, Fmoc-Glu-OtBu, and Fmoc-Thex-OH (transamic acid) was sequential coupled and deprotected using HOBt/DIC and 30% piperidine-DMF. Finally fully unprotected eicosanediacid was coupled in excess using HOAC, DIC, lutidine. The albumin binder was then cleaved from resin using 10% TFA in DCM.

Step (a)—Alternative Procedure

2-Chlorotrityl resin (2.0 g, 2.6 mmol) was swelled in DCM for ½ h. A solution of 4,7,10-trioxa-1,13-diamine in DCM (30 ml) was added. Resin was stirred at rt for 1 h. Resin was washed once with dichloromethane, then added a solution of DIPEA:MeOH:DCM (15 ml:15 ml:20 ml). Resin was shaken for 30 min, then washed trice with DCM. FmocGlu(OtBu) OH, FmocGluOtBu and FmocThexOH were then coupled sequentially by standard peptide chemistry as follows: A 0.5M solution each of Fmoc-AA-OH/DIC/HOBt in NMP (11.7 ml)—was mixed and after 2 min added to the resin. Resin was shaken for 45 min at rt. and then was washed with 5×NMP and 5×DCM. A solution of Ac20/DIPEA/NMP (1:1:5) was added and the resin was stirred at rt for 10 min. The resin was washed (5×NMP and 5×DCM). The resin was then treated with 30% piperidine-NMP for 2×10 min. and finally washed with 5×NMP & 5×DCM. The peptide was then added a 0.25M solution of eicosanediacid (6 eq) containing 0.125M HOAt (3 eq), 0.125M DIC (3 eq) and 0.125M lutidine (3 eq). Resin was shaken at rt for 2 h. Resin was washed with 5×NMP and 8×DCM. Product (1) was cleaved from resin using 10% TFA-DCM for 20 min. The resin was filtrated and the resin was treated once more with 10% TFA-DCM for an additional 20 min. The combined filtrates were collected, and taken to dryness.

Step (b)—Preparation of Maleimide Functionalised Albumin Binder (2)

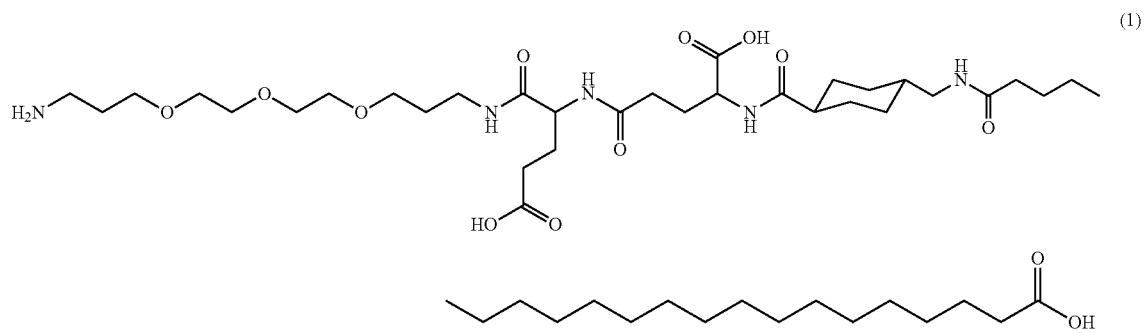

(1)

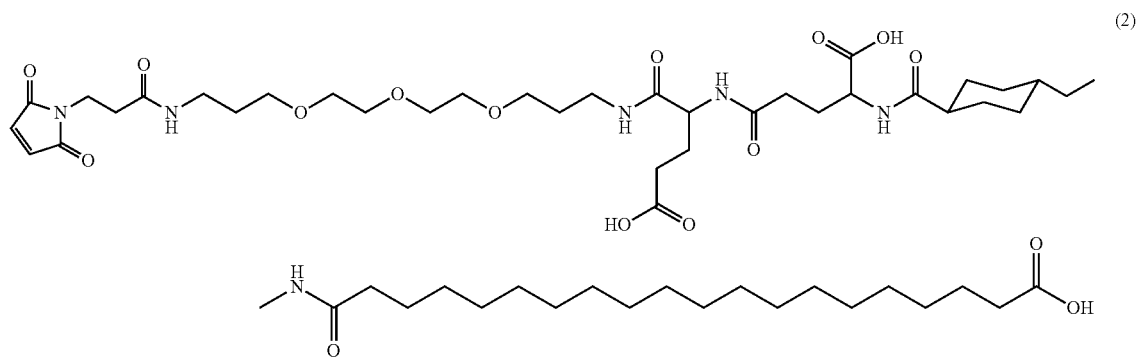

(2)

Albumin binder was further functionalized at the free amino group with a maleimide handle by addition of TSTU activated 3-maleimidopropionic acid in DMF. After final deprotection in 95% TFA-MilliQ, and recrystallization in acetonitril the compound of formula (2) was obtained as a fine white powder.

Step (b)—Alternative Procedure

The product from step (a) above was dissolved in DMF (6 ml), and added TSTU-activated 3 maleimidopropionic acid (premade by reacting TSTU with 3 maleimidopropionic acid in DMF (2 ml) for 45 min) and DIPEA (200 µl). The mixture was stirred at rt for 1 h. The reaction mixture was then taken to dryness. The residue was dissolved in 95% TFA-MilliQ water and stirred at rt for 20 min. The mixture was taken to dryness. The residue was added a minimum of water to precipitate solids. Solids were filtered, and recrystallized in acetonitrile. The crystals were collected and washed extensively with diethyl ether.

Step (c)—Conjugation of Maleimide Functionalised Albumin Binder (2) to FVIIa

C407 Factor VIIa was used for conjugation: scFVIIaC407 in 50 mM Hepes, 100 mM NaCl, 10 mM CaCl2, pH 7.0 was added a solution of (2) in 50 mM Hepes, 100 mM NaCl, 10 mM CaCl2, pH 7.0+5% 2-hydroxyethyl-beta-cyclodextrin and allowed to react at 25° C. for 1 h. Sample was up concentrated and buffer was exchanged into fresh 50 mM Hepes, 100 mM NaCl, 10 mM CaCl2, pH 7.0 and the apoenzyme was allowed to auto-activate overnight at 25° C. Auto activation and selective heavy chain conjugation was confirmed by SDS-PAGE (reducing condition).

Example 1

1. Preparation of Albumin Binders (II)

Tetrazol OEG Linker (IIa):

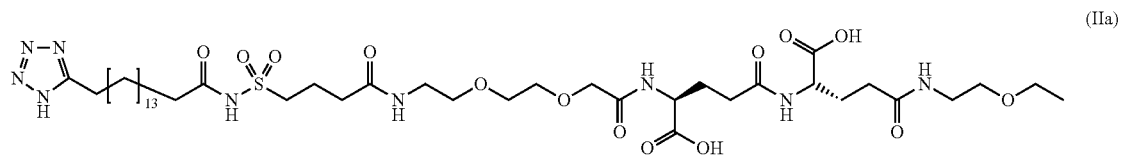

(IIa)

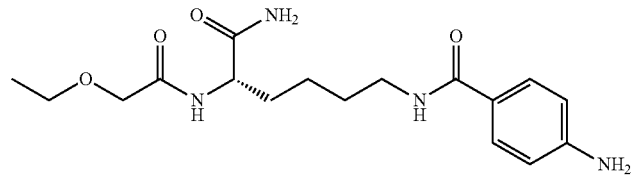

The tetrazole OEG linker (IIa) was synthesised according to scheme 1.

Scheme 1.
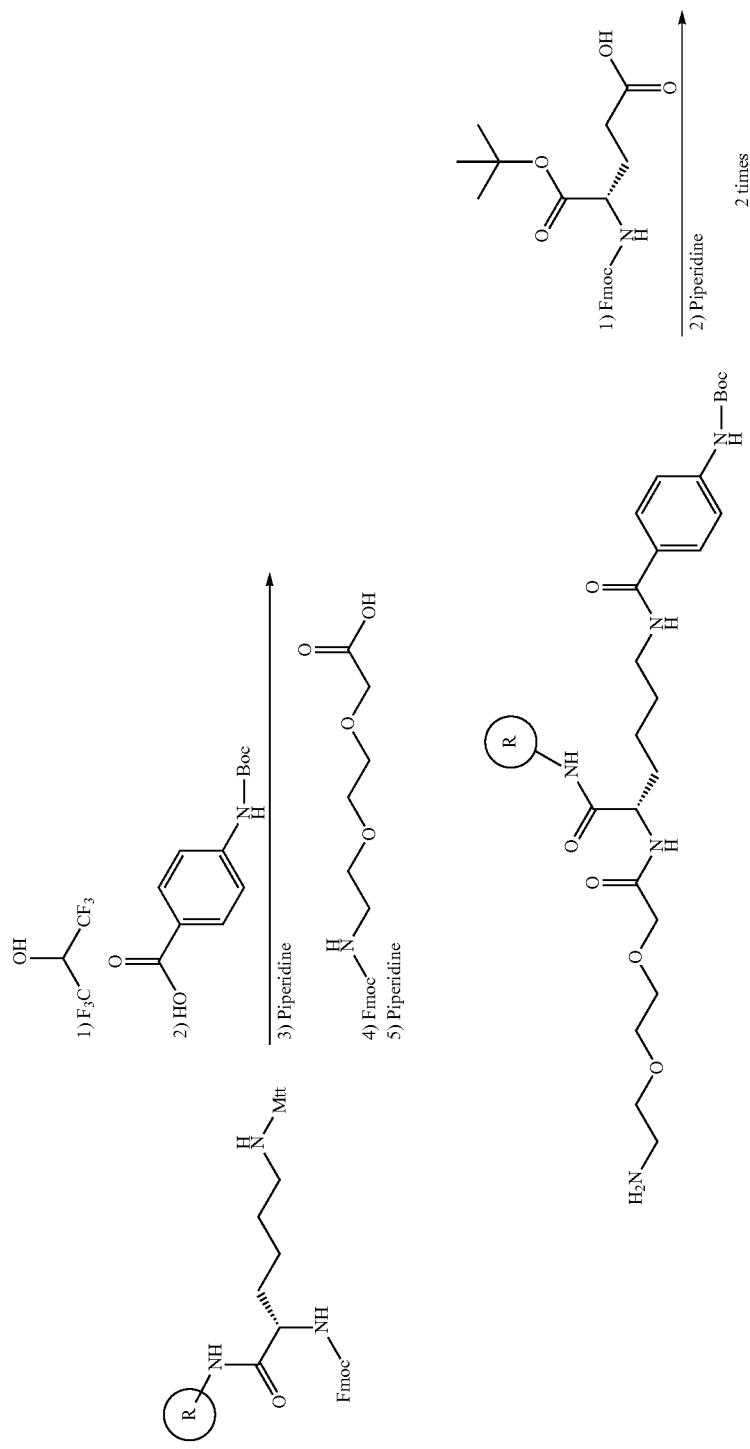

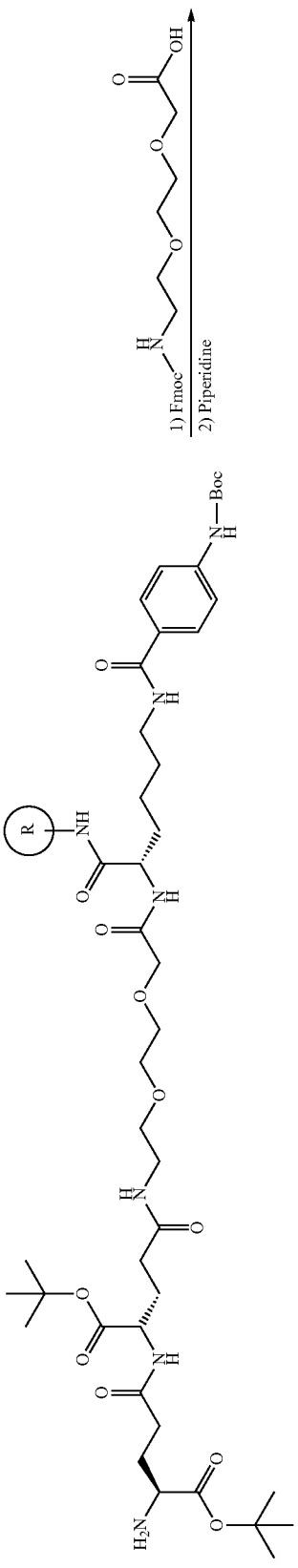
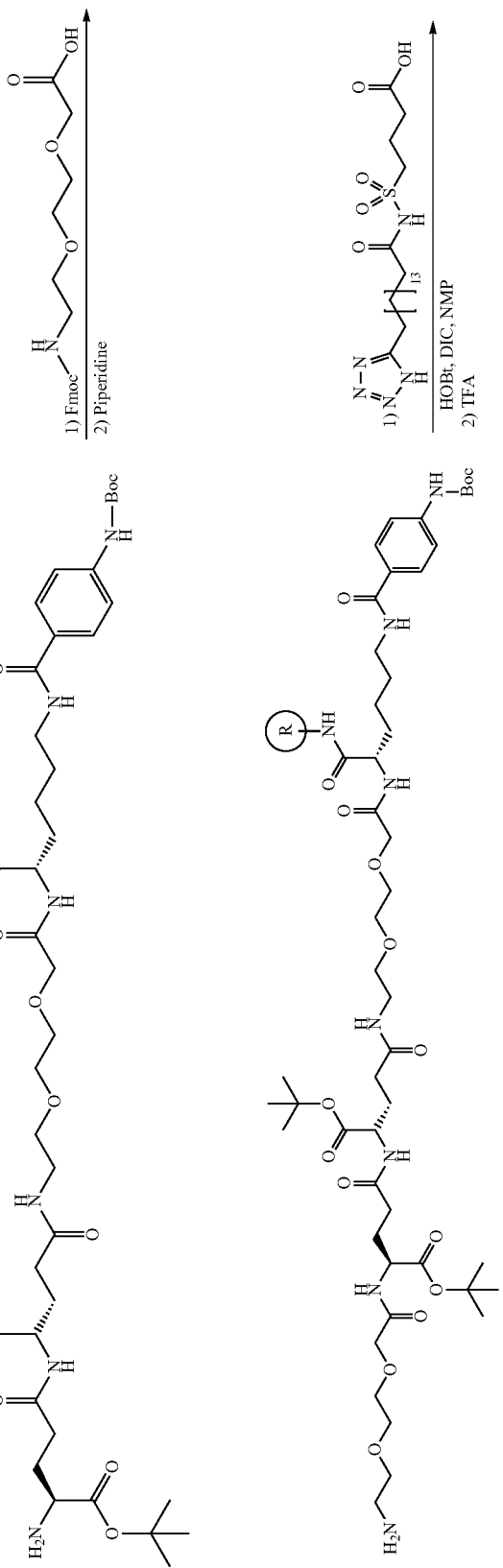
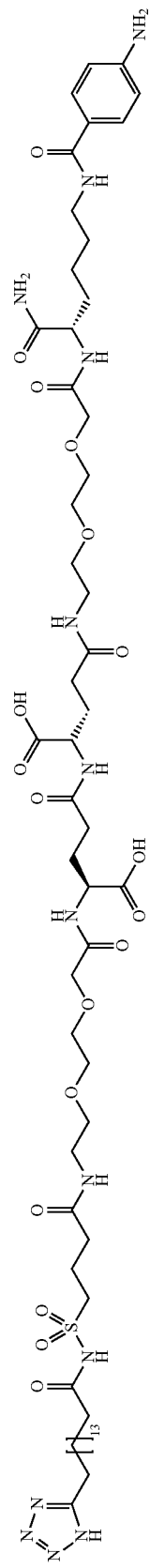

2 g of Rink-Amide-Resin (2 g, 0.6 mMol/g) was weighed into a flask. The resin was swelled with NMP (3×30 mL) for 2 hrs.

Removal of the Fmoc-group: The resin was shaken with 25% piperidine in NMP (30 mL) for 10 min. The resin was drained and treated with 25% piperidine in NMP (30 mL) for 1 hour followed by draining and wash with NMP (6×30 mL). Fmoc-Lys(Mtt)-OH and HOBT were weighed into a flask, dissolved in bromo phenol blue in NMP (30 mL, 0.5 mM). This solution was added to the drained resin above followed by addition of DIC. The reaction was shaken at ambient temperature for 21 hrs. The resin was drained and washed with NMP (6×30 mL) followed by washing with DCM (3×30 mL).

The resin was treated with hexafluorisopropanol (20 mL) for 10 min. Shaken for 10 min. The resin was drained and washed with DCM (3×30 mL). The resin was treated with hexafluorisopropanol (20 mL) for 10 min again. Shaken for 10 min. The resin was drained and washed with DCM (3×30 mL) followed by drained and washed with NMP (3×30 mL).

Boc-4-ABZ-OH and HOBT were weighed into a flask, dissolved in bromo phenol blue in NMP (30 mL, 0.5 mM). This solution was added to the drained resin above followed by addition of DIC. The reaction was shaken at ambient temperature. The resin was drained and washed with NMP (6×30 mL). Removel of the Fmoc-group: The resin was shaken with 25% piperidine in NMP (10 mL) for 10 min. The resin was drained and treated with 25% piperidine in NMP (10 mL) for 1 hour followed by draining and wash with NMP (6×15 mL).

Fmoc-OEG-OH and HOBT were weighed into a flask, dissolved in brom phenol blue in NMP (15 mL, 0.5 mM). This solution was added to the drained resin followed by addition of DIC. The reaction was shaken at ambient temperature for 23 hrs. The resin was drained and washed with NMP (6×15 mL).

Removal of the Fmoc-group: The resin was shaken with 25% piperidine in NMP (10 mL) for 10 min. The resin was drained and treated with 25% piperidine in NMP (10 mL) for 1 hour followed by draining and wash with NMP (6×15 mL).

Fmoc-Glu-O-t-Bu and HOBT were weighed into a flask, dissolved in bromo phenol blue in NMP (15 mL, 0.5 mM). This solution was added to the drained resin followed by addition of DIC. The reaction was shaken at ambient temperature for 18 hrs. The resin was drained and wash with NMP (6×15 mL).

Removal of the Fmoc-group: The resin was shaken with 25% piperidine in NMP (10 mL) for 10 min. The resin was drained and treated with 25% piperidine in NMP (10 mL) for 1 hour followed by draining and washing with NMP (6×15 mL).

Fmoc-OEG-OH and HOBT were weighed into a flask, dissolved in bromo phenol blue in NMP (15 mL, 0.5 mM). This solution was added to the drained resin followed by addition of DIC. The reaction was shaken at ambient temperature. The resin was drained and washed with NMP (6×15 mL).

Removal of the Fmoc-group: The resin was shaken with 25% piperidine in NMP (10 mL) for 10 min. The resin was drained and treated with 25% piperidine in NMP (10 mL) for 1 hour followed by draining and washing with NMP (6×15 mL).

4-(16-1H-Tetrazol-5-yl-hexadecanoylsulfamoyl)-butyric acid and HOBT were weighed into a flask, dissolved in bromo phenol blue in NMP (15 mL, 0.5 mM). This solution was added to the drained resin followed by the addition of DIC. The reaction was shaken at ambient temperature for 21 hrs. The resin was drained and washed with NMP (6×15 mL NMP) followed by draining and wash with DCM (6×15 mL).

The resin was cleaved with a mixture of 95% TFA in water (10 mL)+DCM (0.25 mL) and TIPS (0.25 mL). The resin was shaken for 2 hours at ambient temperature. Filtered down into cold diethyl ether (75 mL). The resulting precipitate was isolated by centrifugation followed by washing with diethyl ether (3×) and dried in vacuum for 48 hours affording crude 300 mg of the title compound.

TOF-MS: Rt=4.7 min, mass 1268.71

Crude title compound was purified on prep-HPLC (GILSON). T2145-10; 30->80% MeCN. Pooled fractions were evaporated to dryness on rotavap and the residue dissolved in H$_2$O/MeCN 1:1 and freezedried over night affording 170 mg of the title compound.

Example 2

In a similar way as described in Example 1 above the following compound was prepared using FMOC-Lys(Mtt)-OH and Wang Resin.

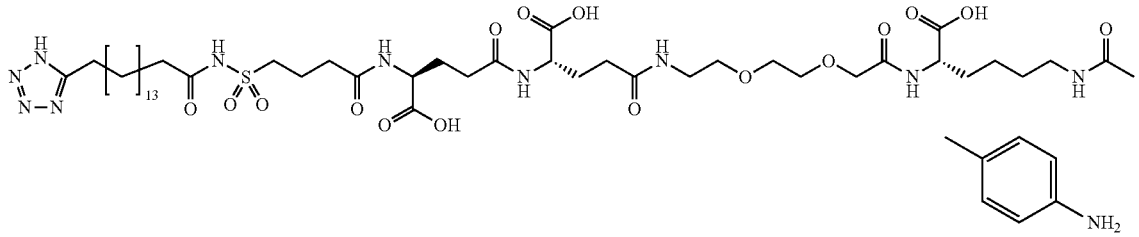

TOF-MS: mass 1124.33

Example 3

In a similar way as described in Example 1 above and depicted below the following compound was prepared using Boc-Gly-PAM resin as starting material.

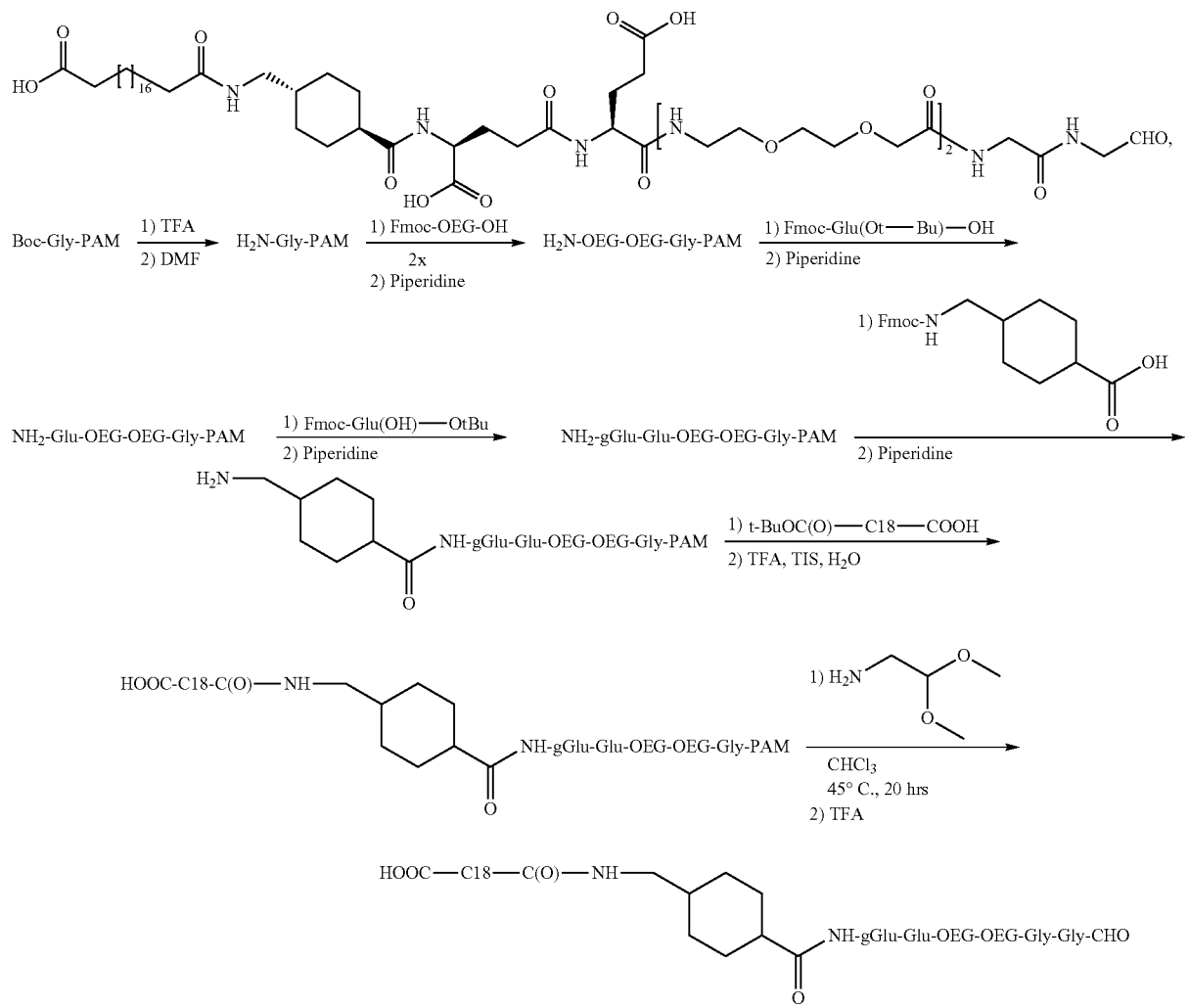
TOF-MS: mass 1128.38
Example 4
In a similar way as described in Example 1 above the following compound was prepared using FMOC-Lys(Mtt)-OH and Rink amid resin.
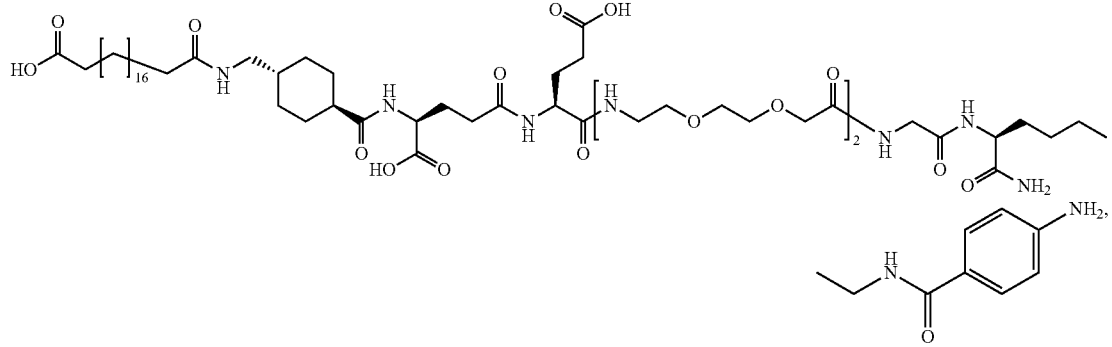
TOF-MS: mass 1333.64

Example 5

In a similar way as described in Example 1 above the following compound was prepared using FMOC-Lys(Mtt)-OH and Rink amid resin.

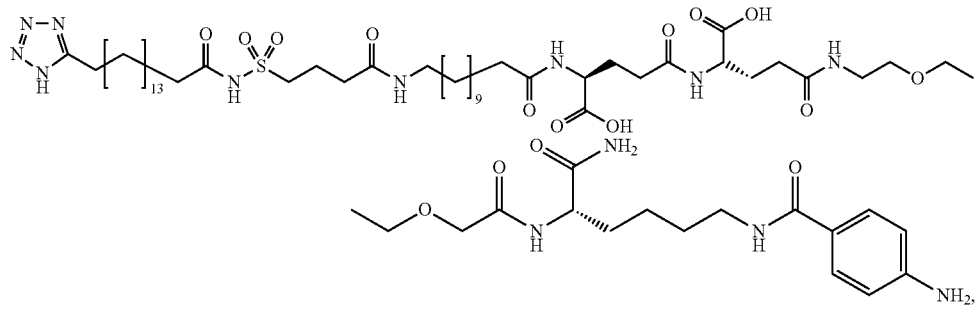

TOF-MS: mass 1320.67

Example 6

In a similar way as described in Example 1 above the following compound was prepared using FMOC-Lys(Mtt)-OH and Rink amid resin.

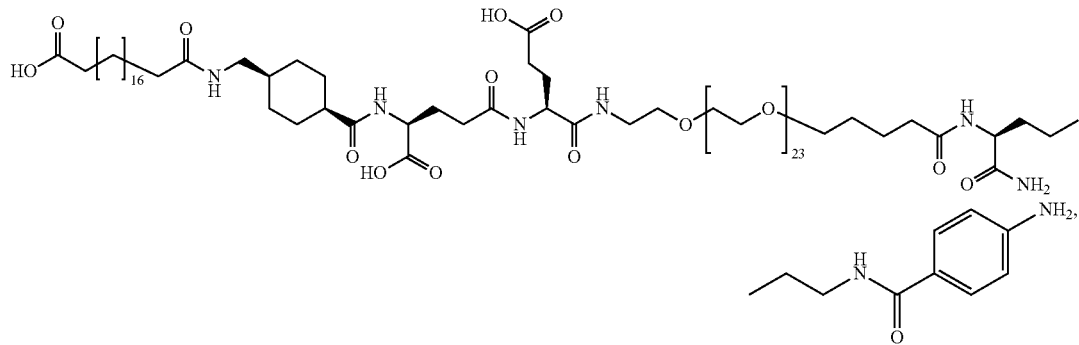

TOF-MS: mass 2114.64

Example 7

In a similar way as described in Example 1 above the following compound was prepared using FMOC-Lys(Mtt)-OH and Rink amid resin.

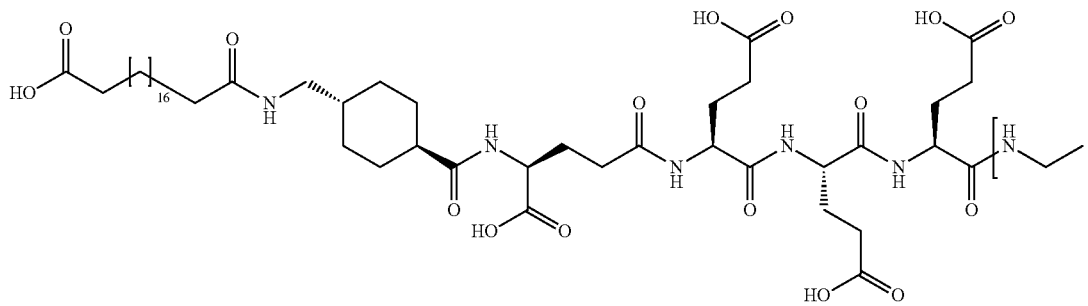

-continued

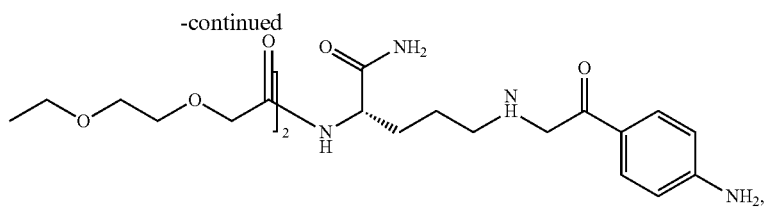

TOF-MS: mass 1534.82

Example 8

In a similar way as described in Example 1 above the following compound was prepared using FMOC-Lys(Mtt)-OH and Rink amid resin.

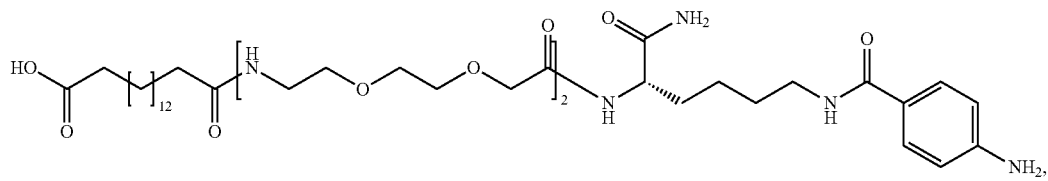

TOF-MS: mass 823.05

Example 9

In a similar way as described in Example 1 above the following compound was prepared using FMOC-Lys(Mtt)-OH and Wang Resin.

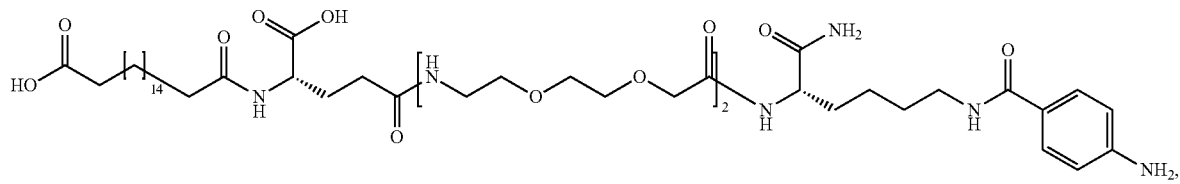

TOF-MS: mass 980.22

Example 10

In a similar way as described in Example 1 above the following compound was prepared using FMOC-Lys(Mtt)-OH and Rink amid resin.

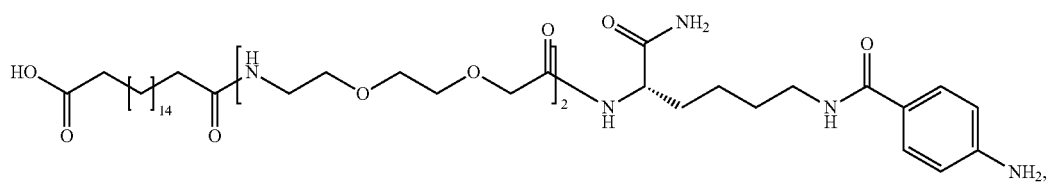

TOF-MS: mass 851.10

Example 11

In a similar way as described in Example 1 above the following compound was prepared using FMOC-Lys(Mtt)-OH and Rink amid resin.

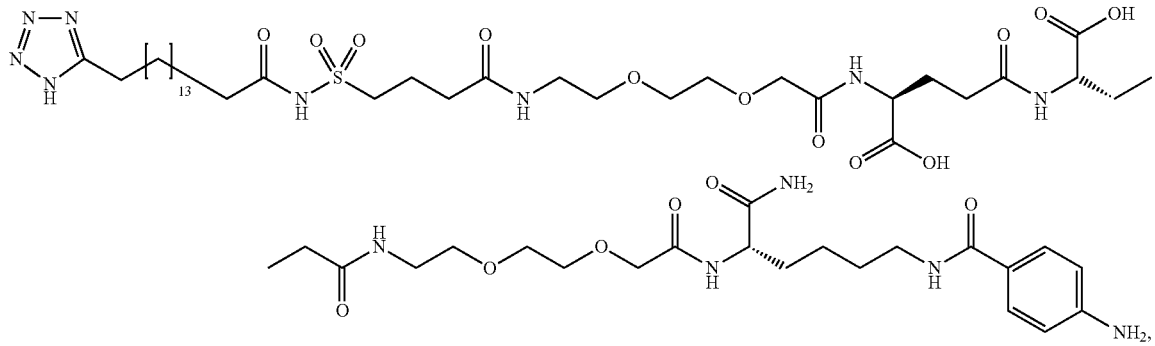

TOF-MS: mass 1258.51

Example 12

In a similar way as described in Example 1 above the following compound was Prepared using FMOC-Lys(Mtt)-OH and Wang Resin.

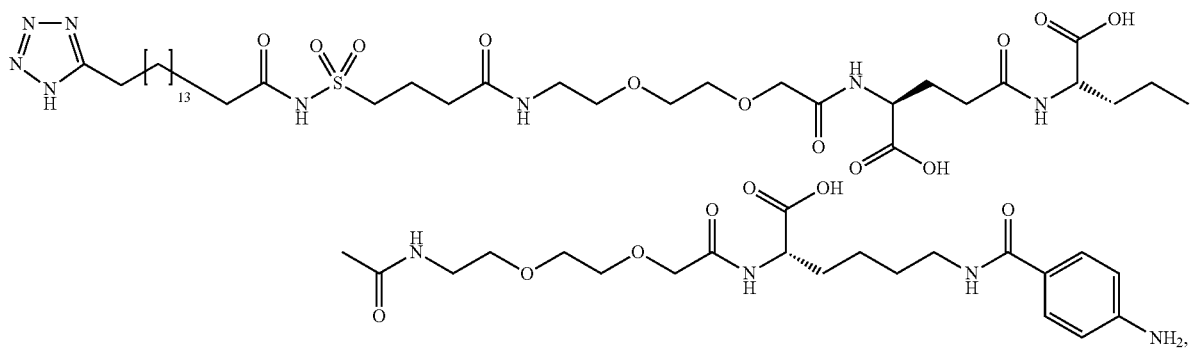

TOF-MS: mass 1269.49

Example 13

In a similar way as described in Example 1 above the following compound was prepared using FMOC-Lys(Mtt)-OH and Rink amid resin.

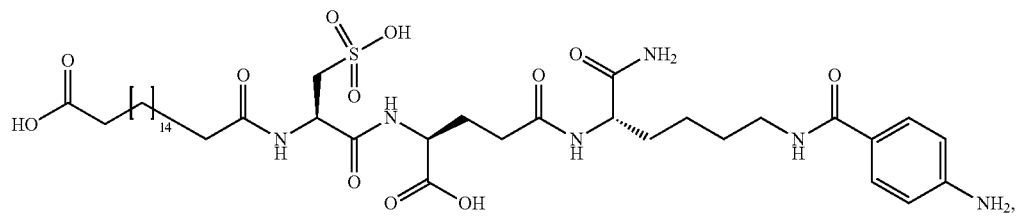

TOF-MS: mass 841.04

Example 14

In a similar way as described in Example 1 above the following compound was prepared using FMOC-Lys(Mtt)-OH and Rink amid resin.

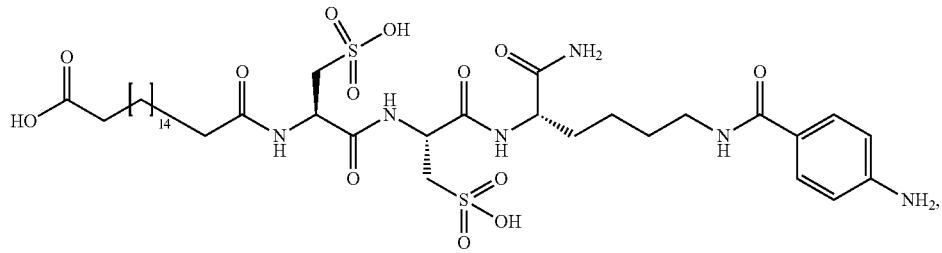

TOF-MS: mass 863.07

Example 15

In a similar way as described in Example 1 above the following compound was prepared using FMOC-Lys(Mtt)-OH and Rink amid resin.

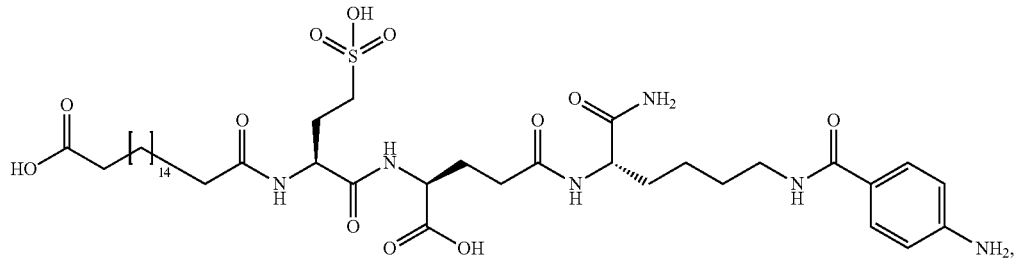

TOF-MS: mass 855.07

Example 16

In a similar way as described in Example 1 above the following compound was prepared using FMOC-Lys(Mtt)-OH and Rink amid resin.

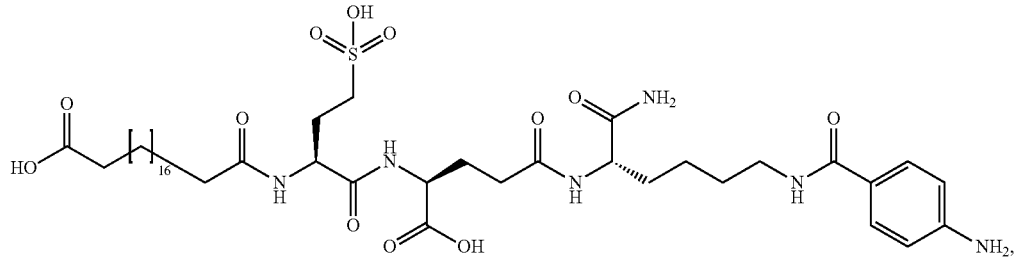

TOF-MS: mass 883.12

Example 17

In a similar way as described in Example 1 above the following compound was prepared using FMOC-Lys(Mtt)-OH and Rink amid resin.

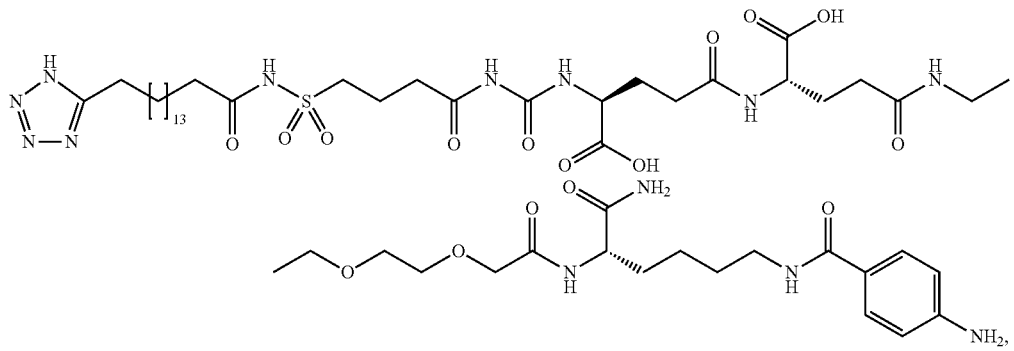

TOF-MS: mass 1123.35

Example 18

In a similar way as described in Example 1 above the following compound was prepared using FMOC-Lys(Mtt)-OH and Rink amid resin.

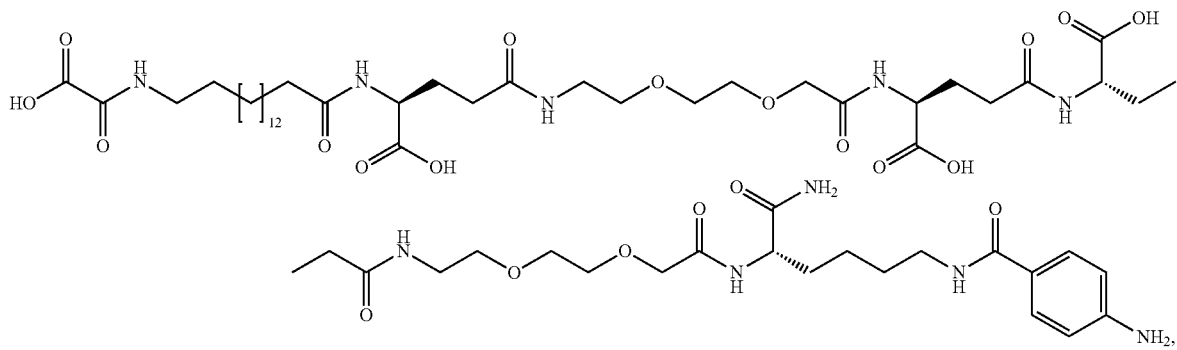

TOF-MS: Rt=4.7 min, mass 1267.45

Example 19

In a similar way as described in Example 1 above the following compound was prepared using FMOC-Lys(Mtt)-OH and Rink amid resin.

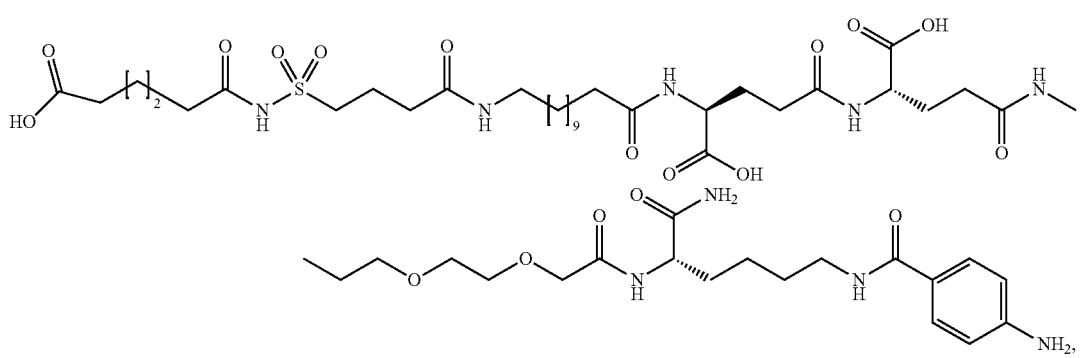

TOF-MS: mass 1310.67

Example 20

In a similar way as described in Example 1 above the following compound was prepared using FMOC-Lys(Mtt)-OH and Rink amid resin.

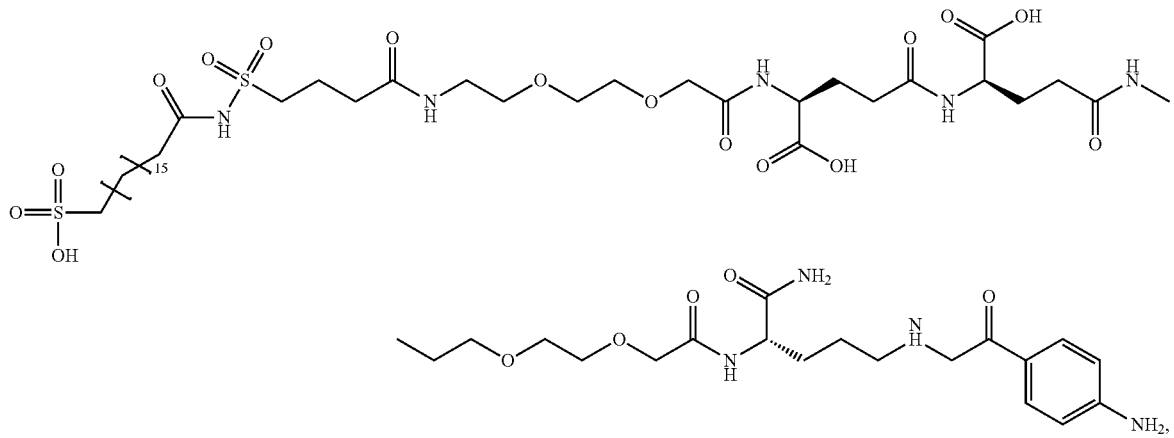

TOF-MS: mass 1308.58

Example 21

In a similar way as described in Example 1 above the following compound was prepared using FMOC-Glu(ODmab)-OH and 2-chlorotrityl chloride resine.

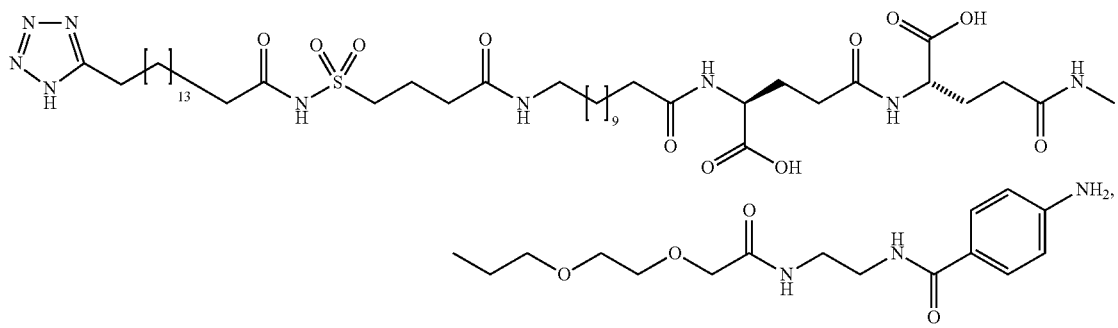

TOF-MS: mass 1235.56

Example 22

In a similar way as described in Example 1 above the following compound was prepared using FMOC-Glu(ODmab)-OH and 2-chlorotrityl chloride resine.

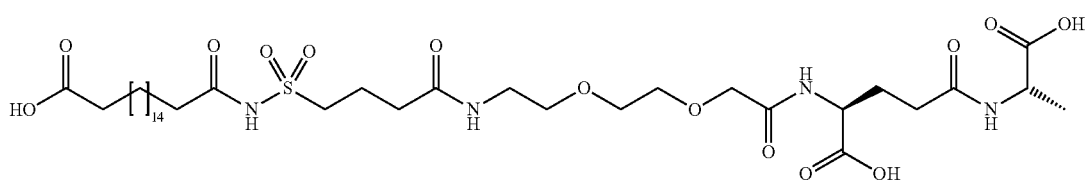

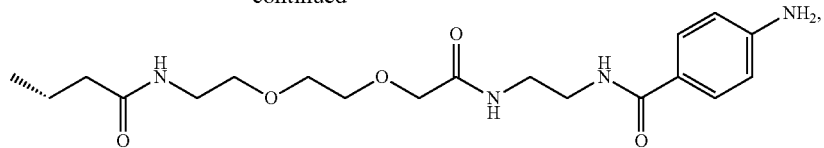

TOF-MS: mass 1173.40

Example 23

In a similar way as described in Example 1 above the following compound was prepared using FMOC-Lys(Mtt)-OH and Rink amid resin.

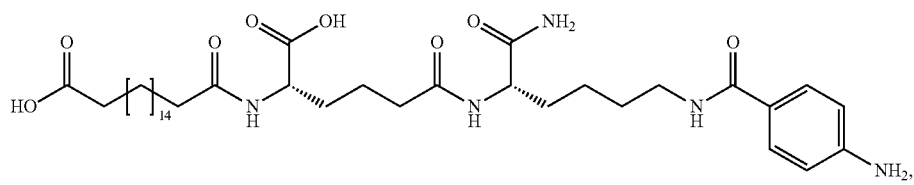

TOF-MS: mass 703.93

Example 24

In a similar way as described in Example 1 above the following compound was prepared using FMOC-Lys(Mtt)-OH and Rink amid resin.

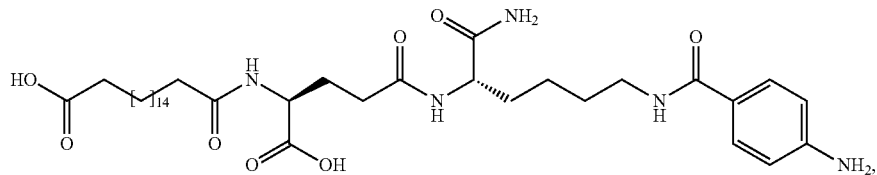

TOF-MS: mass 689.90

Example 25

In a similar way as described in Example 1 above the following compound was prepared using FMOC-Glu(ODmab)-OH and 2-chlorotrityl chloride resine.

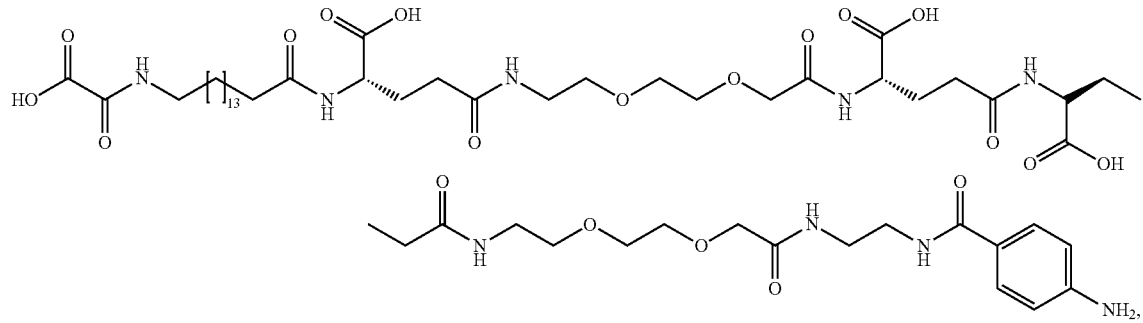

TOF-MS: mass 1182.34

85

Preparation of GH Albumin Binder Compounds:

Example 26

1. Coupling of Transaminated and Oxidised GH Compound (I) with an Albumine Binder (II)

The following solution was prepared:
Buffer A: Triethanolamine (119 mg, 0.8 mmol) was dissolved in water (40 mL) and pH adjusted to 8.5.
Buffer B: 20 mM Triethanolamine; 0.2 M NaCl.

(A) Transamination of hGH (III) with 1,3-diamino-2-propanol

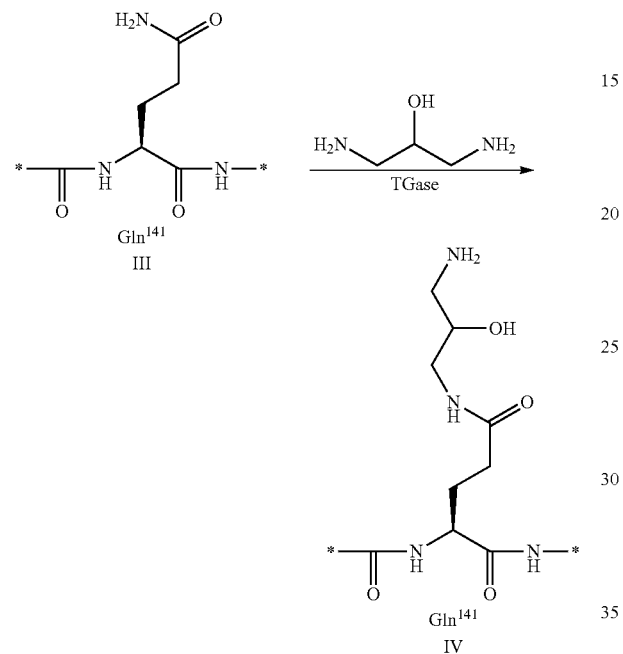

The following solutions were prepared:
hGH (8.64 g) as powder was dissolved in Bufer A (500 mL) with stirring. To this solution was added slowely a mixture of DAP (8.1 g) in Buffer A (50 mL). pH of the resulting mixture was ajusted to 8.5 by addition of aq. HCl. TGase (2.8 mL, 1.3 mg/mL)) was added while mixing. The final mixture was stirred overnight at RT.

The reaction mixture was diluted with buffer A (1.2 L) and the product (IV) was purified by ion exchange chromatography. 100 ml/min-200 ml/frac.

Step Buffer B 40%–gradient 40-100% Buffer B over 15 CV=225 min.

(B) Oxidation of Transaminated hGH (IV)

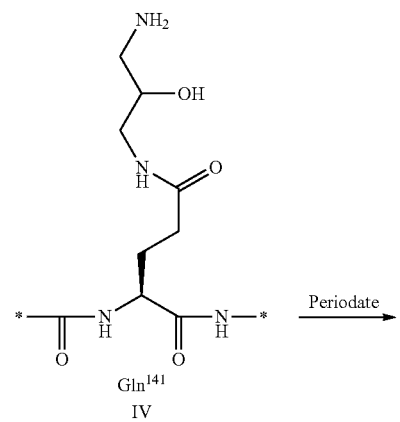

86

-continued

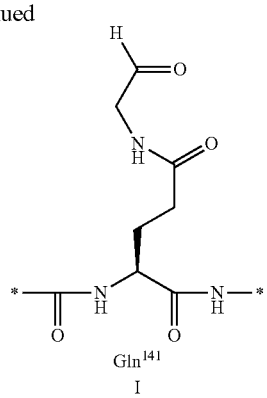

The following solutions were prepared:
Buffer A: Triethanolamine (119 mg, 0.8 mmol) was dissolved in water (40 mL) and pH adjusted to 8.5.
Buffer B: 3-methylthio-1-propanol (725 mg, 7.1 mmol) was dissolved in Buffer A (10 mL).
Buffer C: HEPES (5.96 g) was dissolved in water (1.0 L) and pH adjusted to 7.0
Periodate: $NaIO_4$ (48.1 mg, 0.225 mmol) was dissolved in water (1.0 mL).

To a solution of IV (10 mg, 0.5 μmol) was added Buffer B (0.2 mL) followed by the periodate solution (0.03 mL). After 20 min's of cold incubation the mixture is dialyzed 4 times with buffer C. The residue was concentrated to 1 mL.

(C) Reductive Amination of (I) with Albumin Binder (II)

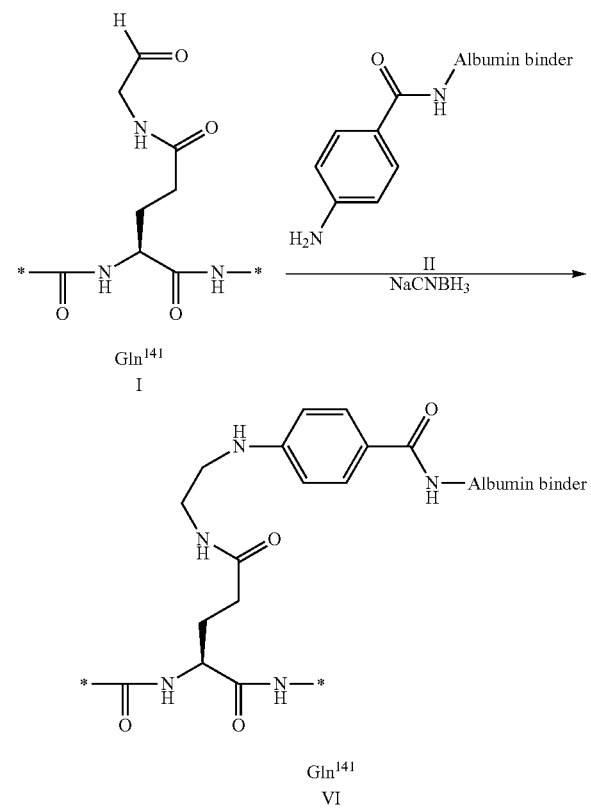

Albumin binder (II) was obtained as described in example 1 through 26. The final solution from (B) (1 mL, 10 mg, 0.45 μmol (I)) was mixed with an albumine binder (II) solution (2 mL, 10 mg, 0.3 μmol) in 25 mM HEPES buffer pH 7.0 and the resulting mixture was slowly rotated at room temperature for 1 hr. After 1 hr NaCNBH₃ (100 μL of a solution of NaCNBH₃ (20 mg) in water (0.5 mL)) was added portionwise. The mixture was kept at room temperature in the dark for 18-24 hours.

The mixture was diluted with 1M tris solution to a final concentration of 50 mM pH 7.5 and applied to an ion exchange column. Product (VI) was obtained by elution of the column with a gradient of NaCl.

Example 27

In a similar way as described in Example 26 above the following compound was prepared using albumin binder from Example 2.

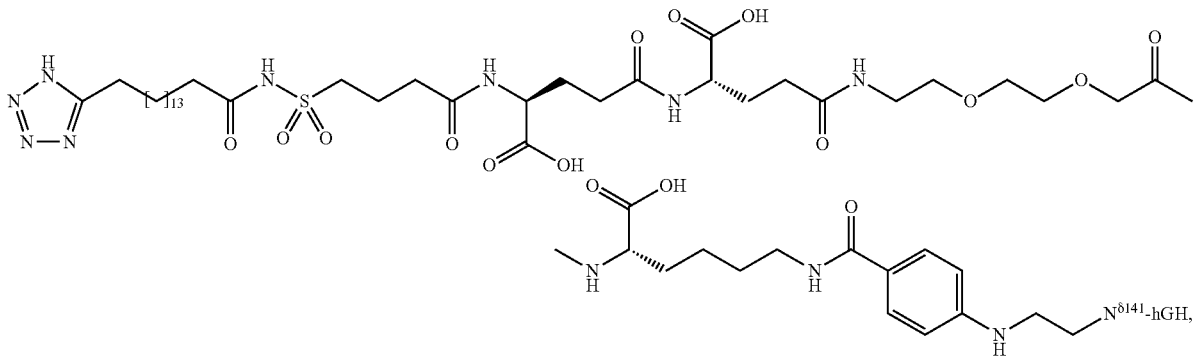

TOF-MS: mass 23.473, 81

Example 28

In a similar way as described in Example 26 above the following compound was prepared using albumin binder from Example 4.

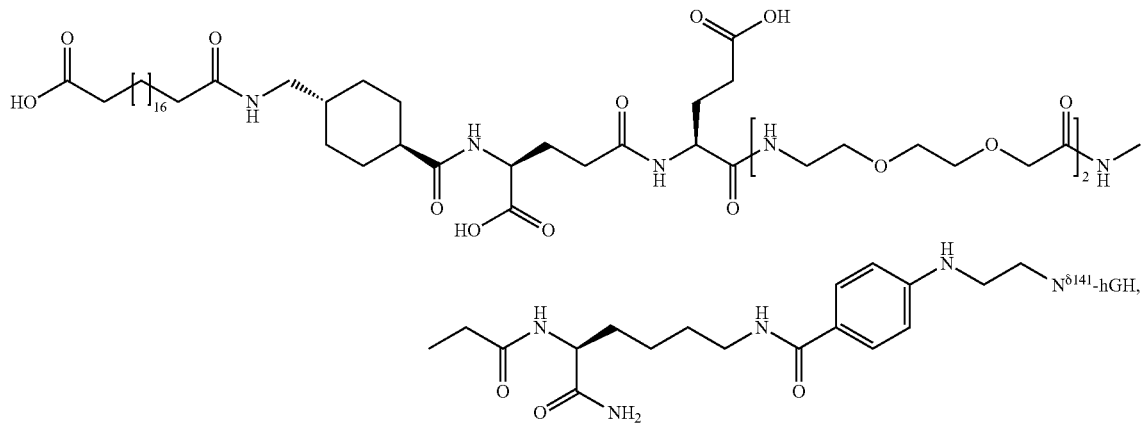

TOF-MS: mass 23.428

Example 29

In a similar way as described in Example 26 above the following compound was prepared using albumin binder from Example 5.

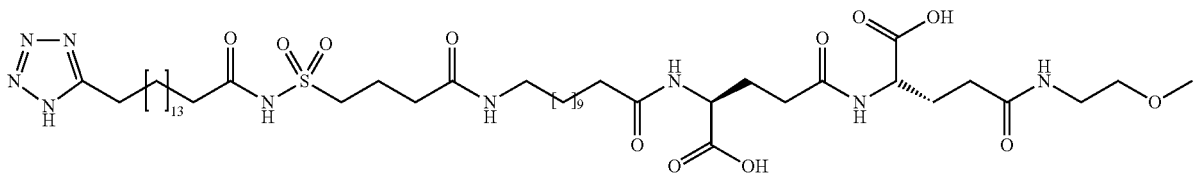

-continued
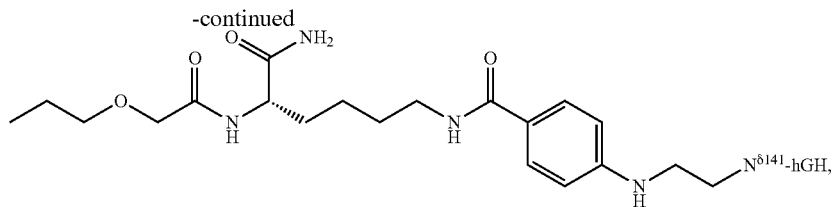
TOF-MS: mass 23.472, 40
Example 30
In a similar way as described in Example 26 above the following compound was prepared using albumin binder from Example 6.
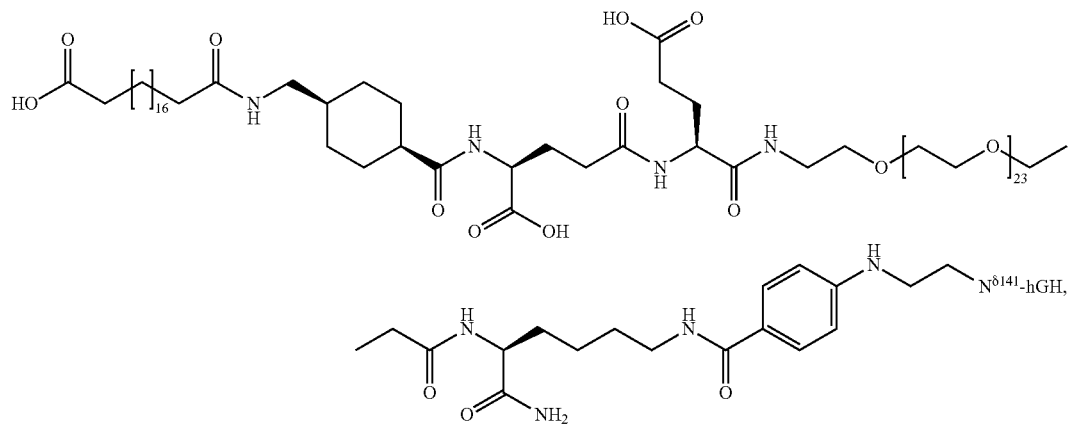
TOF-MS: mass 24.265, 71
Example 31
In a similar way as described in Example 26 above the following compound was prepared using albumin binder from Example 7.
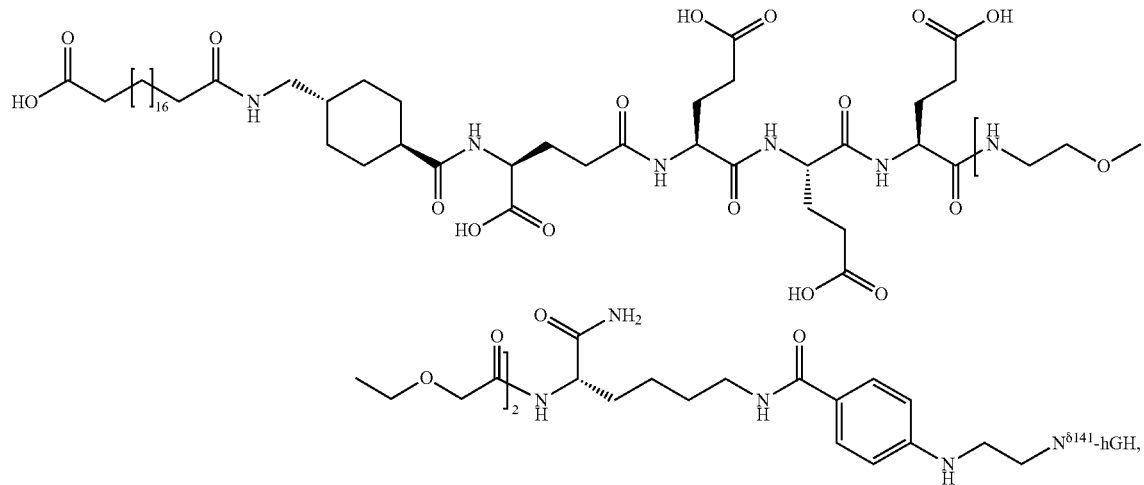
TOF-MS: mass 23.686, 83

Example 32

In a similar way as described in Example 26 above the following compound was prepared using albumin binder from Example 8.

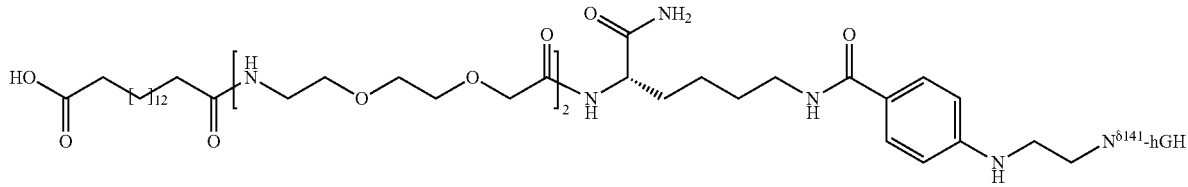

TOF-MS: mass 22.974, 75

Example 33

In a similar way as described in Example 26 above the following compound was prepared using albumin binder from Example 9.

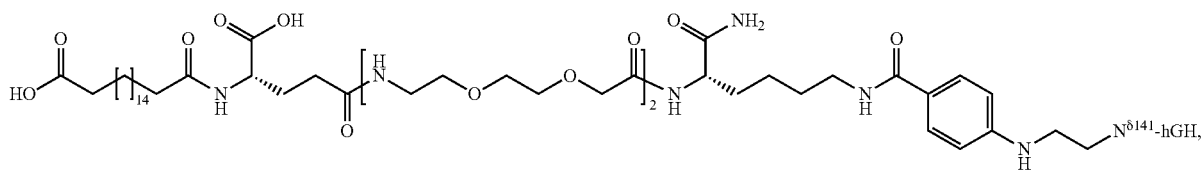

TOF-MS: mass 23.131, 31

Example 34

In a similar way as described in Example 26 above the following compound was prepared using albumin binder from Example 10.

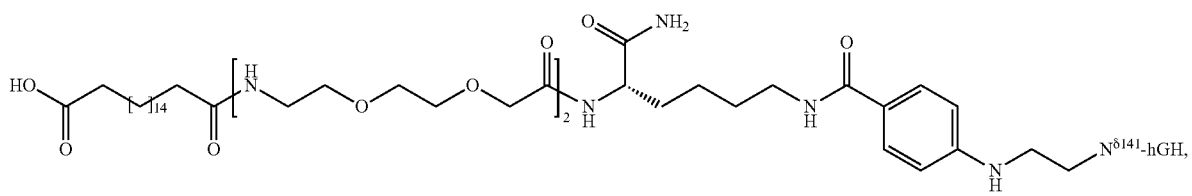

TOF-MS: mass 23.002

Example 35

In a similar way as described in Example 26 above the following compound was prepared using albumin binder from Example 11.

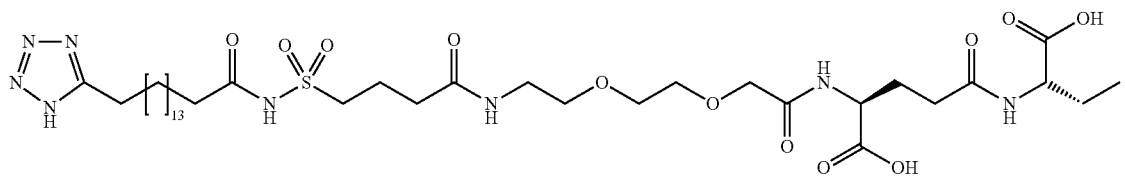

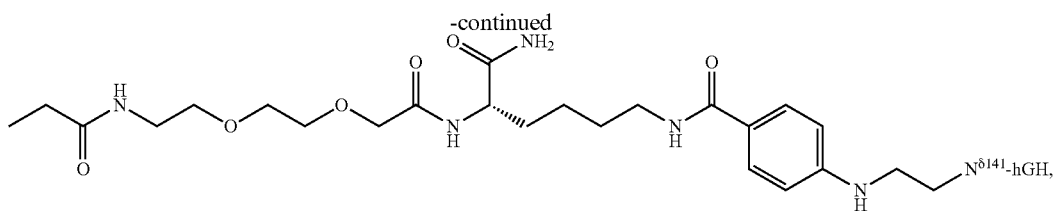

TOF-MS: mass 23.419, 59

Example 36

In a similar way as described in Example 26 above the following compound was prepared using albumin binder from Example 12.

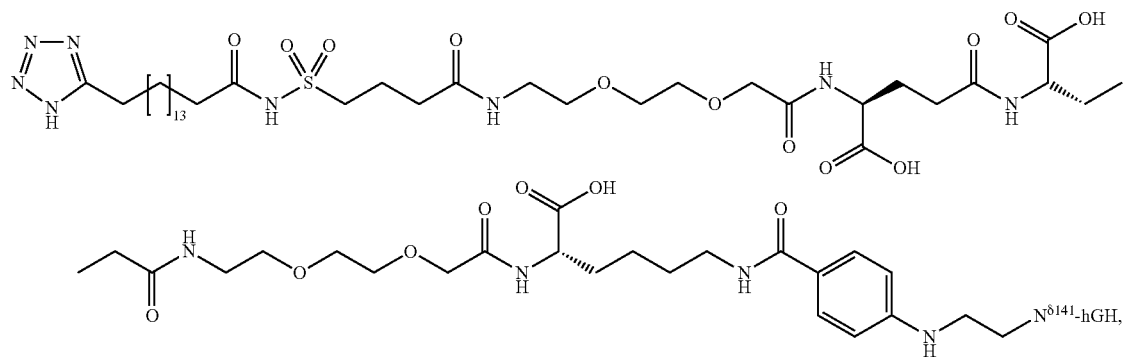

TOF-MS: mass 23.420, 58

Example 37

In a similar way as described in Example 26 above the following compound was prepared using albumin binder from Example 13.

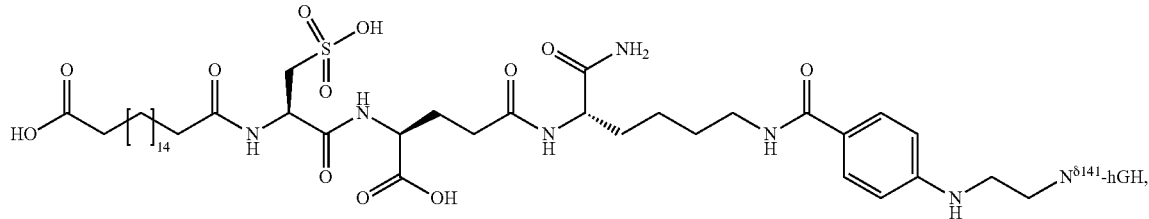

TOF-MS: mass 22.992, 13

Example 38

In a similar way as described in Example 26 above the following compound was prepared using albumin binder from Example 14.

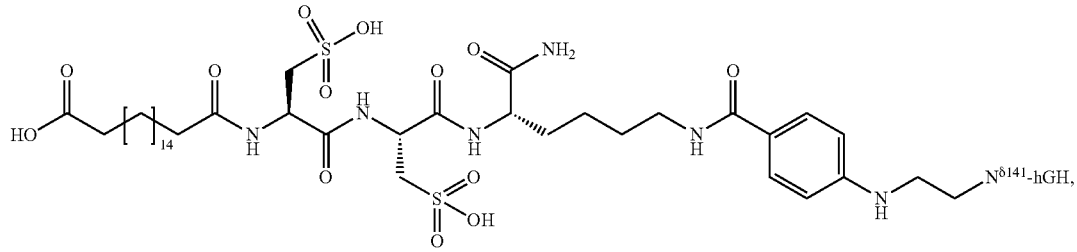

TOF-MS: mass 23.015, 15

Example 39

In a similar way as described in Example 26 above the following compound was prepared using albumin binder from Example 15.

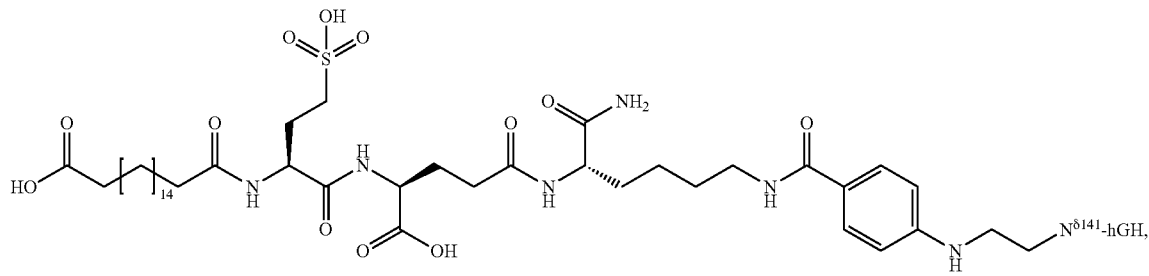

TOF-MS: mass 23.006, 15

Example 40

In a similar way as described in Example 26 above the following compound was prepared using albumin binder from Example 16.

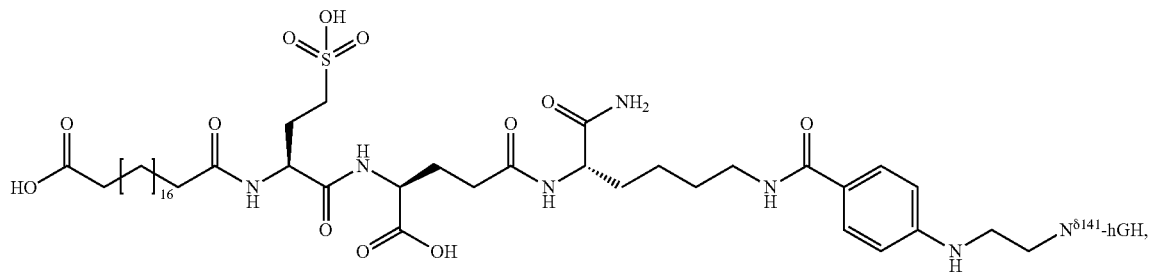

TOF-MS: mass 23.034, 18

Example 41

In a similar way as described in Example 26 above the following compound was prepared using albumin binder from Example 17.

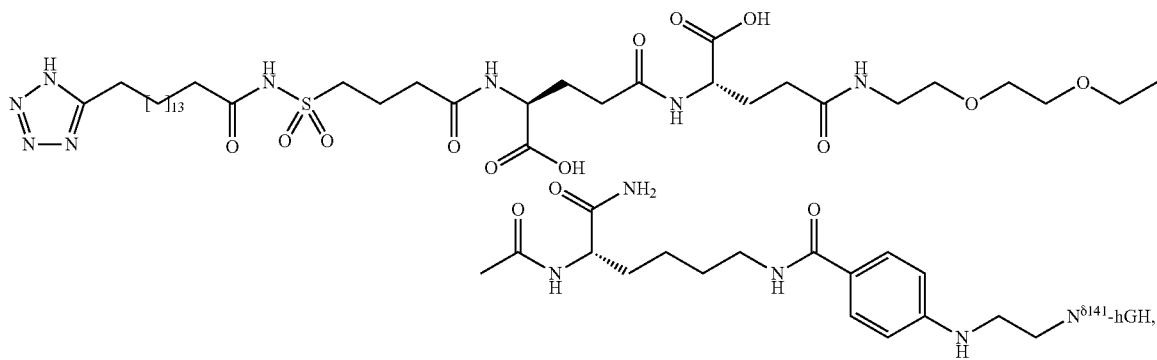

TOF-MS: mass 23.273, 97

Example 42

In a similar way as described in Example 26 above the following compound was prepared using albumin binder from Example 18.

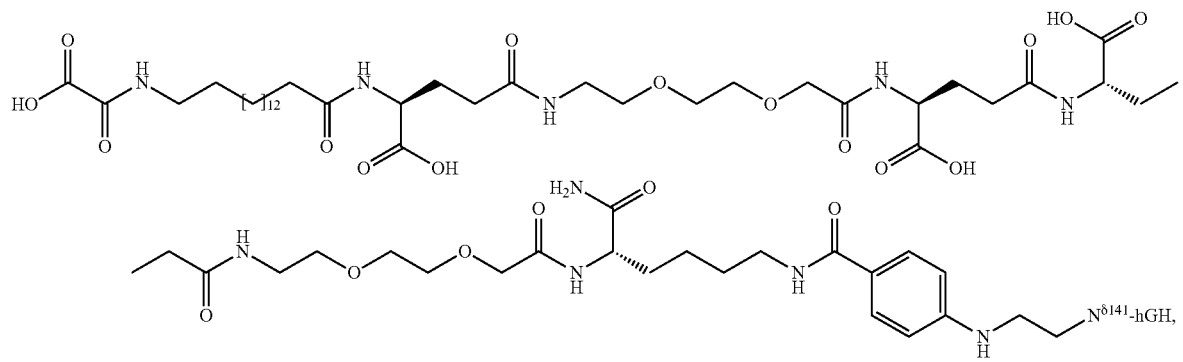

TOF-MS: mass 23.333

Example 43

In a similar way as described in Example 26 above the following compound was prepared using albumin binder from Example 19.

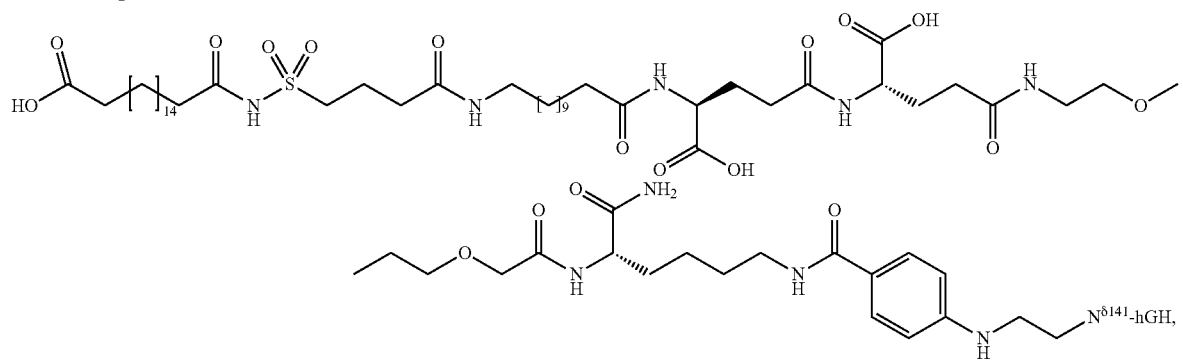

TOF-MS: mass 23.461, 75

Example 44

In a similar way as described in Example 26 above the following compound was prepared using albumin binder from Example 20.

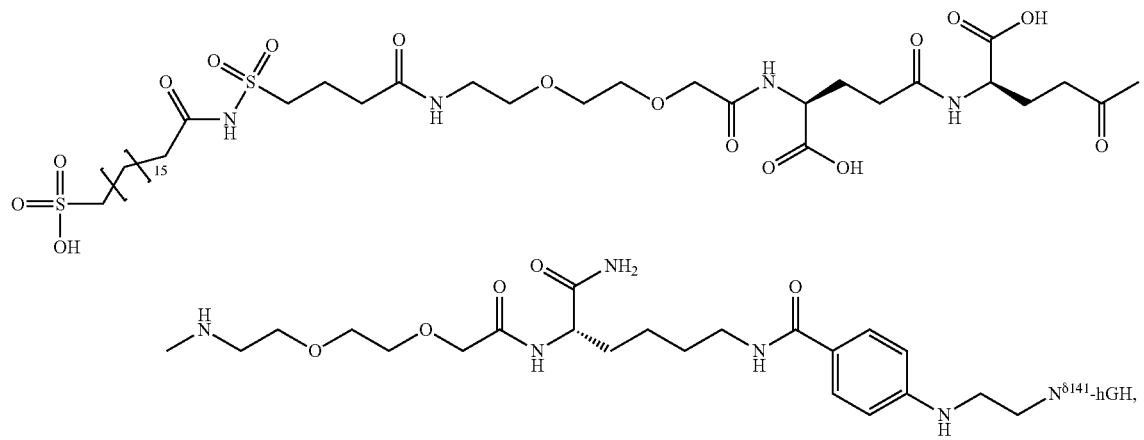

TOF-MS: mass 23.459, 67

Example 45

In a similar way as described in Example 26 above the following compound was prepared using albumin binder from Example 21.

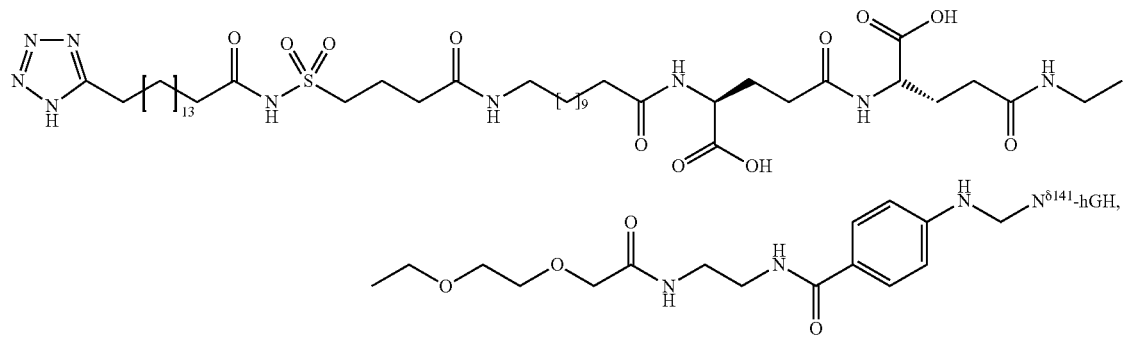

TOF-MS: mass 23.386, 65

Example 46

In a similar way as described in Example 26 above the following compound was prepared using albumin binder from Example 22.

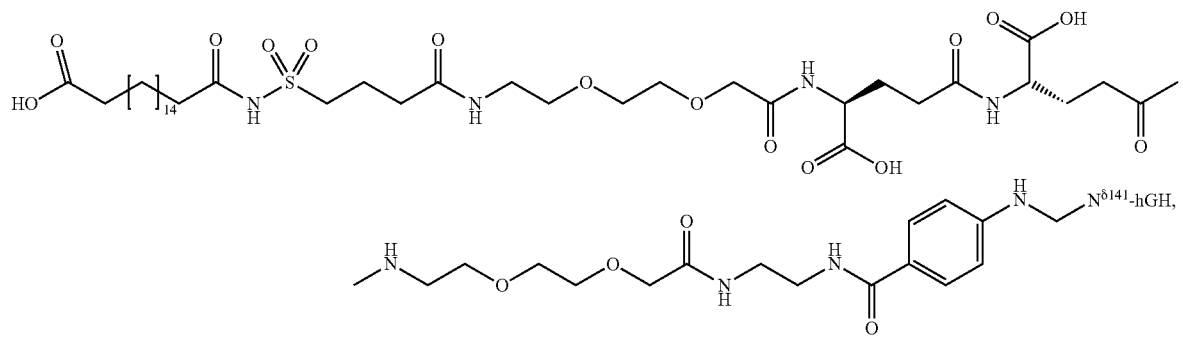

TOF-MS: mass 23.324, 48

Example 47

In a similar way as described in Example 26 above the following compound was prepared using albumin binder from Example 23.

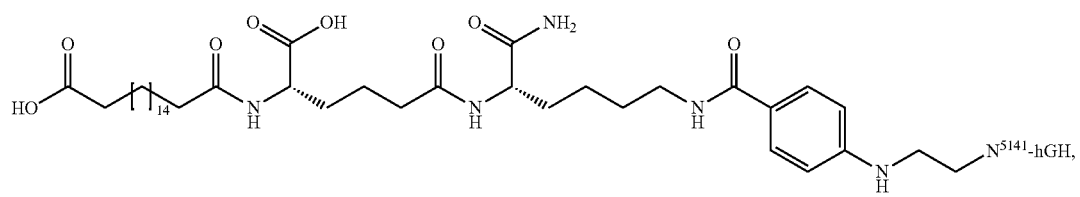

TOF-MS: mass 22.841

Example 48

In a similar way as described in Example 26 above the following compound was prepared using albumin binder from Example 24.

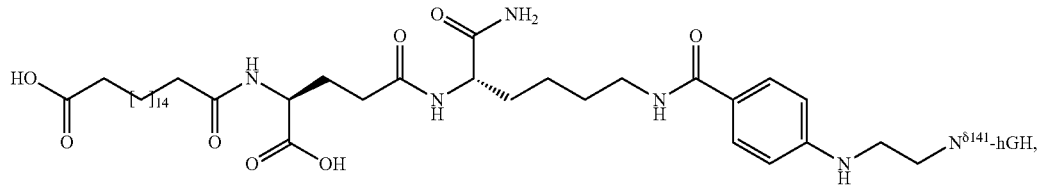

TOF-MS: mass 22.826, 97

Example 49

In a similar way as described in Example 26 above the following compound was prepared using albumin binder from Example 25.

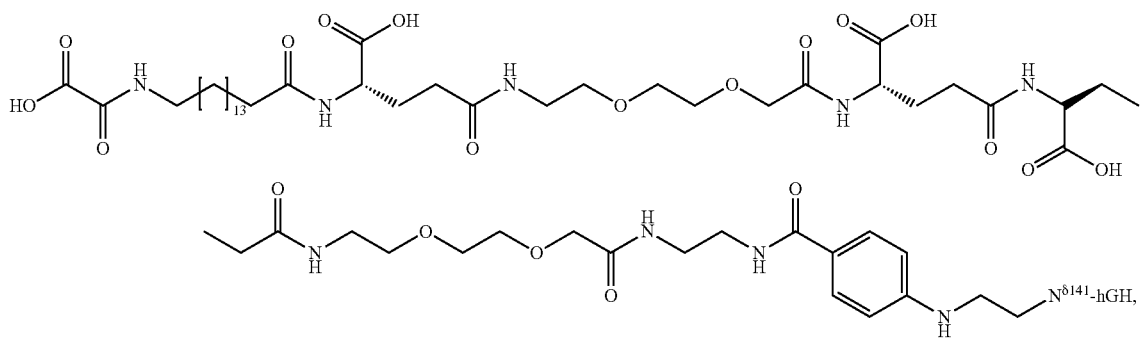

TOF-MS: Rt=4.7 min, mass 1268.7051

Example 50

1. Coupling of Transaminated and Oxidised GH Compound (I) with an Albumine Binder (II)

The following solution was prepared:
Buffer A: Triethanolamine (119 mg, 0.8 mmol) was dissolved in water (40 mL) and pH adjusted to 8.5.

(A) Transamination of hGH (III) with 1,3-diamino-2-propanol

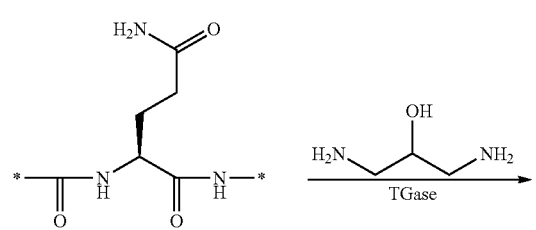

Gln$^{40}$
III

-continued

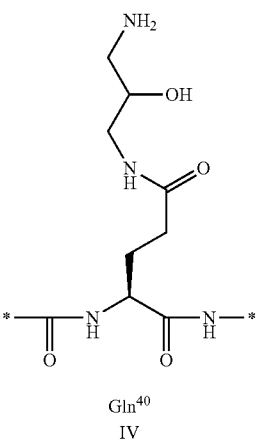

Gln$^{40}$
IV

Transaminated hGH Gln$^{40}$ (IV) was obtained from Example 26 as a biproduct from the CIE chromatography purification.

(B) Oxidation and Reductive Amination of Transaminated hGH Gln⁴⁰ (IV) was Performed as Described in Example 26:

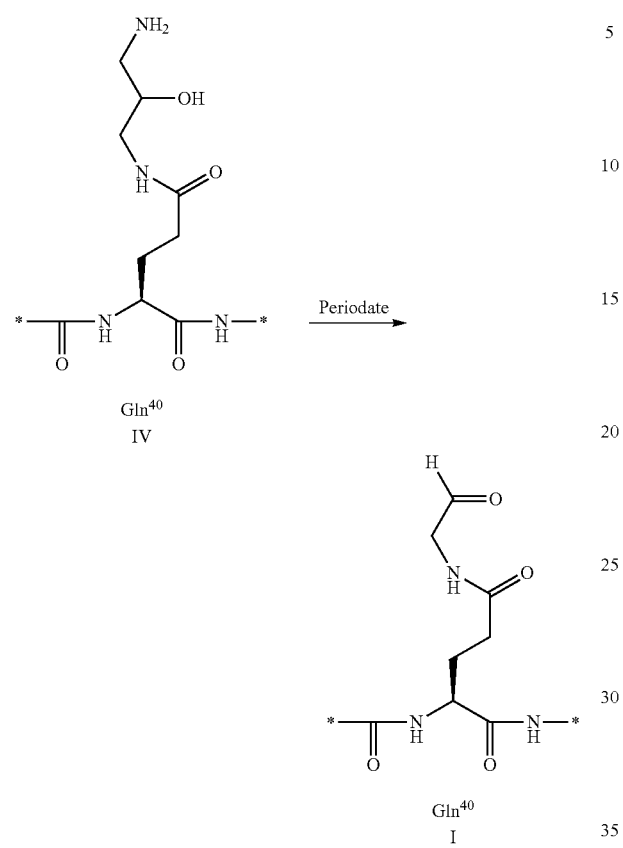

Example 51

1. Coupling of a GH Compound (I) N-Terminaly with an Albumine Binder (II)

(A) Reductive Alkylation of (I) with an Albumin Binder Aldehyde (II)

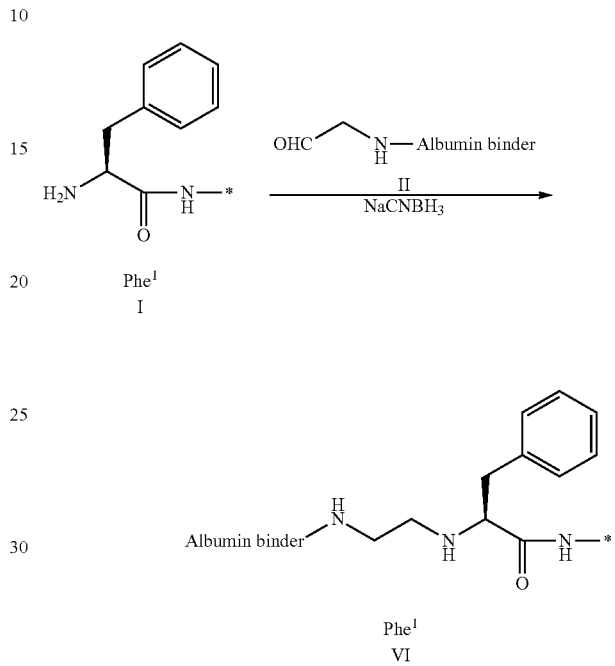

The following solutions were prepared:

In a similar way as described in Example 50 above the following compound was prepared using albumin binder from Example 6.

Albumin binder (II) was obtained as described in Example 3.

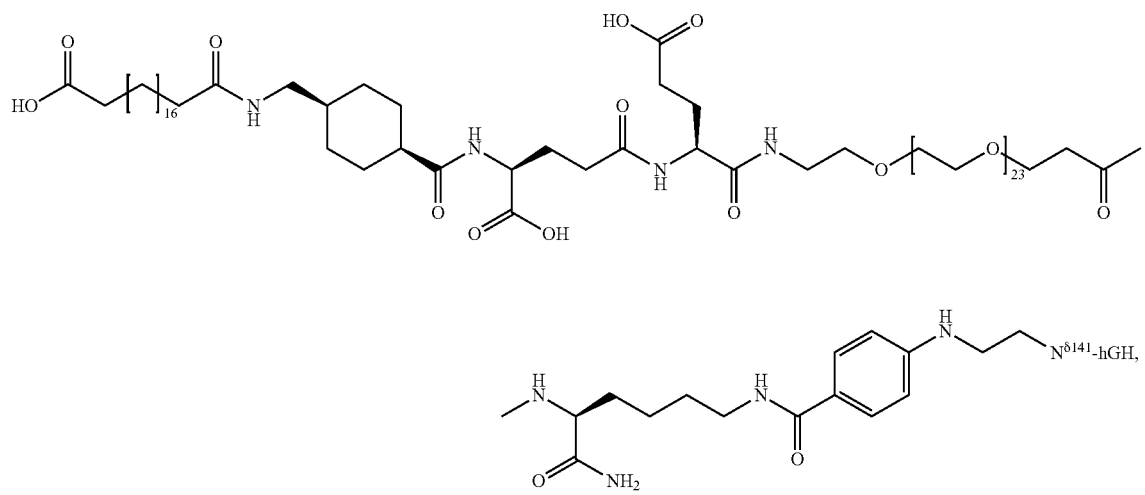

TOF-MS: Rt=4.7 min, mass 23.473, 81

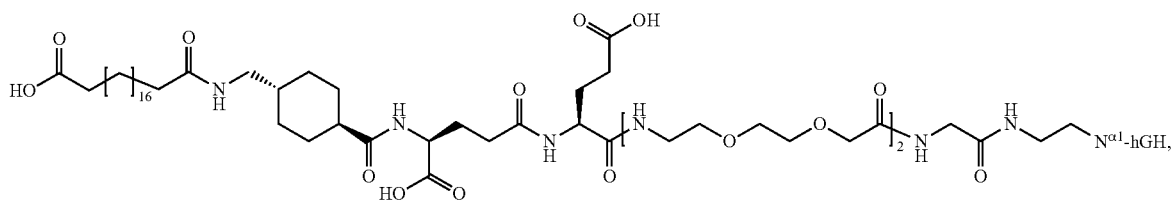

2-($C_{20}$diacid-Trx-γGlu-Glu-OEG-OEG-Gly-Glycin amid)-ethyl-$N^{\alpha 1}$-hGH hGH (23 mg) was dissolved in Hepes buffer (2.3 mL 0.25 mM pH 7.0). $C_{20}$diacid-Trx-γGlu-Glu-OEG-OEG-Gly-Gly-dimethylacetal (2 mg, see example 3 above) was treated with TFA (50 μL) for 6 min. and evaporated to dryness in vacuum. The residue was stripped with EtOH (200 μL) and evaporated to dryness in vacuum. The residue was dissolved in DMF (100 μL) and added to the hGH solution. A precipitate was formed and redissolved by addition of DMF (1 mL). After 1 hr a solution of $NaCNBH_3$ (20 mg, in 0.5 mL MeCN (230 μL)) was added portionwise and left for 20 hrs. The reaction was quenched by addition of AcOH (2 mL) and diluted with water to a total volume of 20 ml and purified on prep. HPLC on a C18 column with a gradient of MeCN/0.1% TFA from 40-80% against 0.1% TFA in water. The latest eluting peak was collected, diluted from 70% MeCN to 10% with water and lyophilized affording 4.51 mg of the title compound.

TOF-MS: mass 23.237, 6

Pharmacological Methods

Assay (I) BAF-3 GHR Assay to Determine Growth Hormone Activity

The BAF-3 cells (a murine pro-B lymphoid cell line derived from the bone marrow) was originally IL-3 dependent for growth and survival. Il-3 activates JAK-2 and STAT which are the same mediators GH is activating upon stimulation. After transfection of the human growth hormone receptor the cell line was turn into a growth hormone-dependent cell line. This clone can be used to evaluate the effect of different growth hormone samples on the survival of the BAF-3 GHR.

The BAF-3 GHR cells are grown in starvation medium (culture medium without growth hormone) for 24 hours at 37° C., 5% $CO_2$.

The cells are washed and re-suspended in starvation medium and seeded in plates. 10 μl of growth hormone compound or human growth hormone in different concentrations or control is added to the cells, and the plates are incubated for 68 hours at 37° C., 5% $CO_2$.

AlamarBlue® is added to each well and the cells are then incubated for another 4 hours. The AlamarBlue® is a redox indicator, and is reduced by reactions innate to cellular metabolism and, therefore, provides an indirect measure of viable cell number.

Finally, the metabolic activity of the cells is measure in a fluorescence plate reader. The absorbance in the samples is expressed in % of cells not stimulated with growth hormone compound or control and from the concentration-response curves the activity (amount of a compound that stimulates the cells with 50%) can be calculated.

LIST OF EMBODIMENTS

Embodiment 1

A process for preparing a conjugated protein or glycoprotein which comprises the steps of reacting a protein or glycoprotein with a water insoluble albumin binder in the presence of an optionally substituted cyclodextrin molecule.

Embodiment 2

A process as defined in Embodiment 1, wherein the cyclodextrin molecule comprises optionally substituted β-cyclodextrin.

Embodiment 3

A process as defined in Embodiment 1 or Embodiment 2, wherein the optionally substituted cyclodextrin comprises cyclodextrin optionally substituted by one or more $C_{1-6}$ alkyl (e.g. methyl, ethyl or propyl) each of which may be optionally substituted by one or more hydroxyl groups (e.g. hydroxyethyl-cyclodextrin or hydroxypropyl-cyclodextrin).

Embodiment 4

A process as defined in Embodiment 3, wherein the optionally substituted cyclodextrin comprises 2-hydroxyethyl-β-cyclodextrin.

Embodiment 5

A process as defined in any preceding Embodiments, wherein the optionally substituted cyclodextrin molecule is added at a concentration of between 1% and 10% (e.g. 5%).

Embodiment 6

A process as defined in any preceding Embodiments, which comprises reaction in an aqueous buffered solution, such as a Hepes buffer (e.g. 50 mM Hepes, 100 mM NaCl and 10 mM $CaCl_2$).

Embodiment 7

A process as defined in any preceding Embodiments, which comprises reaction at a constant pH (e.g. pH 7.0) and a constant temperature (e.g. 25° C.).

Embodiment 8

A process as defined in any preceding Embodiments, wherein said protein conjugate is a protein conjugate of the formula (I):

$$(A\text{-}W\text{—}B)_y\text{—}P \quad (I)$$

wherein
P represents a protein or glycoprotein;
B represents a hydrophilic spacer;
W is a chemical group linking A and B;
A represents an albumin binding residue; and
y represents an integer selected from 1, 2, 3, 4, 5, 6, 7, 8, 9 or 10;

or a pharmaceutically acceptable salt, solvate or prodrug thereof, such that said A-W—B— moiety comprises a water insoluble moiety.

Embodiment 9

A process as defined in Embodiment 8, wherein said protein has a molecular mass above 20,000 Da.

Embodiment 10

A process as defined in Embodiment 8 or Embodiment 9, wherein said protein represents a blood coagulation factor, such as FVII, FX, FII, FV, protein C, protein S, tPA, PAI-1, tissue factor, FXI, FXII, and FXIII, as well as sequence FVIII, FIX variants thereof.

Embodiment 11

A process as defined in Embodiment 10, wherein the blood coagulation factor is FVII, such as FVIIa.

Embodiment 12

A process as defined in Embodiment 8 or Embodiment 9 wherein said protein represents a growth hormone (GH).

Embodiment 13

A process as defined in any of Embodiments 8 to 12, wherein y represents an integer selected from 1, 2 or 3.

Embodiment 14

A process as defined in any of Embodiments 8 to 13, wherein y represents an integer selected from 2, 3, 4, 5 or 6.

Embodiment 15

A process as defined in Embodiment 14 wherein y represents 2.

Embodiment 16

A process as defined in any of Embodiments 8 to 12 wherein y represents 1.

Embodiment 17

A process as defined in any of Embodiments 8 to 16, wherein the hydrophilic spacer has a cLogP<0.

Embodiment 18

A process as defined in any of Embodiments 8 to 17, wherein the hydrophilic spacer has the formula $-X_1-X_2-X_3-X_4-$ wherein
$X_1$ is $-W_1-[(CHR^1)_{I1}-W_2]_{m1}-\{[(CH_2)_{n1}E1]_{m2}-[(CHR^2)_{I2}-W_3]_{m3}\}_{n2}-$,
$X_2$ is $-[(CHR^3)_{I3}-W_4]_{m4}-\{[(CH_2)_{n3}E2]_{m5}-[(CHR^4)_{I4}-W_5]_{m5}\}_{n4}-$,
$X_3$ is $-[(CHR^5)_{I5}-W_6]_{m7}-$,
$X_4$ is $F-D1-(CH_2)_{I6}-D2-$,
I1, I2, I3, I4, I5 and I6 independently are selected from 0-16, m1, m3, m4, m6 and m7 independently are selected from 0-10,
m2 and m5 independently are selected from 0-25,
n1, n2, n3 and n4 independently are selected from 0-16,
F is aryl, heteroaryl, pyrrolidine-2,5-dione c, wherein the aryl and heteroaryl groups are optionally substituted with halogen, —CN, —OH, —C(O)OH, —C(O)NH$_2$, —S(O)$_2$OH or C$_{1-6}$-alkyl,
$R^1$, $R^2$, $R^3$, $R^4$ and $R^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or heteroaryl; wherein the alkyl, aryl and heteroaryl groups optionally are substituted with halogen, —C(O)OH, —C(O)NH$_2$, —S(O)OH, —S(O)$_2$OH, —CN or —OH,
D1, D2, E1 and E2 independently are selected from —O—, —NR$^6$—, —N(COR$^7$)— or a valence bond; wherein R$^6$ and R$^7$ independently represent hydrogen or C$_{1-6}$-alkyl,
$W_1$ to $W_6$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1.

Embodiment 19

A process as defined in any of Embodiments 8 to 18, wherein W has the formula $-W_7-Y-$, wherein
Y is —(CH$_2$)$_{I7}$—C$_{3-10}$-Cycloalkyl-W$_8$— or a valence bond,
I7 is 0-6,
$W_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1,
$W_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

Embodiment 20

A process as defined in Embodiment 18 or Embodiment 19, wherein I1, I2, I3, I4, I5 and I6 independently represent 0-6.

Embodiment 21

A process as defined in any of Embodiments 18 to 20, wherein m1, m3, m4, m6 and m7 independently represent 0-6.

Embodiment 22

A process as defined in any of Embodiments 18 to 21, wherein m2 and m5 independently represent 0-10.

Embodiment 23

A process as defined in any of Embodiments 18 to 22, wherein n1, n2, n3 and n4 independently represent 0-10, such as 0-6.

Embodiment 24

A process as defined in any of Embodiments 18 to 23, wherein D1 and D2 are independently selected from —O— or —NR$^6$— or a valence bond.

Embodiment 25

A process as defined in any of Embodiments 18 to 24, wherein D1 and D2 are both —O—.

Embodiment 26

A process as defined in any of Embodiments 18 to 25, wherein D1 and D2 are both —NR$^6$—.

Embodiment 27

A process as defined in any of Embodiments 18 to 26, wherein E1 and E2 are independently selected from —O— or —NR$^6$— or a valence bond.

Embodiment 28

A process as defined in any of Embodiments 18 to 27, wherein E1 and E2 are both —O—.

Embodiment 29

A process as defined in any of Embodiments 18 to 27, wherein E1 and E2 are both —NR$^6$—.

Embodiment 30

A process as defined in any of Embodiments 18 to 29, wherein $W_1$ through $W_8$ independently are selected from the group consisting of —C(O)NH—, —NHC(O)—, —C(O)NHCH$_2$—, —CH$_2$NHC(O)—, —C(O)NHS(O)$_2$—, —S(O)$_2$NHC(O)— or a valence bond.

Embodiment 31

A process as defined in any of Embodiments 18 to 30, wherein $R^1$, $R^2$, $R^3$, $R^4$ and $R^5$ independently are selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH.

Embodiment 32

A process as defined in any of Embodiments 18 to 31, wherein $X_1$ is —W$_1$—[(CHR$^1$)$_{r1}$—W$_2$]$_{m1}$—{[(CH$_2$)$_{n1}$O]$_{m2}$—[(CHR$^2$)$_{r2}$—W$_3$]$_{m3}$}$_{n2}$— and $X_2$ is —[(CHR$^3$)$_{r3}$—W$_4$]$_{m4}$—{[(CH$_2$)$_{n3}$O]$_{m5}$—[(CHR$^4$)$_{r4}$—W$_5$]$_{m6}$}$_{n4}$—, wherein —{[(CH$_2$)$_{n1}$O]$_{m2}$—[(CHR$^2$)$_{r2}$—W$_3$]$_{m3}$}$_{n2}$— and —{[(CH$_2$)$_{n3}$O]$_{m5}$—[(CHR$^4$)$_{r4}$—W$_5$]$_{m6}$}$_{n4}$— are selected from,

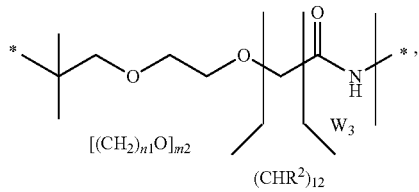 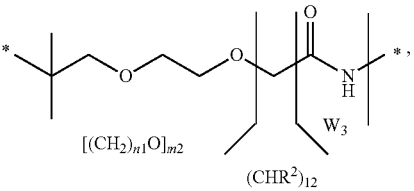

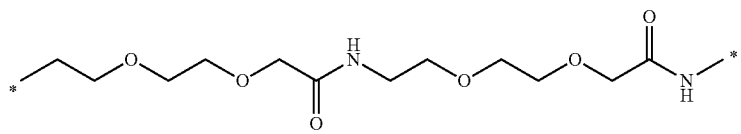

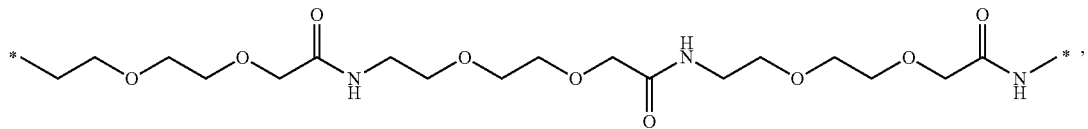

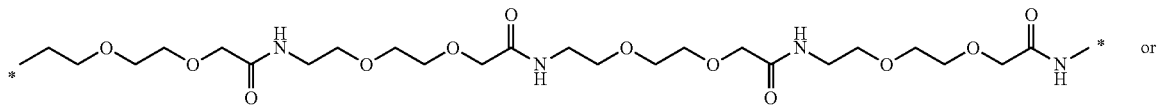

or

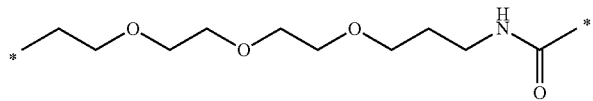

111
Embodiment 33
A process as defined in any of Embodiments 8 to 32 wherein the hydrophilic spacer is selected from:
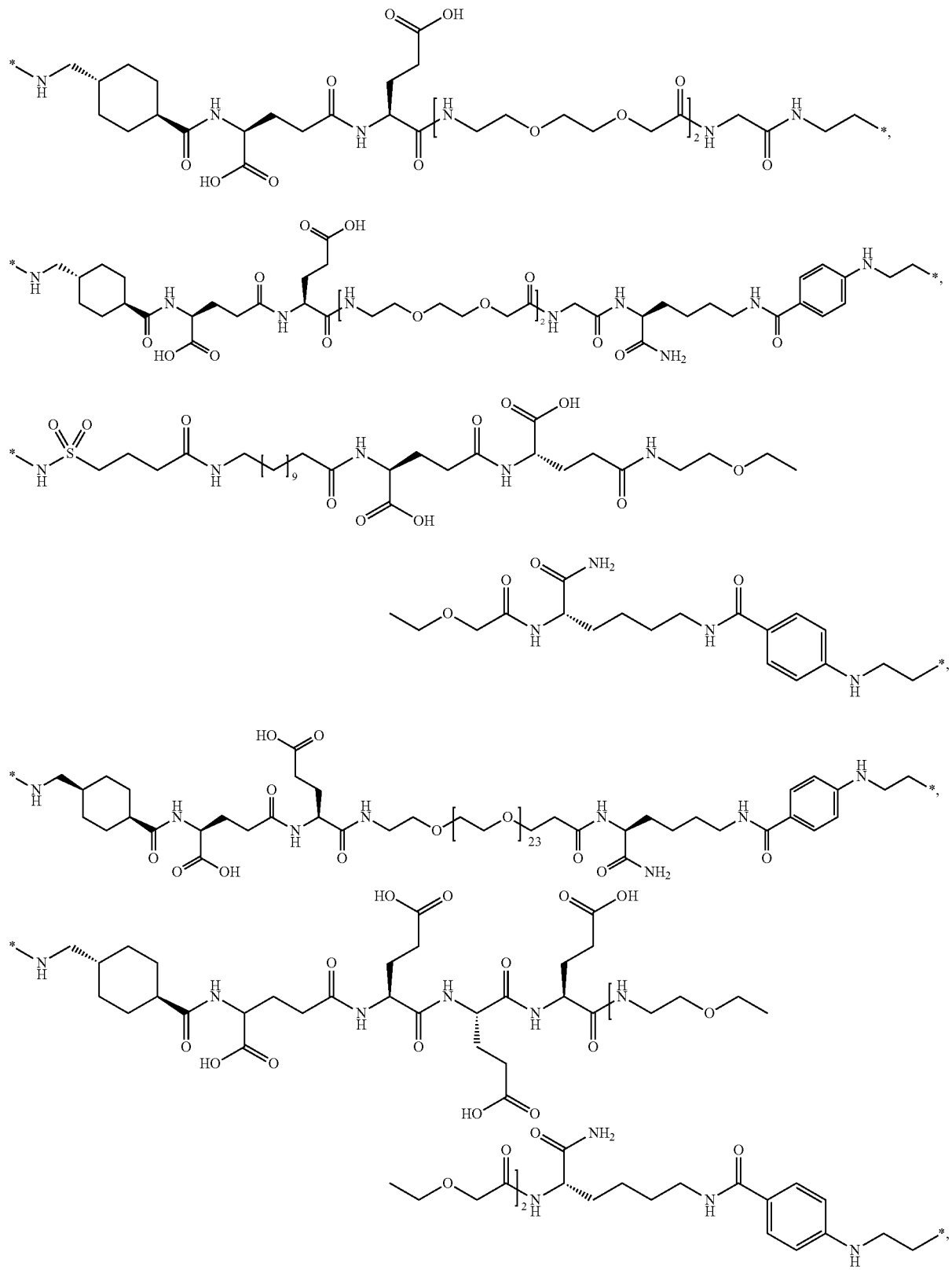

-continued
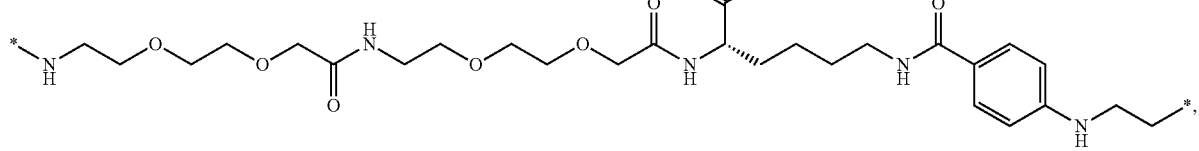
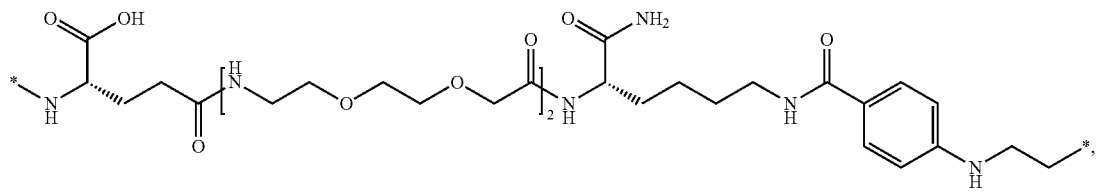
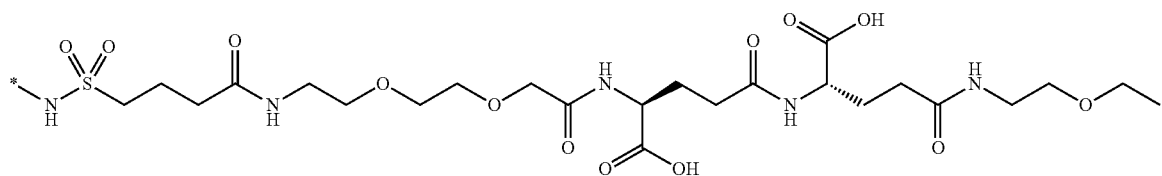
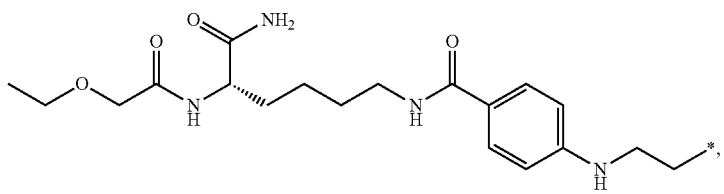
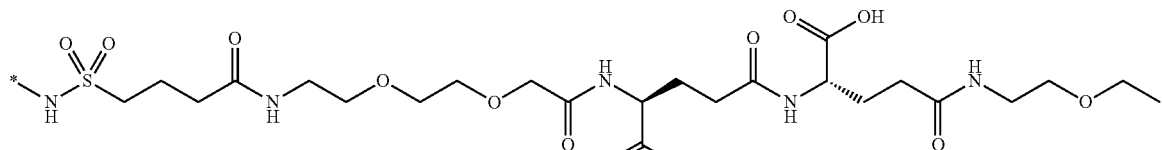
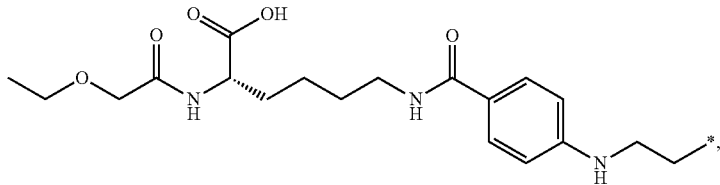
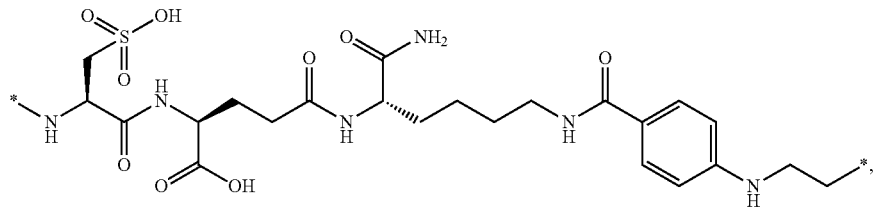
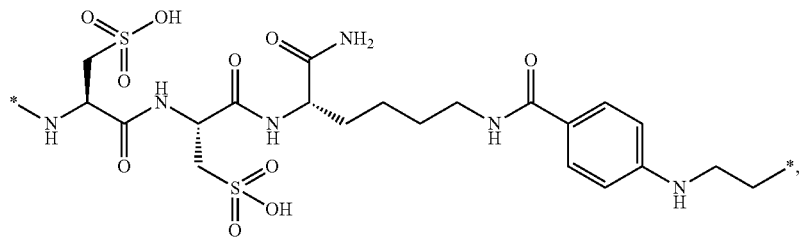

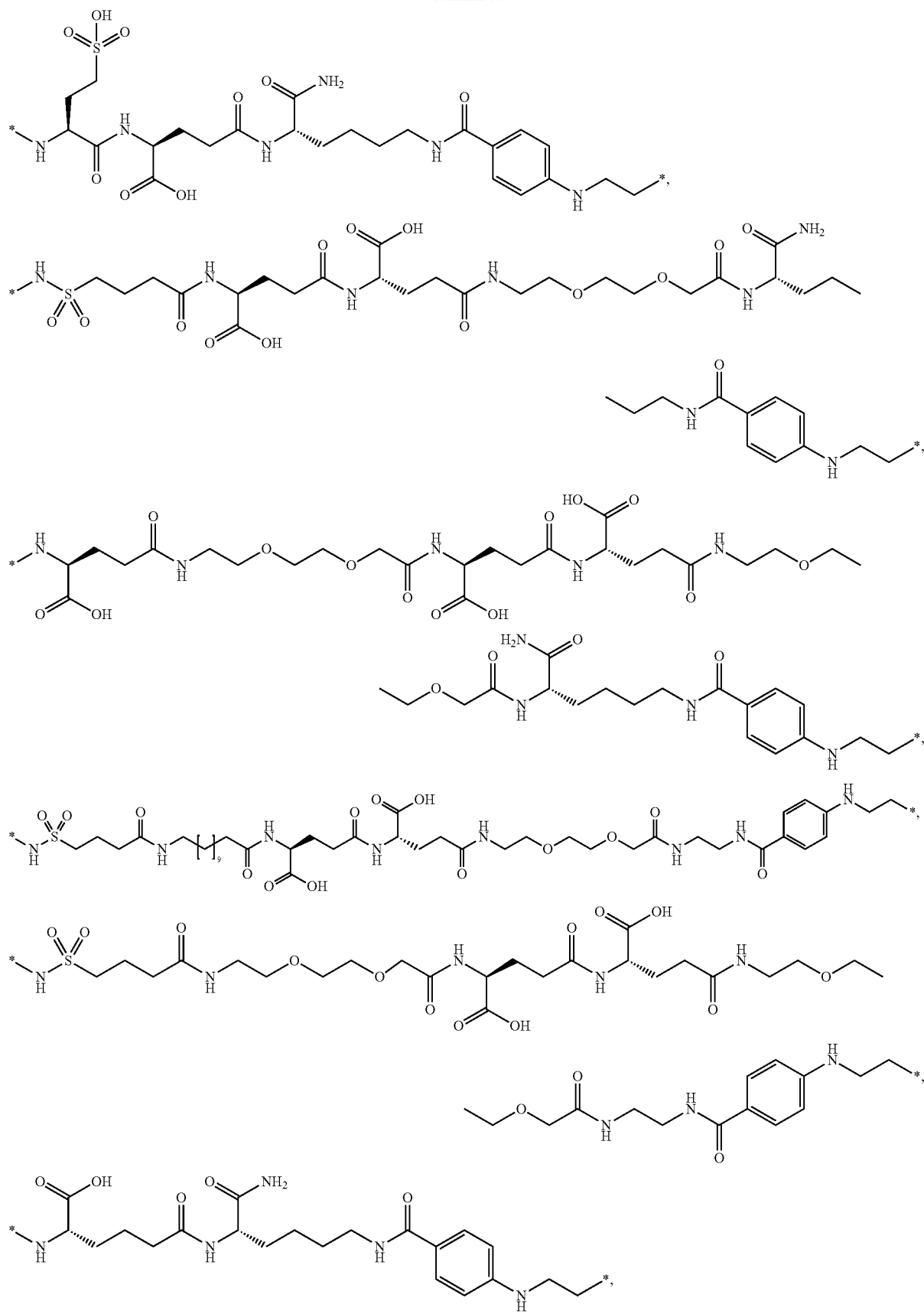

-continued

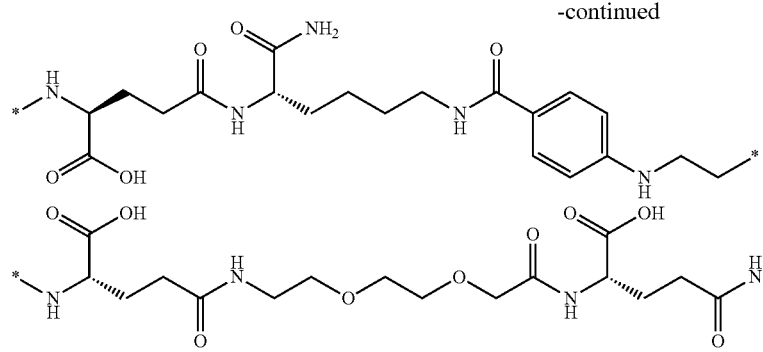

or

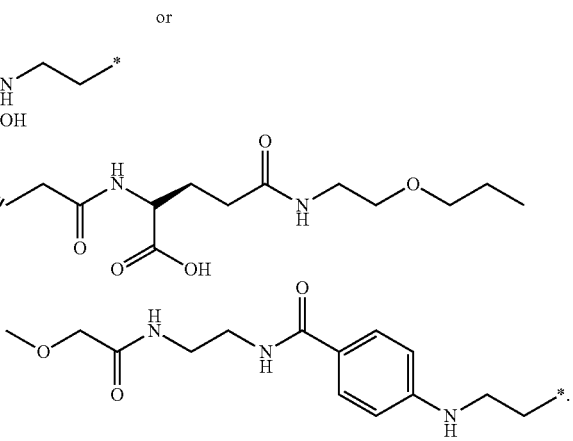

Embodiment 34

A process as defined in any of Embodiments 8 to 33 wherein the molar weight of said hydrophilic spacer is in the range from 80 D to 1500 D or in the range from 500 D to 1100 D.

Embodiment 35

A process as defined in any preceding Embodiments wherein said albumin binding residue is a lipophilic residue.

Embodiment 36

A process as defined in any preceding Embodiments wherein said albumin binding residue binds non-covalently to albumin.

Embodiment 37

A process as defined in any preceding Embodiments wherein said albumin binding residue is negatively charged at physiological pH.

Embodiment 38

A process as defined in any preceding Embodiments wherein said albumin binding residue has a binding affinity towards human serum albumin that is below about 10 μM or below about 1 μM.

Embodiment 39

A process as defined in any preceding Embodiments wherein said albumin binding residue is selected from a straight chain alkyl group, a branched alkyl group, a group which has an ω-carboxylic acid group or an ω-carboxylic acid isoster.

Embodiment 40

A process as defined in any preceding Embodiments wherein said albumin binding residue has from 6 to 40 carbon atoms, from 8 to 26 carbon atoms or from 8 to 20 carbon atoms.

Embodiment 41

A process as defined in any preceding Embodiments wherein said albumin binding residue is a peptide, such as a peptide comprising less than 40 amino acid residues.

Embodiment 42

A process as defined in any preceding Embodiments wherein the albumin hinder is selected from

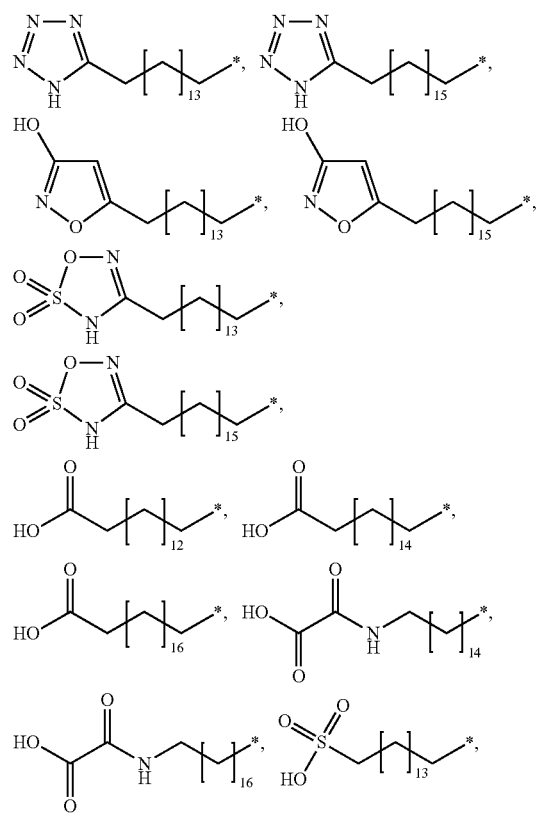

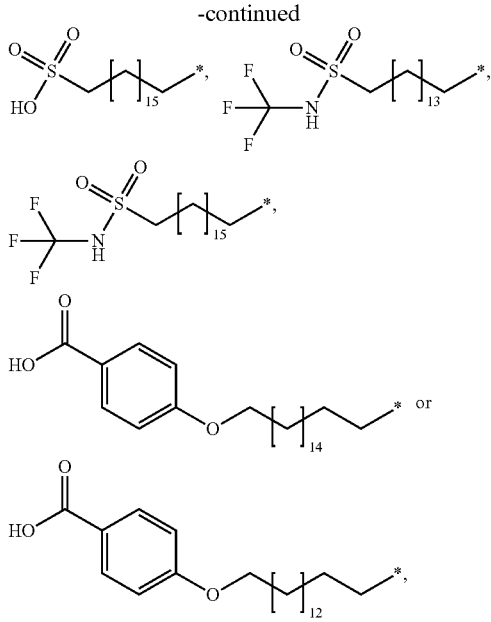

wherein * denotes the attachment to B through W.

Embodiment 43

A process as defined in any of Embodiments 8 to 42, wherein the albumin binding residue A is attached to the glutamine residue of protein P via hydrophilic spacer B.

Embodiment 44

A process as defined in any of Embodiments 8 to 42, wherein the albumin binding residue A is attached to a cystein residue of protein P via hydrophilic spacer B.

Embodiment 45

A process as defined in any of Embodiments 8 to 42, wherein the albumin binding residue A is attached to the N-terminal residue of protein P via hydrophilic spacer B.

Embodiment 46

A process as defined in any of Embodiments 8 to 42, wherein the albumin binding residue A is attached to the C-terminal residue of protein P via hydrophilic spacer B.

Embodiment 47

A process as defined in any of Embodiments 8 to 42, wherein the albumin binding residue A is attached to a lysine residue of protein P via hydrophilic spacer B.

Embodiment 48

A process as defined in any of Embodiments 8 to 42, wherein the albumin binding residue A is attached to an oxidized glycan residue of glycoprotein P via hydrophilic spacer B.

Embodiment 49

A process as defined in any preceding Embodiments wherein said conjugate is selected from

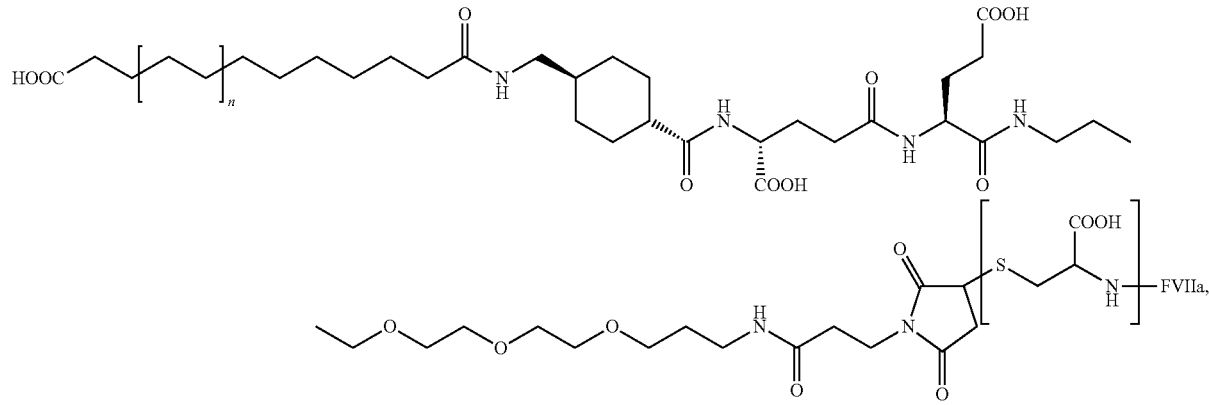

n = 5

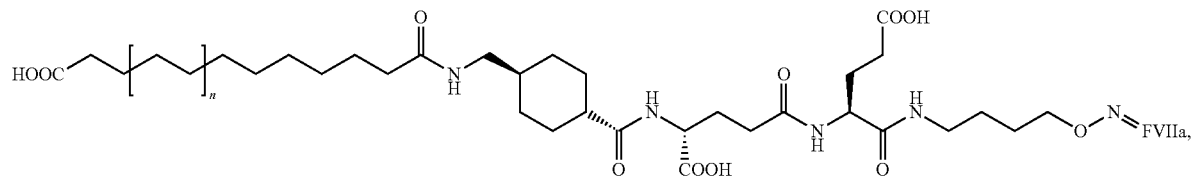

n = 5

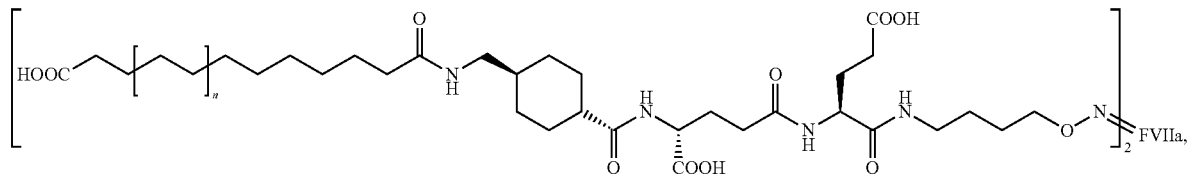

n = 5

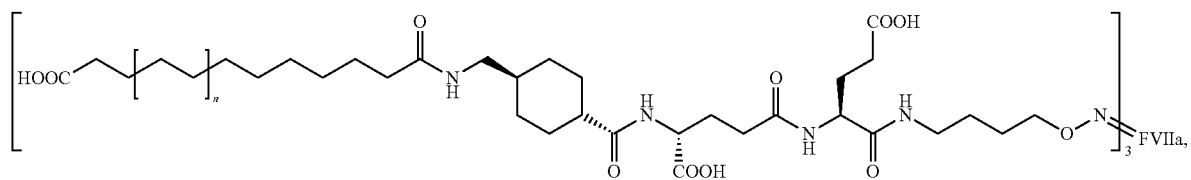
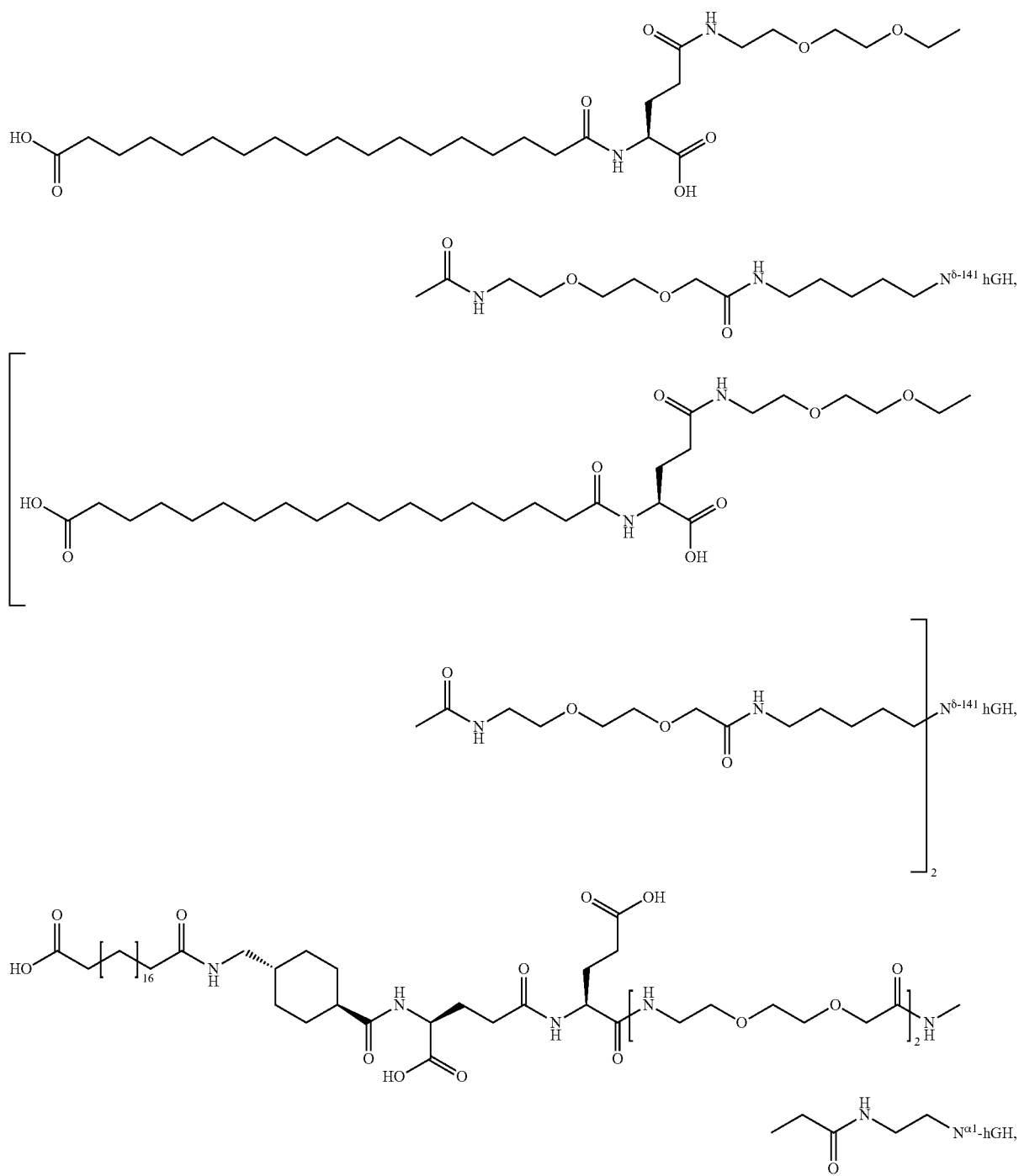

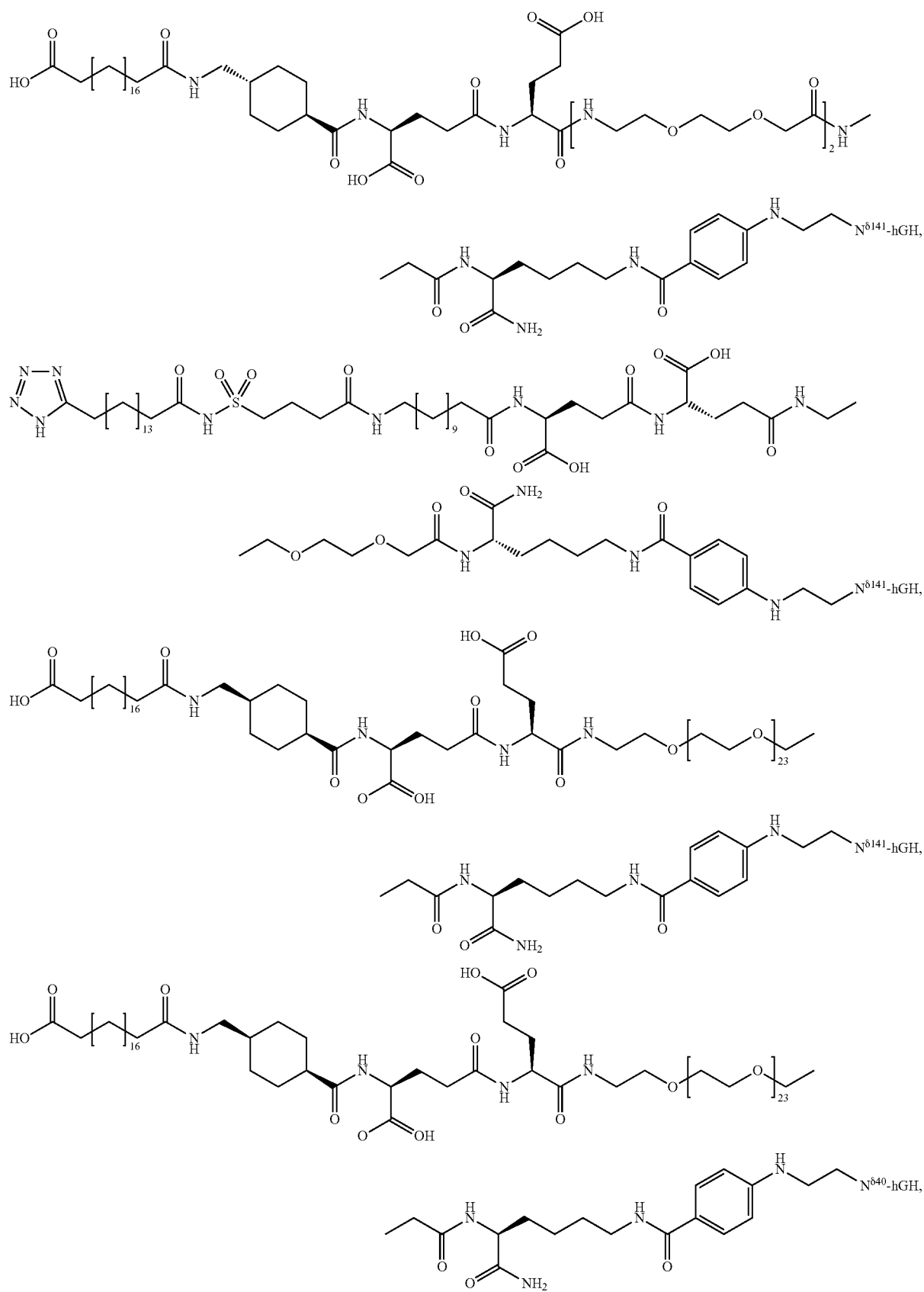

125    126
-continued
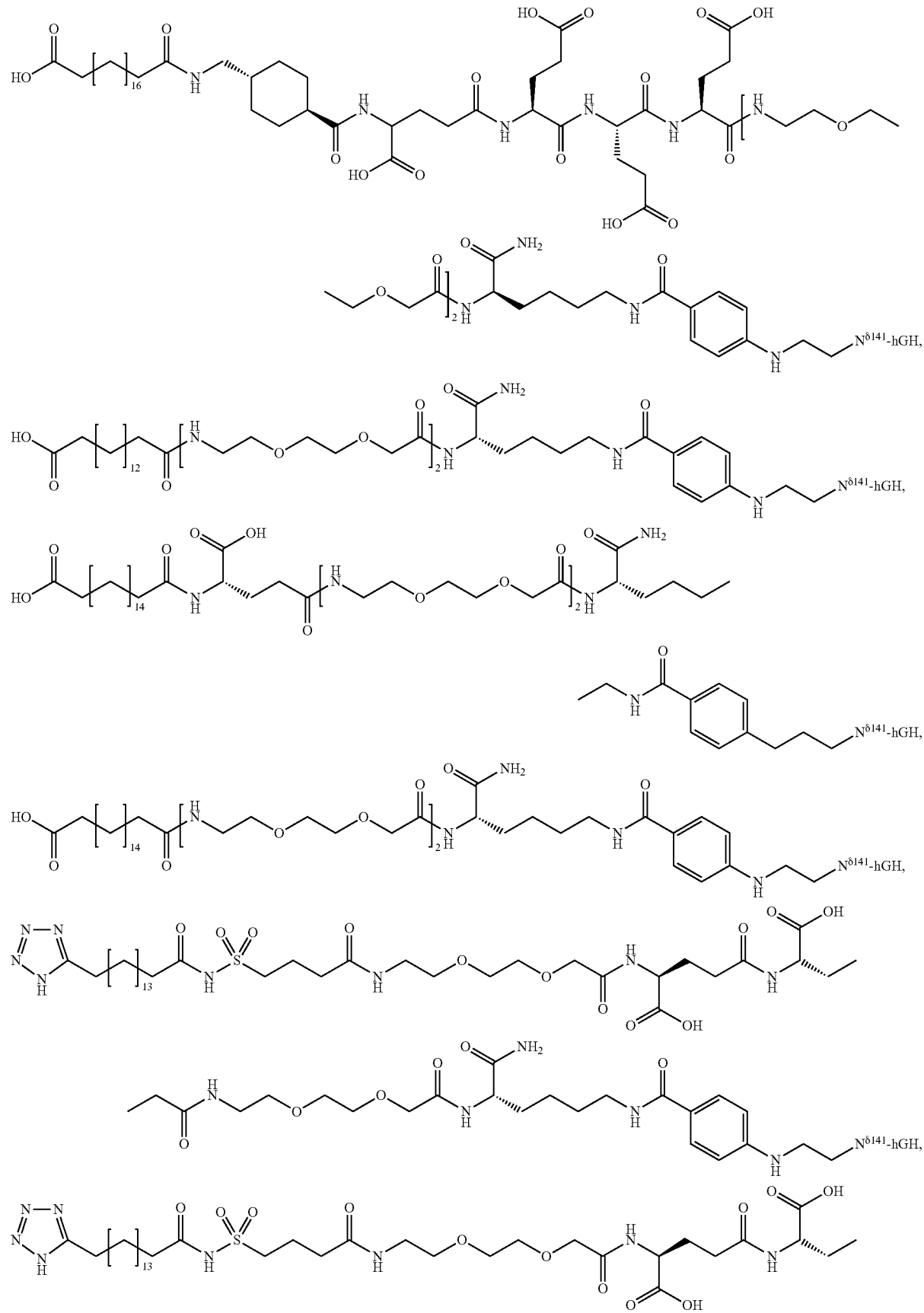

-continued
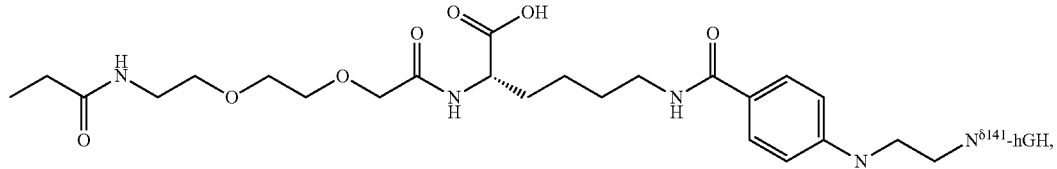
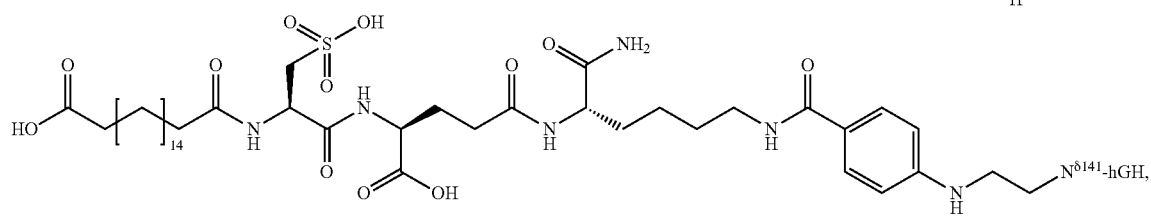
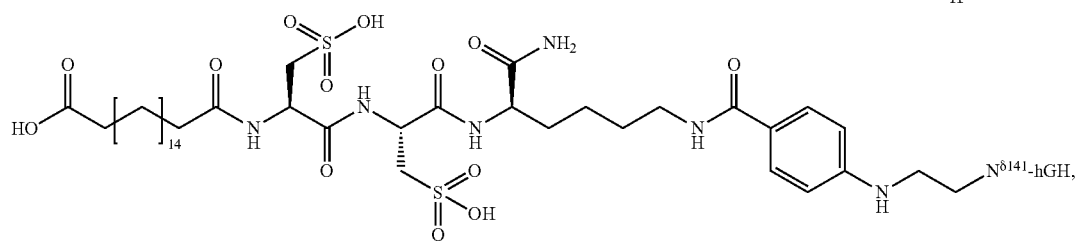
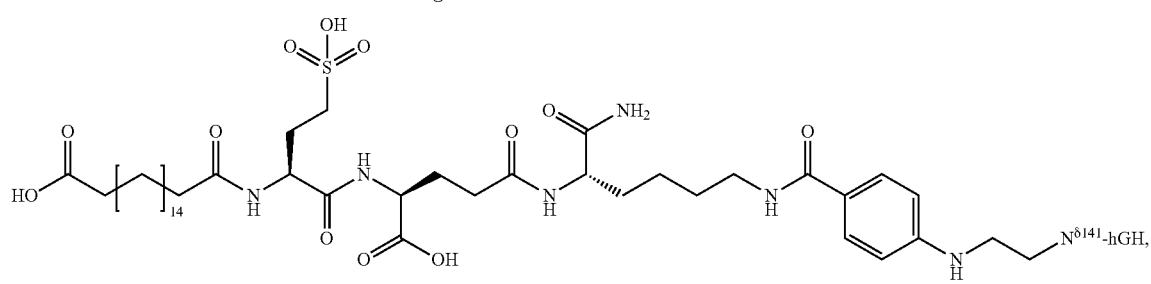
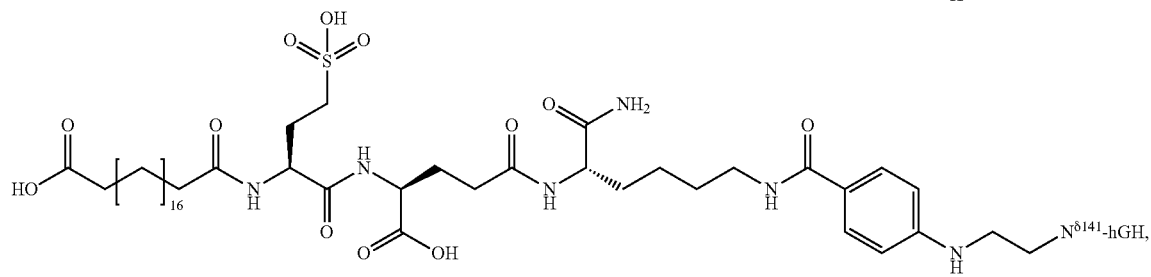
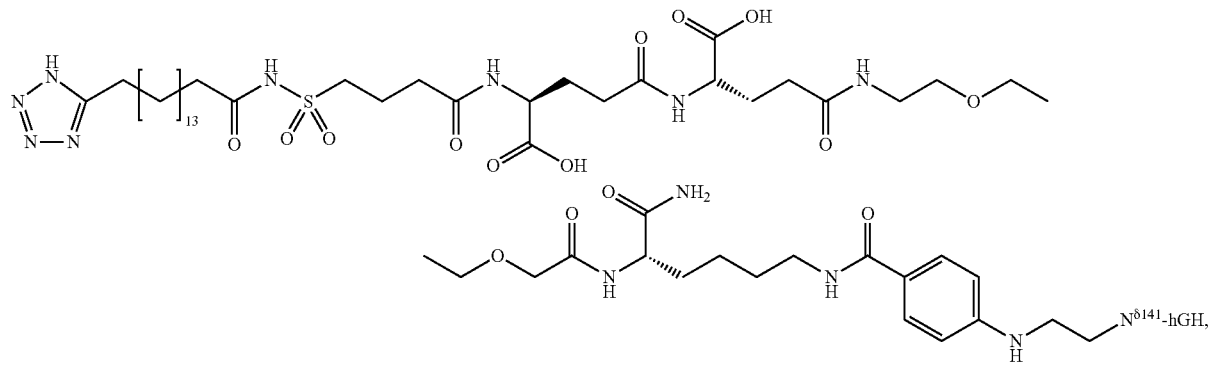
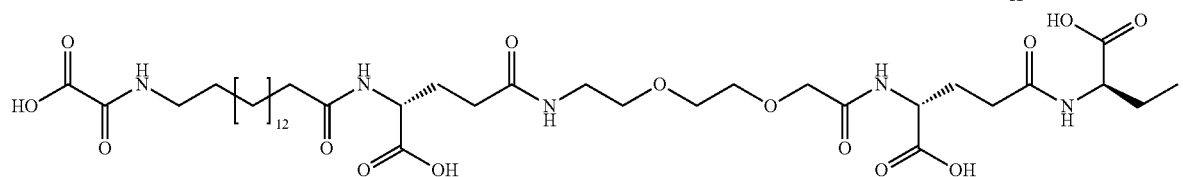

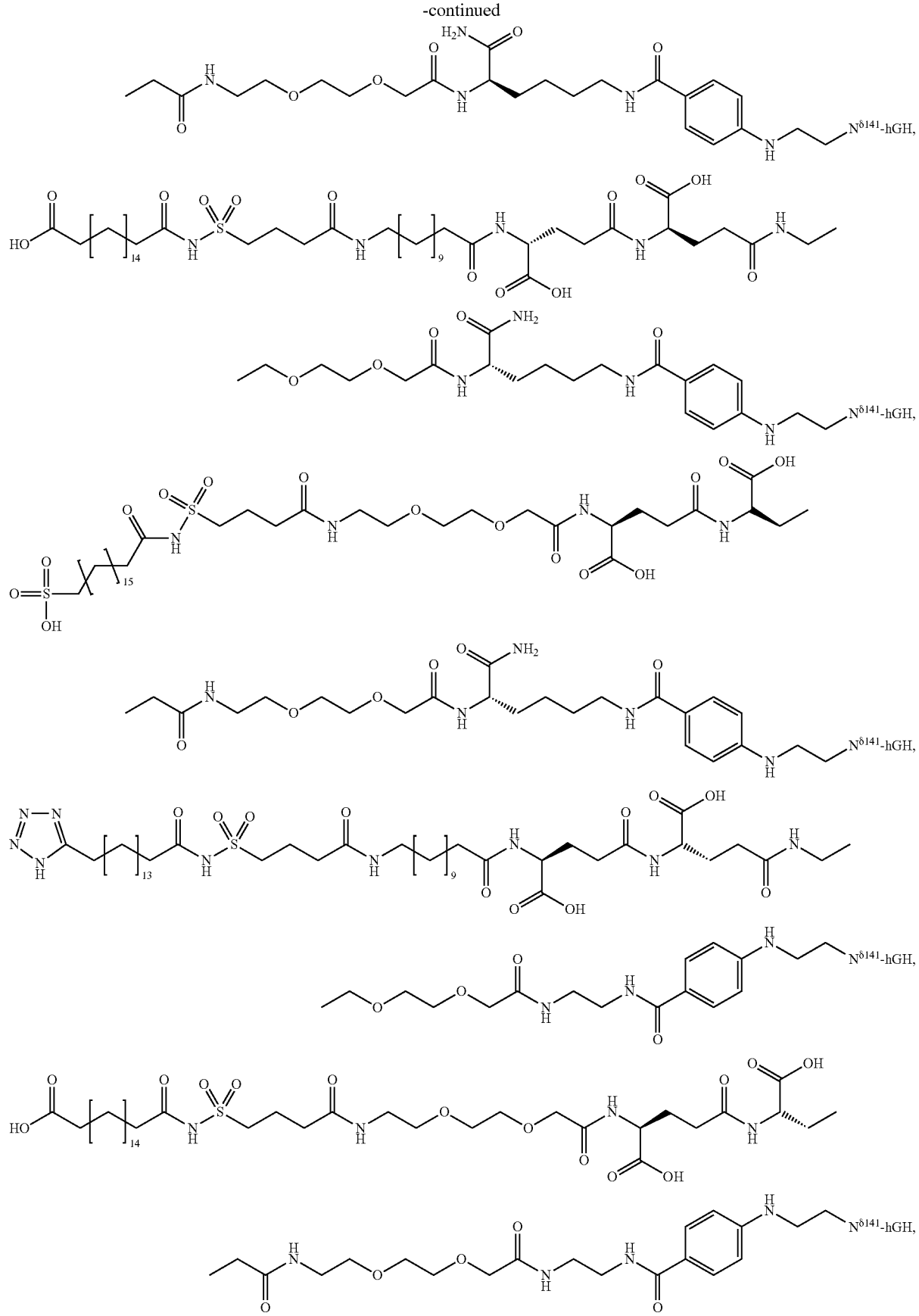
-continued

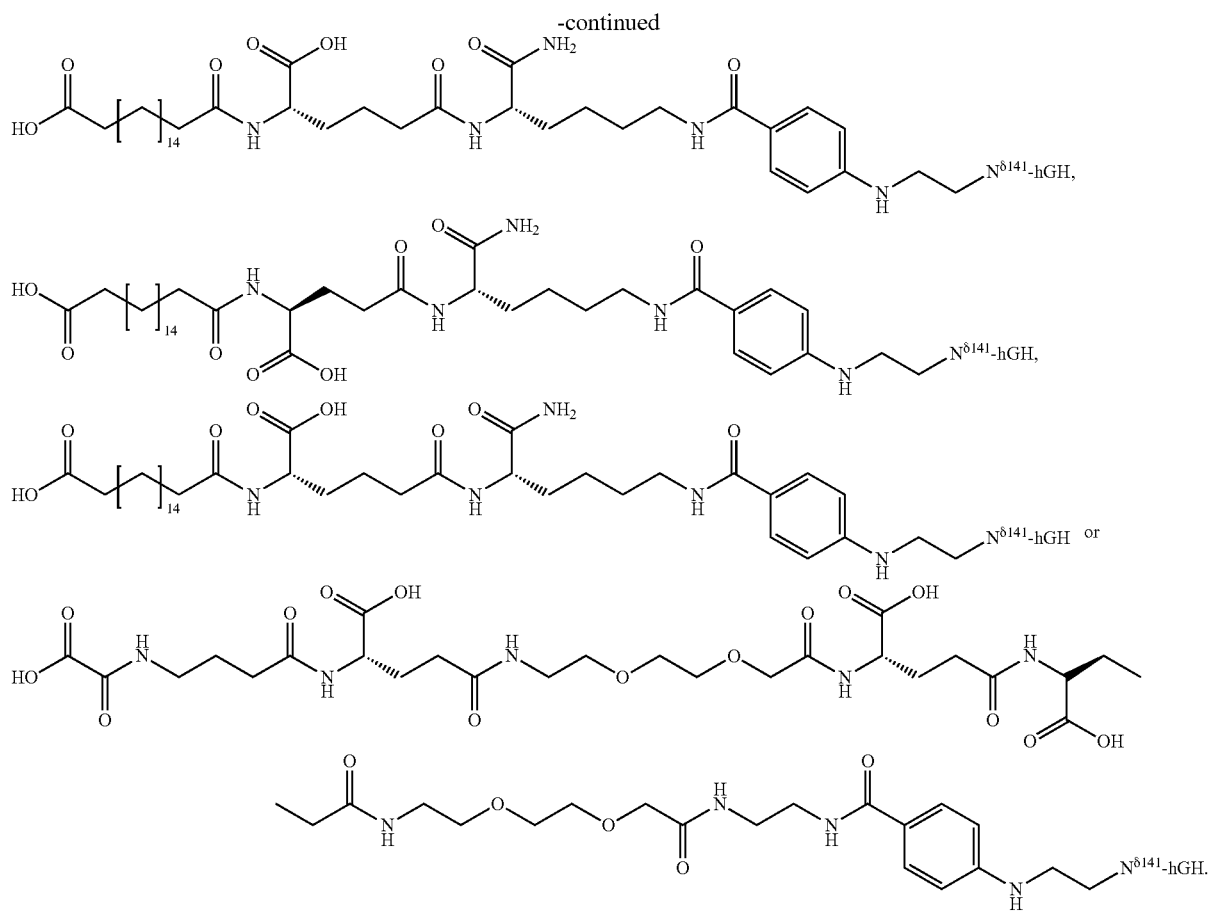

Embodiment 50

A conjugated protein obtainable by a process as defined in any preceding Embodiments.

Embodiment 51

A protein conjugate which comprises a protein or glycoprotein linked to an albumin binding residue via a hydrophilic spacer, or a pharmaceutically acceptable salt, solvate or prodrug thereof.

Embodiment 52

A protein conjugate of the formula (I):

$$(A\text{-}W\text{—}B)_y\text{—}P \qquad (I)$$

wherein
P represents a protein or glycoprotein;
B represents a hydrophilic spacer;
W is a chemical group linking A and B;
A represents an albumin binding residue; and
y represents an integer selected from 1, 2, 3, 4, 5, 6, 7, 8, 9 or 10;
or a pharmaceutically acceptable salt, solvate or prodrug thereof.

Embodiment 53

A protein conjugate as defined in Embodiment 51 or Embodiment 52, wherein said protein has a molecular mass above 20,000 Da.

Embodiment 54

A protein conjugate as defined in Embodiments 51 to 53, wherein said protein represents a blood coagulation factor, such as FVII, FX, FII, FV, protein C, protein S, tPA, PAI-1, tissue factor, FXI, FXII, and FXIII, as well as sequence FVIII, FIX variants thereof.

Embodiment 55

A protein conjugate as defined in Embodiment 54, wherein the blood coagulation factor is FVII, such as FVIIa.

Embodiment 56

A protein conjugate as defined in Embodiment 52 or Embodiment 53 wherein said protein represents a growth hormone (GH).

Embodiment 57

A protein conjugate as defined in any of Embodiments 52 to 56, wherein y represents an integer selected from 1, 2 or 3.

Embodiment 58

A protein conjugate as defined in any of Embodiments 52 to 57, wherein y represents an integer selected from 2, 3, 4, 5 or 6.

Embodiment 59

A protein conjugate as defined in Embodiment 58 wherein y represents 2.

Embodiment 60

A protein conjugate as defined in any of Embodiments 52 to 57 wherein y represents 1.

Embodiment 61

A protein conjugate as defined in any of Embodiments 52 to 60, wherein the hydrophilic spacer has a cLogP<0.

Embodiment 62

A protein conjugate as defined in any of Embodiments 52 to 61, wherein the hydrophilic spacer has the formula $$-X_1-X_2-X_3-X_4-$$

wherein
$X_1$ is $-W_1-[(CHR^1)_{I1}-W_2]_{m1}-\{[(CH_2)_{n1}E1]_{m2}-[(CHR^2)_{I2}-W_3]_{m3}\}_{n2}-$,
$X_2$ is $-[(CHR^3)_{I3}-W_4]_{m4}-\{[(CH_2)_{n3}E2]_{m5}-[(CHR^4)_{I4}-W_5]_{m5}\}_{n4}-$,
$X_3$ is $-[(CHR^5)_{I5}-W_6]_{m7}-$,
$X_4$ is F-D1-$(CH_2)_{I6}$-D2-,
I1, I2, I3, I4, I5 and I6 independently are selected from 0-16,
m1, m3, m4, m6 and m7 independently are selected from 0-10,
m2 and m5 independently are selected from 0-25,
n1, n2, n3 and n4 independently are selected from 0-16,
F is aryl, heteroaryl, pyrrolidine-2,5-dione c, wherein the aryl and heteroaryl groups are optionally substituted with halogen, —CN, —OH, —C(O)OH, —C(O)NH$_2$, —S(O)$_2$OH or C$_{1-6}$-alkyl,
$R^1$, $R^2$, $R^3$, $R^4$ and $R^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or heteroaryl; wherein the alkyl, aryl and heteroaryl groups optionally are substituted with halogen, —C(O)OH, —C(O)NH$_2$, —S(O)OH, —S(O)$_2$OH, —CN or —OH,
D1, D2, E1 and E2 independently are selected from —O—, —NR$^6$—, —N(COR$^7$)— or a valence bond; wherein R$^6$ and R$^7$ independently represent hydrogen or C$_{1-6}$-alkyl,
$W_1$ to $W_6$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1.

Embodiment 63

A protein conjugate as defined in any of Embodiments 52 to 62, wherein W has the formula $$-W_7-Y-,$$

wherein
Y is —(CH$_2$)$_{I7}$—C$_{3-10}$-Cycloalkyl-W$_8$— or a valence bond,
I7 is 0-6,
$W_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —C(O)—, —C(O)O—, —OC(O)—, or a valence bond; wherein s3 is 0 or 1,
$W_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —C(O)CH=CH—, —CH=CHC(O)—, —(CH$_2$)$_{s4}$—, —C(O)—, —C(O)O—, —OC(O)—, or a valence bond; wherein s4 is 0 or 1.

Embodiment 64

A protein conjugate as defined in Embodiment 62 or Embodiment 63, wherein I1, I2, I3, I4, I5 and I6 independently represent 0-6.

Embodiment 65

A protein conjugate as defined in any of Embodiments 62 to 64, wherein m1, m3, m4, m6 and m7 independently represent 0-6.

Embodiment 66

A protein conjugate as defined in any of Embodiments 62 to 65, wherein m2 and m5 independently represent 0-10.

Embodiment 67

A protein conjugate as defined in any of Embodiments 62 to 66, wherein n1, n2, n3 and n4 independently represent 0-10, such as 0-6.

Embodiment 68

A protein conjugate as defined in any of Embodiments 62 to 67, wherein D1 and D2 are independently selected from —O— or —NR$^6$— or a valence bond.

Embodiment 69

A protein conjugate as defined in any of Embodiments 62 to 68, wherein D1 and D2 are both —O—.

Embodiment 70

A protein conjugate as defined in any of Embodiments 62 to 68, wherein D1 and D2 are both —NR$^6$—.

Embodiment 71

A protein conjugate as defined in any of Embodiments 62 to 70, wherein E1 and E2 are independently selected from —O— or —NR$^6$— or a valence bond.

Embodiment 72

A protein conjugate as defined in any of Embodiments 62 to 71, wherein E1 and E2 are both —O—.

Embodiment 73

A protein conjugate as defined in any of Embodiments 62 to 71, wherein E1 and E2 are both —NR$^6$—.

Embodiment 74

A protein conjugate as defined in any of Embodiments 62 to 73, wherein $W_1$ through $W_8$ independently are selected from the group consisting of —C(O)NH—, —NHC(O)—, —C(O)NHCH$_2$—, —CH$_2$NHC(O)—, —C(O)NHS(O)$_2$—, —S(O)$_2$NHC(O)— or a valence bond.

Embodiment 75

A protein conjugate as defined in any of Embodiments 62 to 74, wherein R$^1$, R$^2$, R$^3$, R$^4$ and R$^5$ independently are selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH.

Embodiment 76

A protein conjugate as defined in any of Embodiments 62 to 75, wherein X$_1$ is —W$_1$—[(CHR$^1$)$_{l1}$—W$_2$]$_{m1}$—{[(CH$_2$)$_{n1}$O]$_{m2}$—[(CHR$^2$)$_{l2}$—W$_3$]$_{m3}$}$_{n2}$— and X$_2$ is —[(CHR$^3$)$_{l3}$—W$_4$]$_{m4}$—{[(CH$_2$)$_{n3}$O]$_{m5}$—[(CHR$^4$)$_{l4}$—W$_5$]$_{m6}$}$_{n4}$—, wherein —{[(CH$_2$)$_{n1}$O]$_{m2}$—[(CHR$^2$)$_{l2}$—W$_3$]$_{m3}$}$_{n2}$— and —{[(CH$_2$)$_{n3}$O]$_{m5}$—[(CHR$^4$)$_{l4}$—W$_5$]$_{m6}$}$_{n4}$— are selected from,

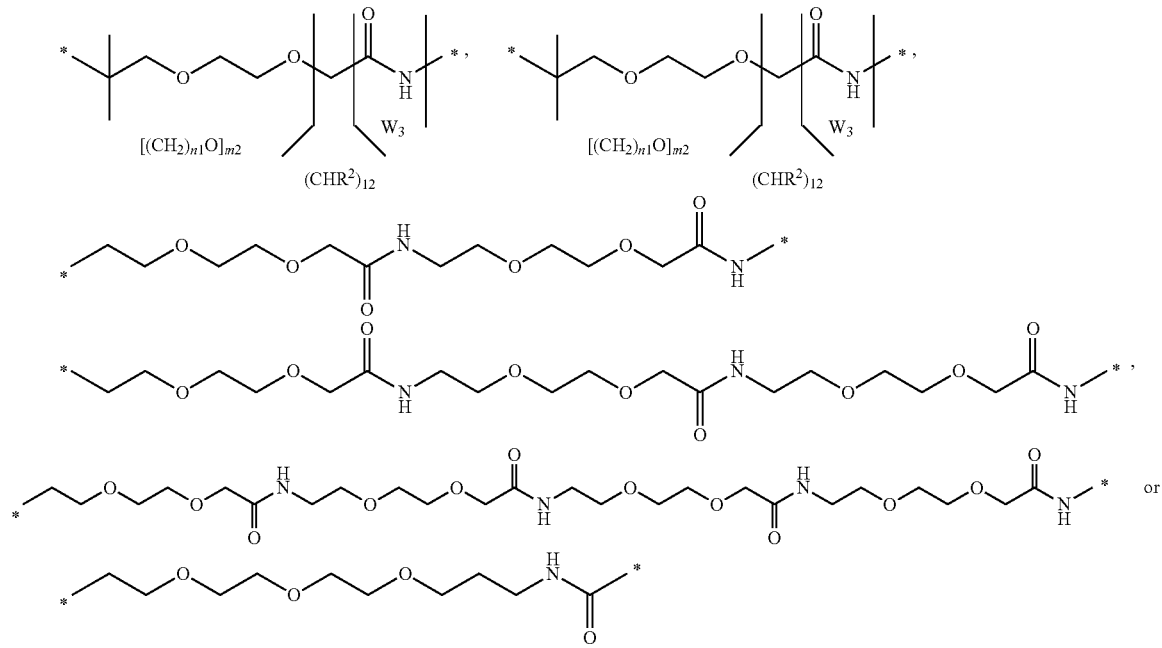

Embodiment 77

A protein conjugate as defined in any of Embodiments 51 to 76 wherein the hydrophilic spacer is selected from:

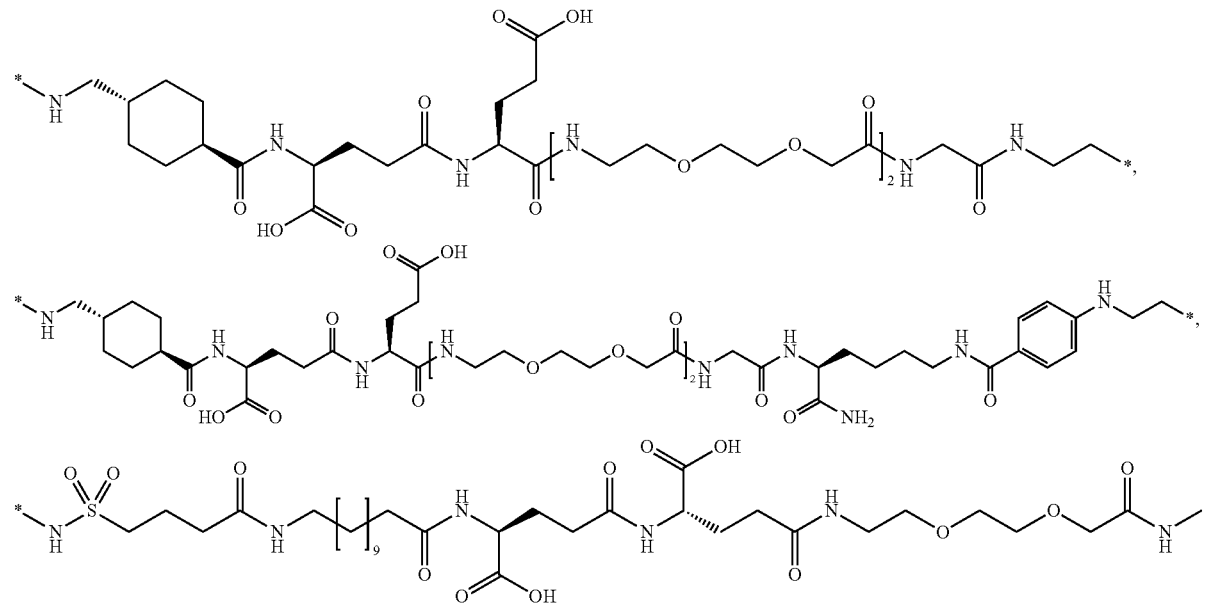

-continued
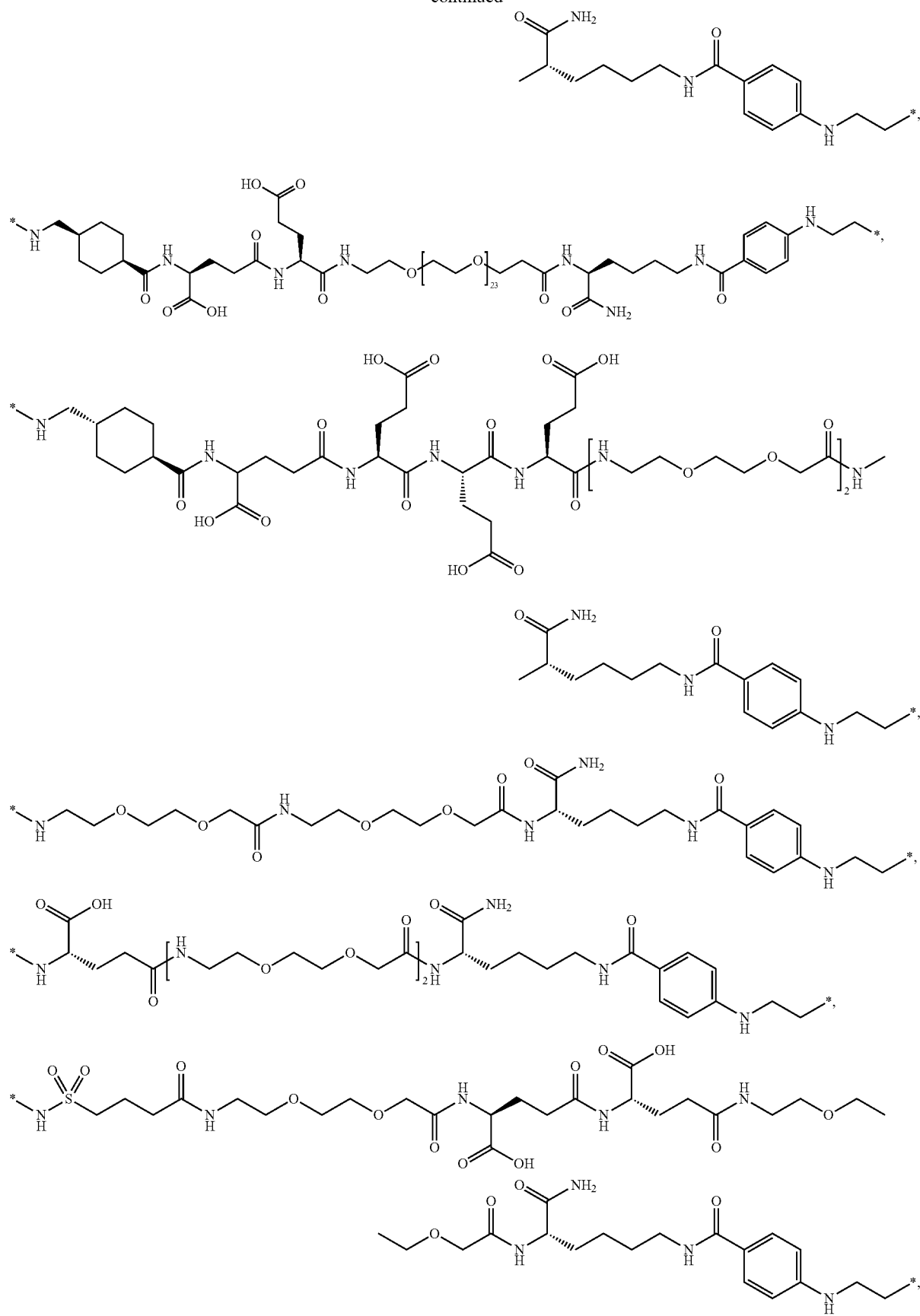

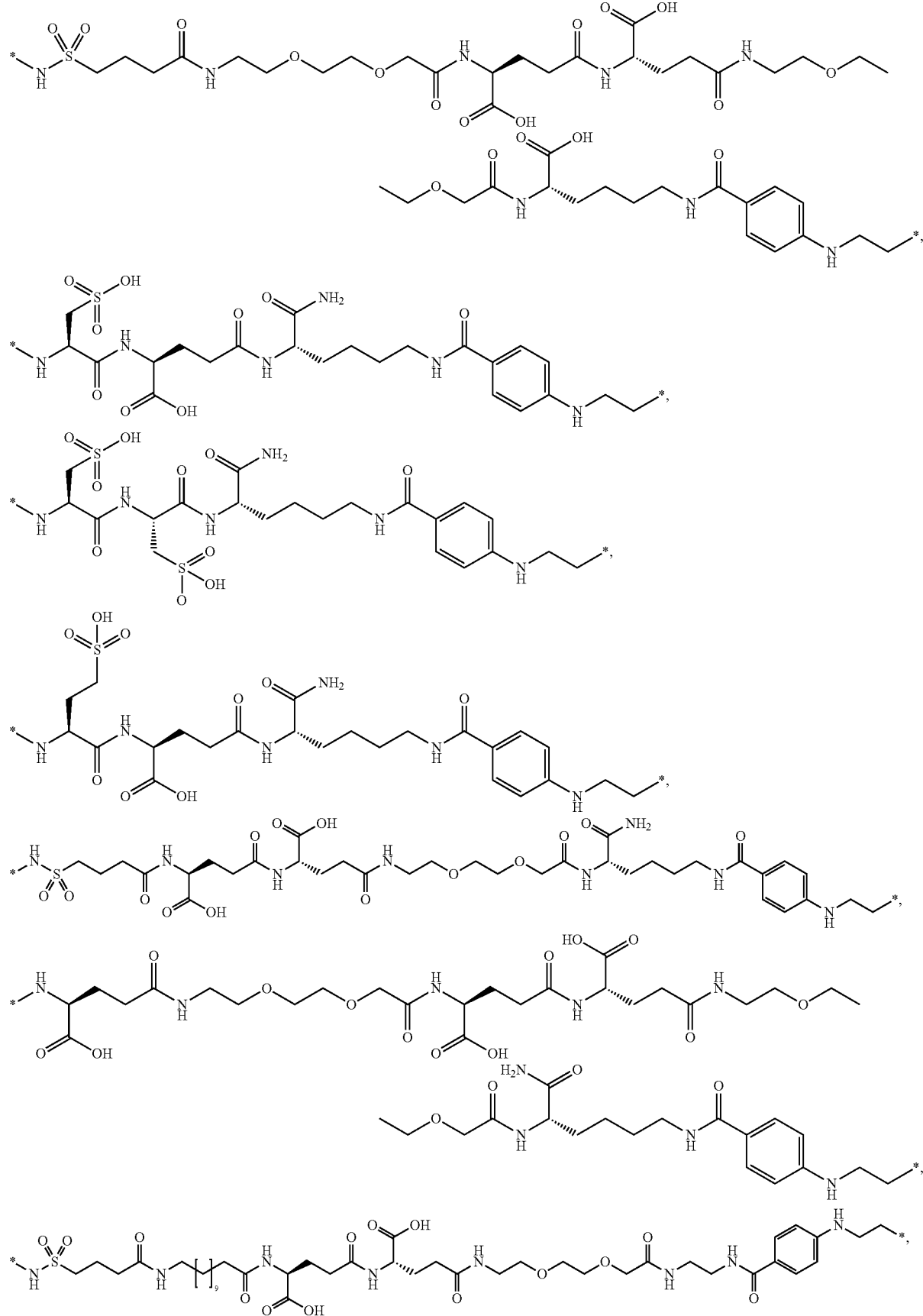

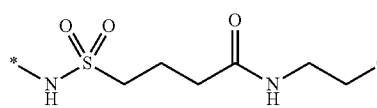
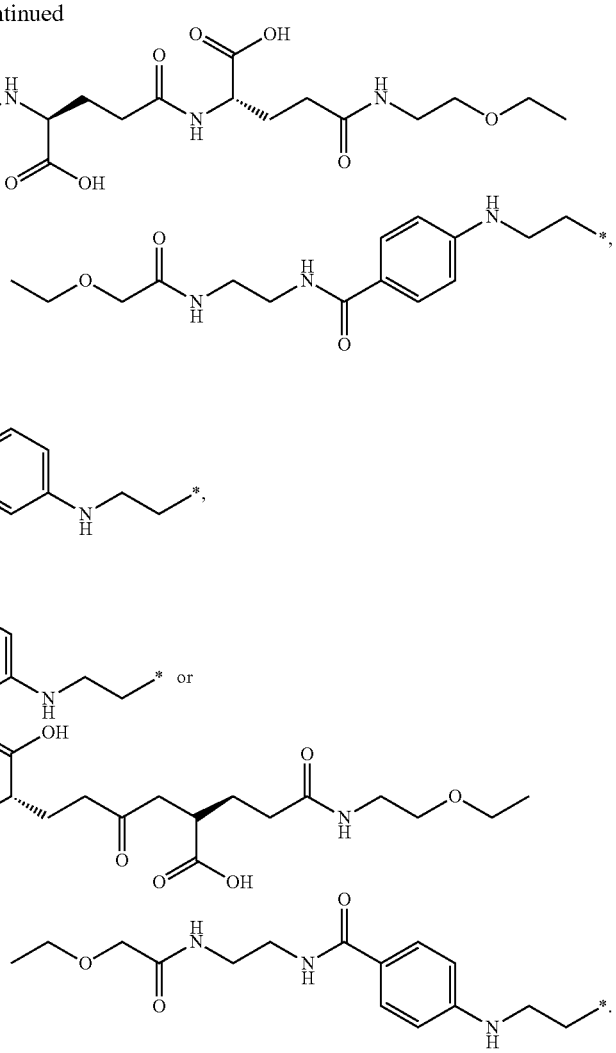

Embodiment 78

A protein conjugate as defined in any of Embodiments 51 to 77 wherein the molar weight of said hydrophilic spacer is in the range from 80 D to 1500 D or in the range from 500 D to 1100 D.

Embodiment 79

A protein conjugate as defined in any of Embodiments 51 to 78 wherein said albumin binding residue is a lipophilic residue.

Embodiment 80

A protein conjugate as defined in any of Embodiments 51 to 79 wherein said albumin binding residue binds non-covalently to albumin.

Embodiment 81

A protein conjugate as defined in any of Embodiments 51 to 80 wherein said albumin binding residue is negatively charged at physiological pH.

Embodiment 82

A protein conjugate as defined in any of Embodiments 51 to 81 wherein said albumin binding residue has a binding affinity towards human serum albumin that is below about 10 µM or below about 1 µM.

Embodiment 83

A protein conjugate as defined in any of Embodiments 51 to 82 wherein said albumin binding residue is selected from a straight chain alkyl group, a branched alkyl group, a group which has an ω-carboxylic acid group or an ω-carboxylic acid isoster.

Embodiment 84

A protein conjugate as defined in any of Embodiments 51 to 83 wherein said albumin binding residue has from 6 to 40 carbon atoms, from 8 to 26 carbon atoms or from 8 to 20 carbon atoms.

Embodiment 85

A protein conjugate as defined in any of Embodiments 51 to 84 wherein said albumin binding residue is a peptide, such as a peptide comprising less than 40 amino acid residues.

143

Embodiment 86

A protein conjugate as defined in any of Embodiments 51 to 85 wherein the albumin binder is selected from

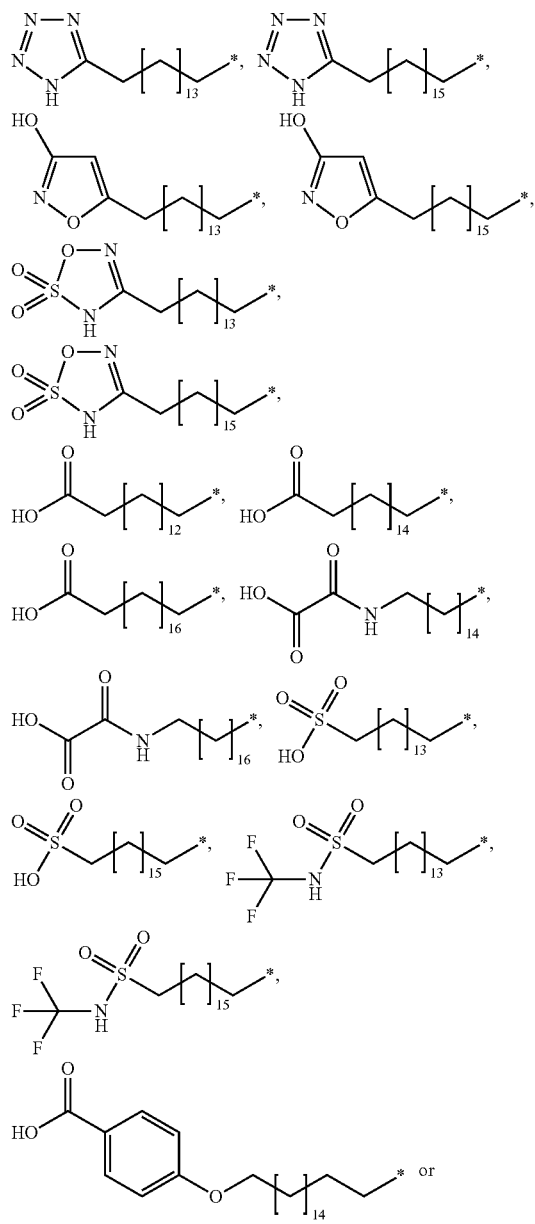

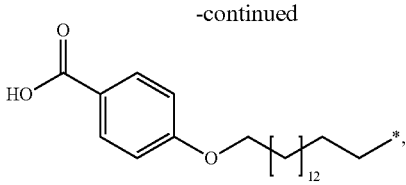

wherein * denotes the attachment to B through W.

Embodiment 87

A protein conjugate as defined in any of Embodiments 51 to 86, wherein the albumin binding residue A is attached to the glutamine residue of protein P via hydrophilic spacer B.

Embodiment 88

A protein conjugate as defined in any of Embodiments 51 to 86, wherein the albumin binding residue A is attached to a cystein residue of protein P via hydrophilic spacer B.

Embodiment 89

A protein conjugate as defined in any of Embodiments 51 to 86, wherein the albumin binding residue A is attached to the N-terminal residue of protein P via hydrophilic spacer B.

Embodiment 90

A protein conjugate as defined in any of Embodiments 51 to 86, wherein the albumin binding residue A is attached to the C-terminal residue of protein P via hydrophilic spacer B.

Embodiment 91

A protein conjugate as defined in any of Embodiments 51 to 86, wherein the albumin binding residue A is attached to a lysine residue of protein P via hydrophilic spacer B.

Embodiment 92

A protein conjugate as defined in any of Embodiments 51 to 86, wherein the albumin binding residue A is attached to an oxidized glycan residue of glycoprotein P via hydrophilic spacer B.

Embodiment 93

A protein conjugate as defined in any of Embodiments 51 to 92 wherein said conjugate is selected from

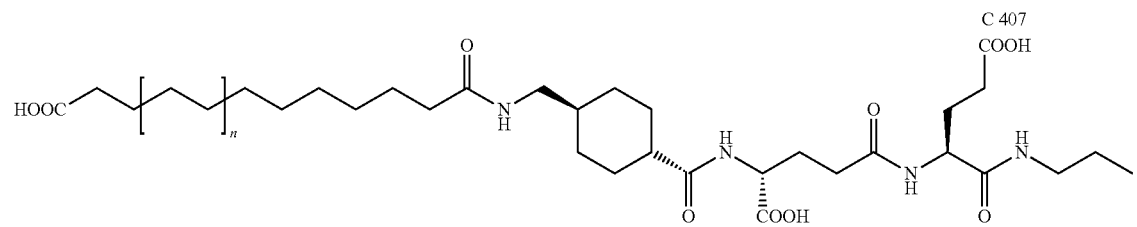

-continued
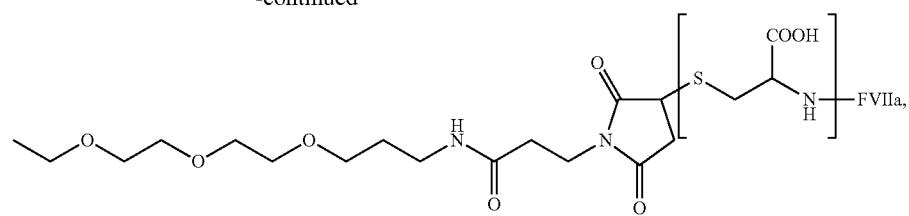
n = 5
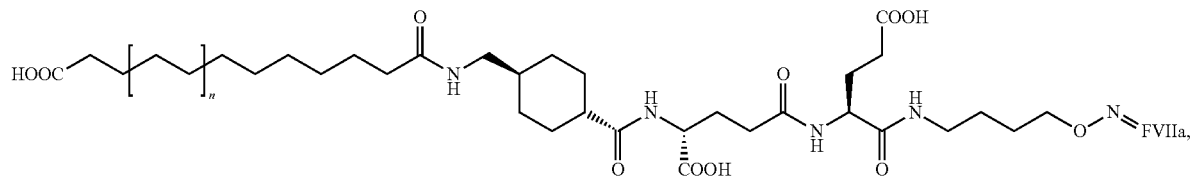
n = 5
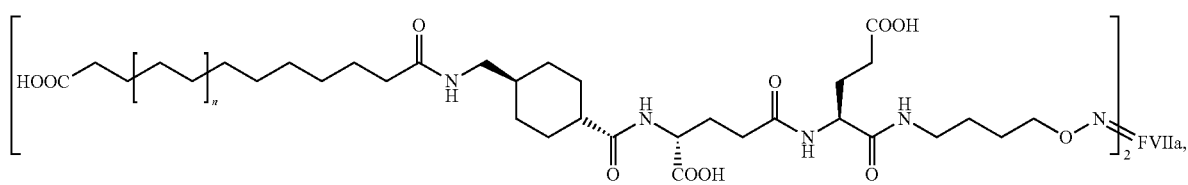
n = 5
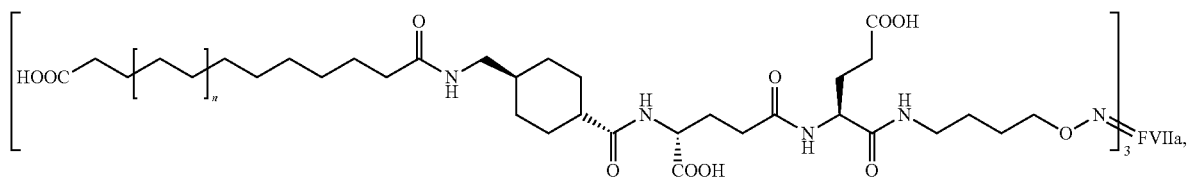
n = 5
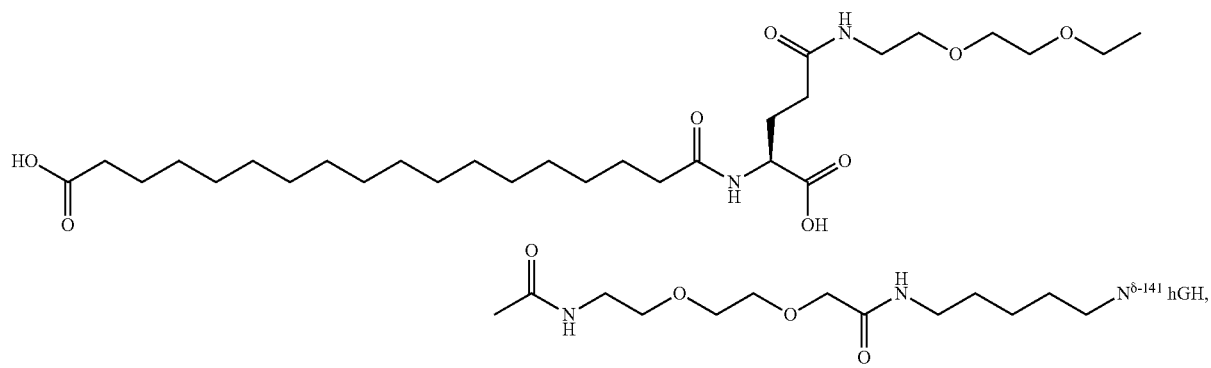
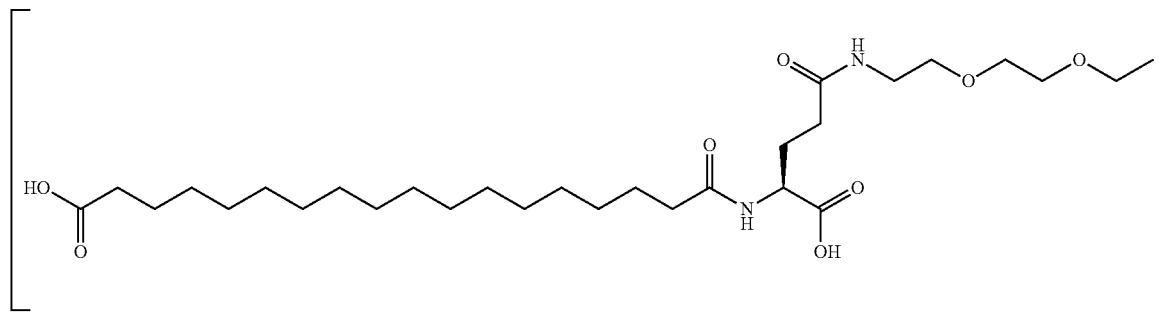

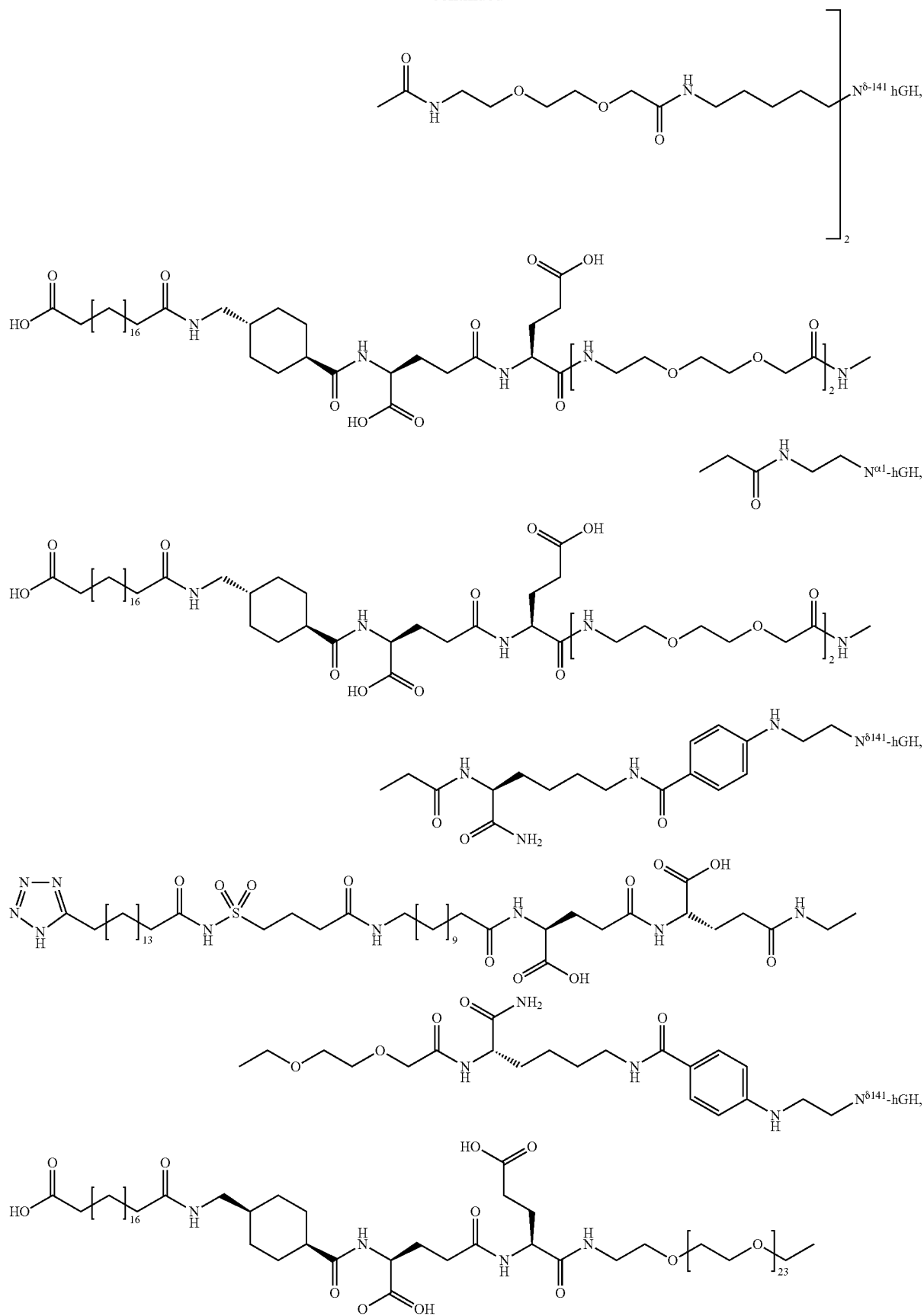

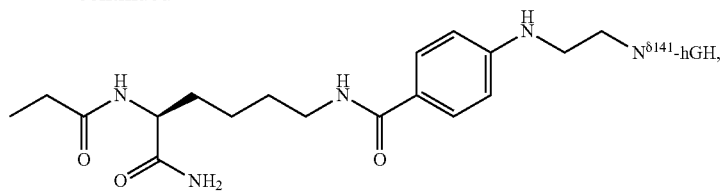
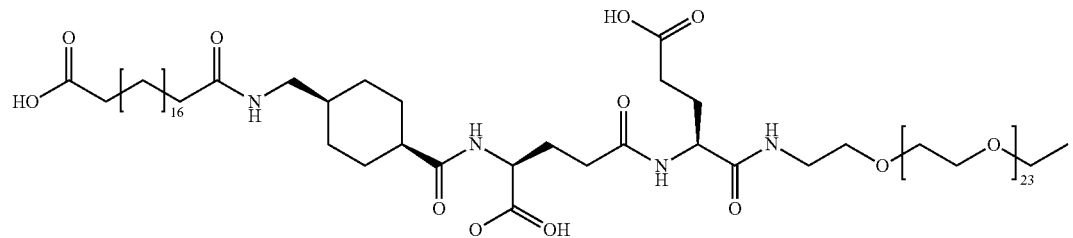
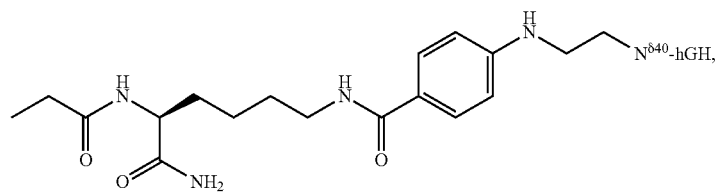
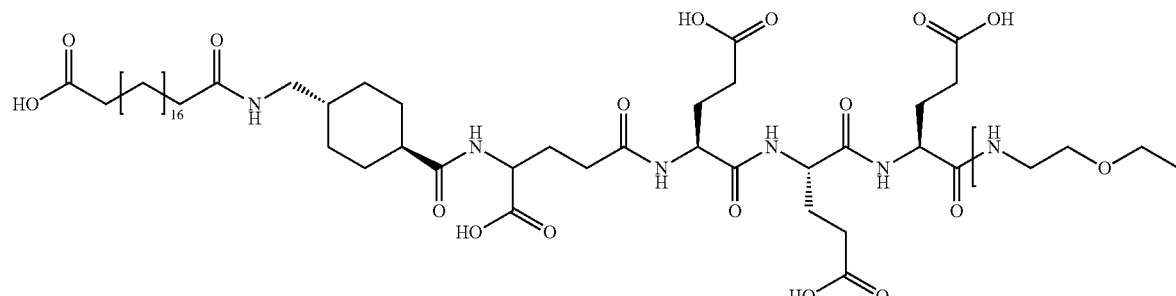
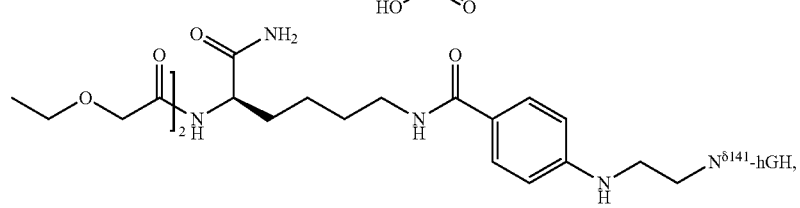
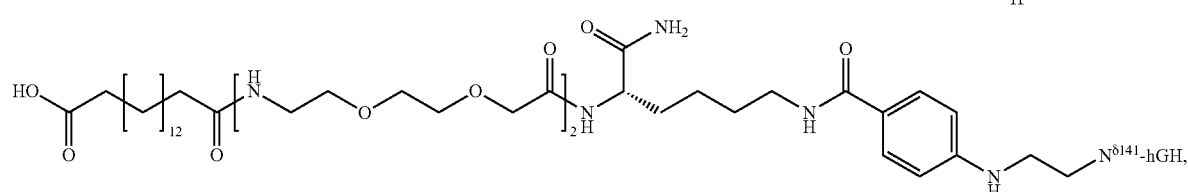
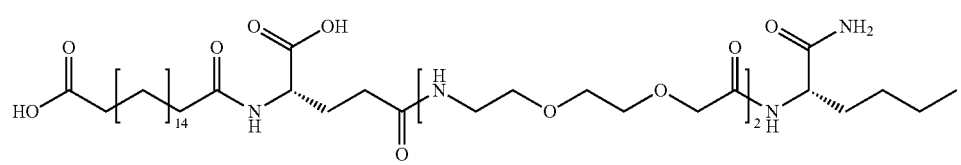
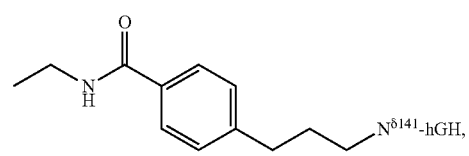

-continued
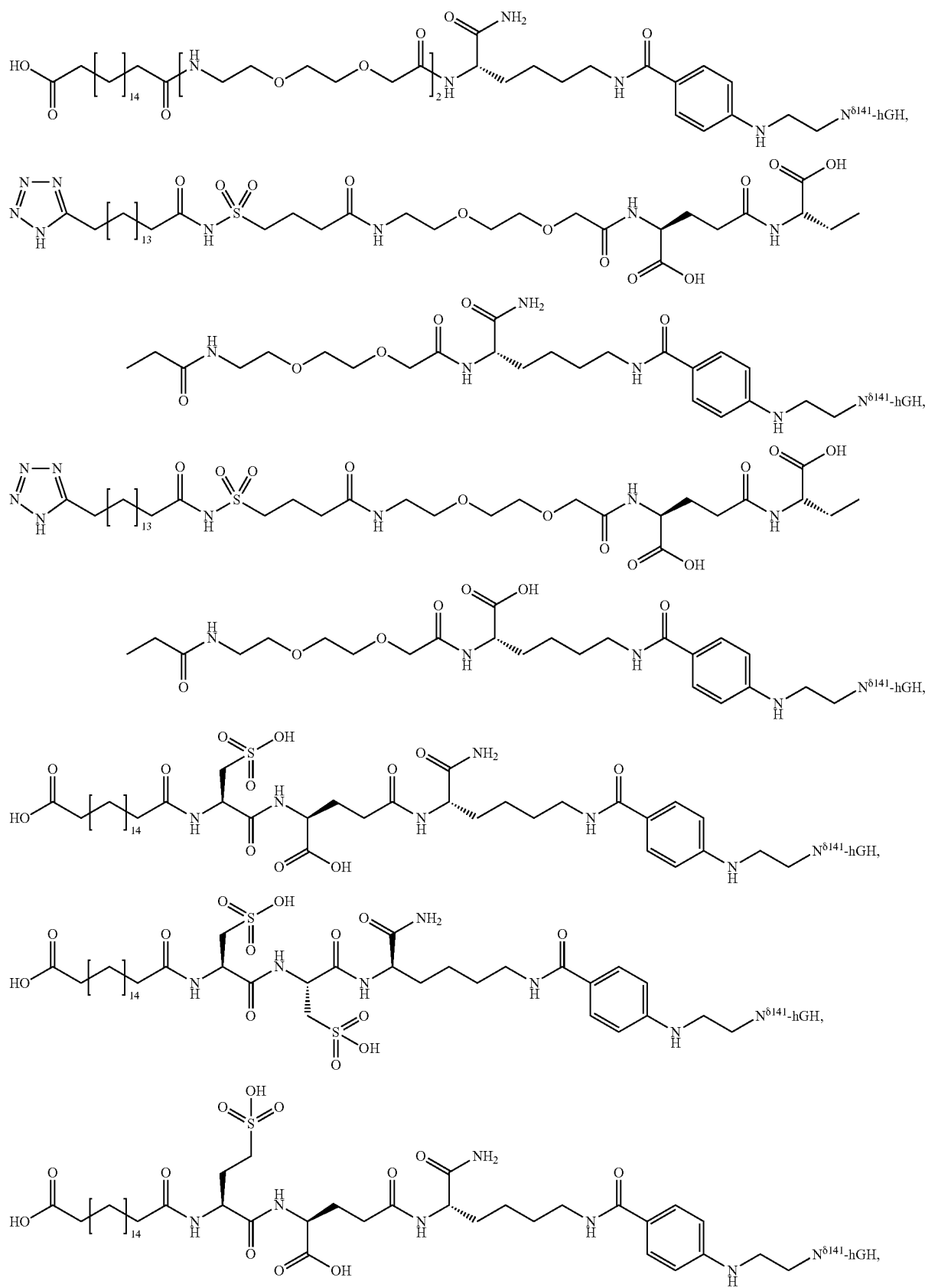

-continued
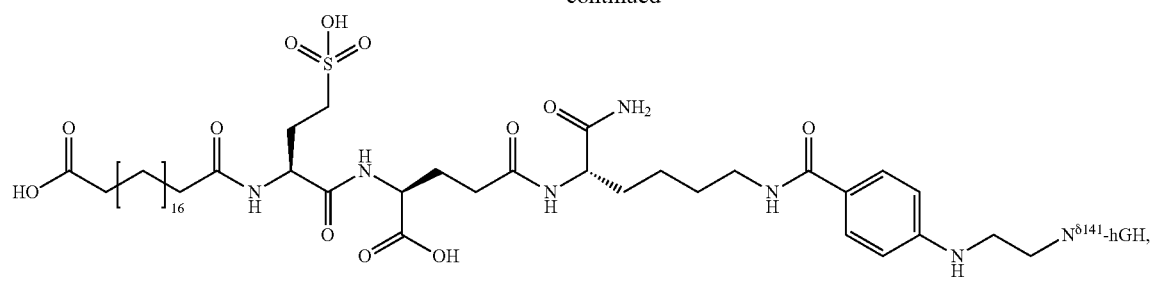
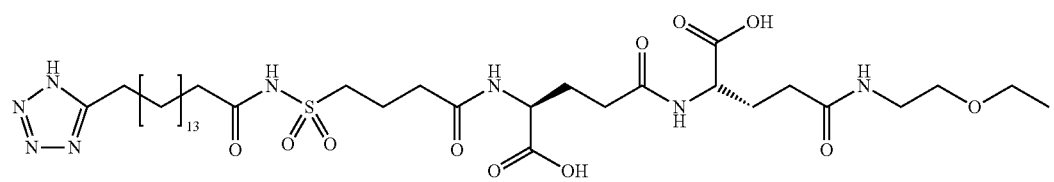
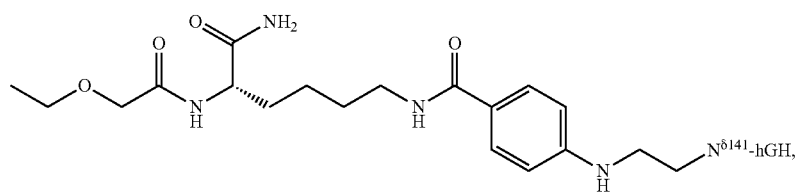
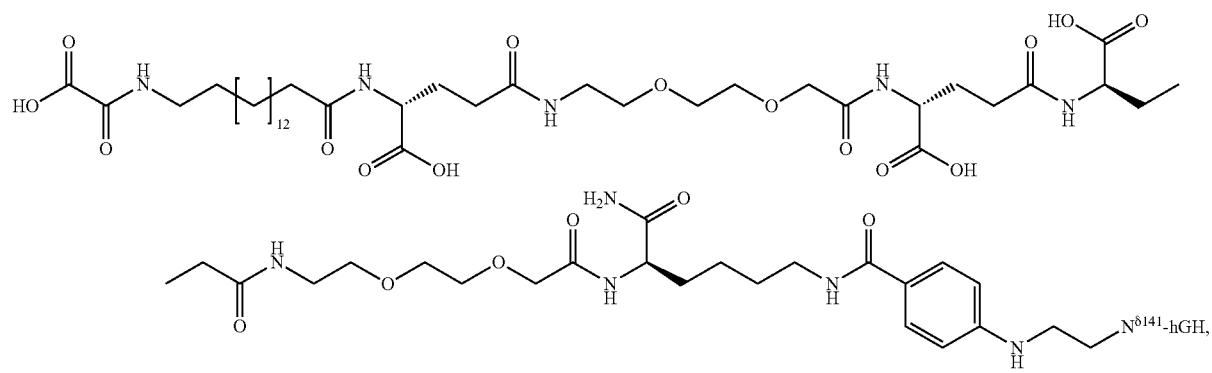
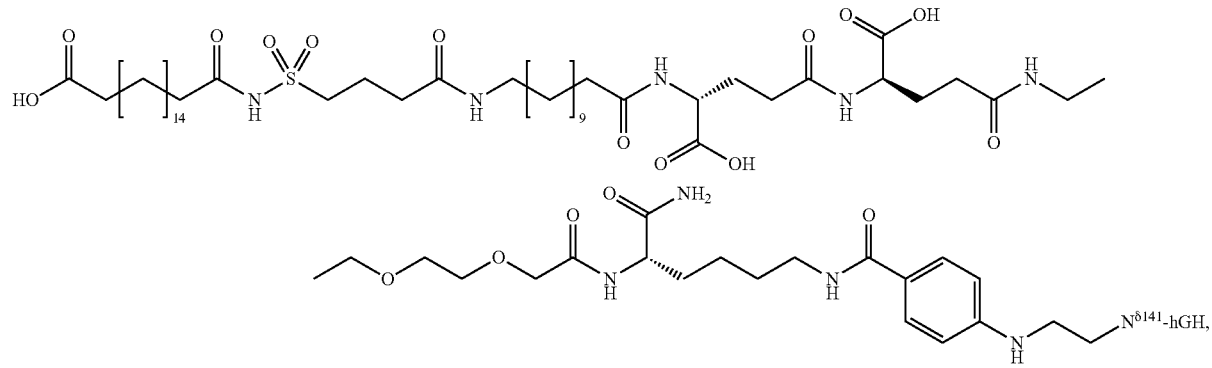
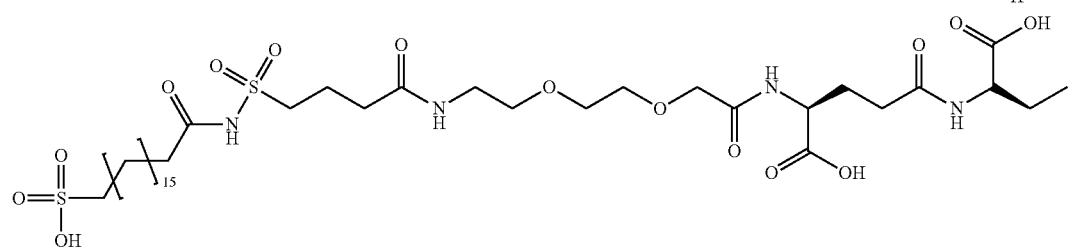

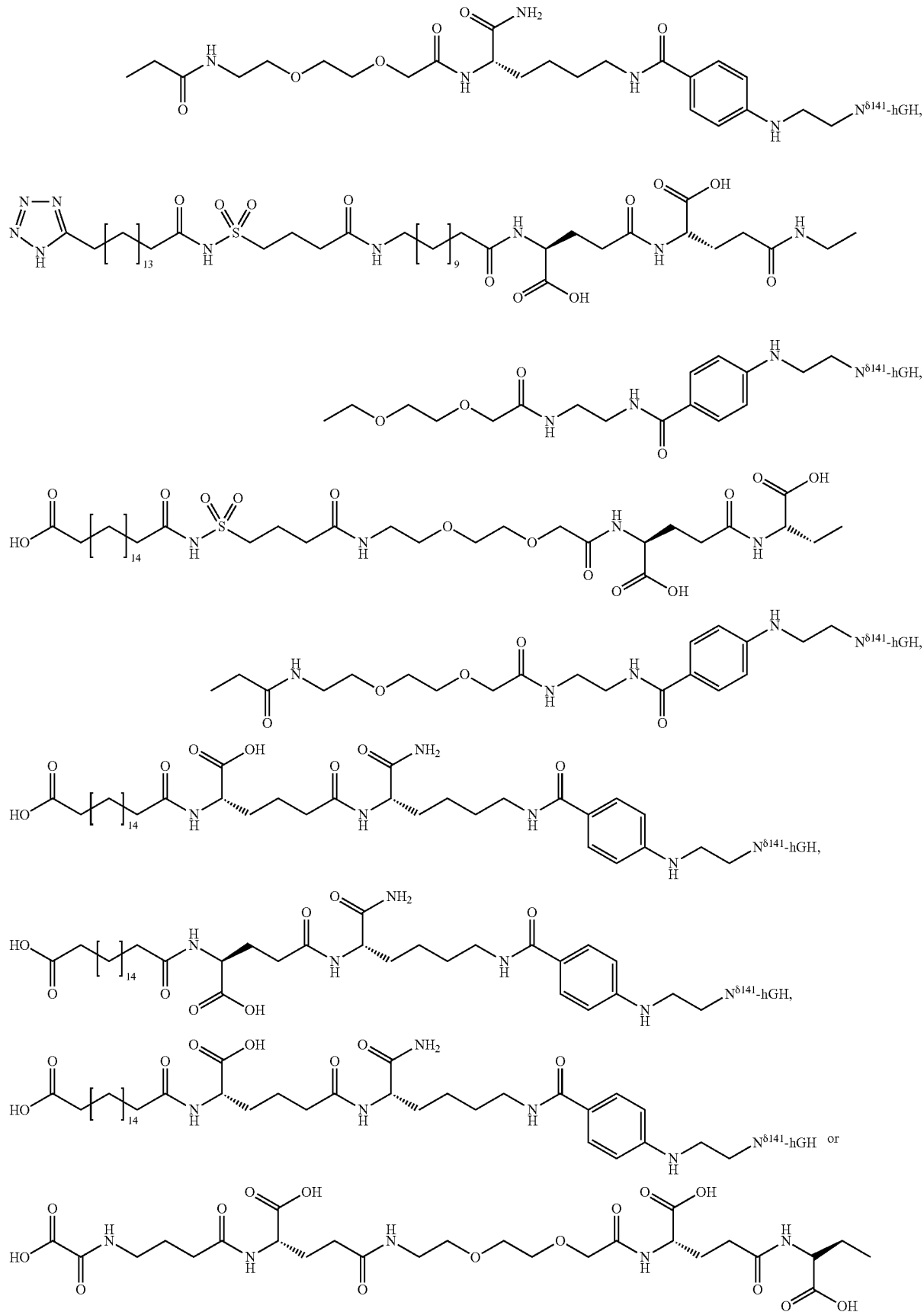

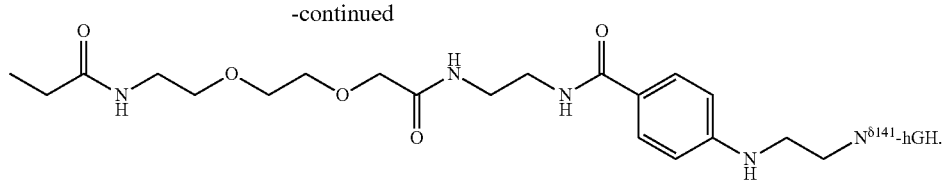

Embodiment 94

A protein conjugate as defined in any of Embodiments 50 to 93 for use in therapy.

Embodiment 95

A pharmaceutical composition comprising a protein conjugate as defined in any of Embodiments 50 to 93, optionally in combination with a pharmaceutical acceptable excipient.

Embodiment 96

A method of prophylactic treatment of hemophilia which comprises administering to a patient a therapeutically effective amount of a conjugated blood coagulation factor as defined in Embodiment 11.

Embodiment 97

A conjugated blood coagulation factor as defined in Embodiment 11 for use in the prophylactic treatment of hemophilia.

Embodiment 98

Use of a conjugated blood coagulation factor as defined in Embodiment 11 in the manufacture of a medicament for the prophylactic treatment of hemophilia.

Embodiment 99

A pharmaceutical composition comprising a conjugated blood coagulation factor as defined in Embodiment 11 for use in the prophylactic treatment of hemophilia.

Embodiment 100

A pharmaceutical formulation comprising a conjugated blood coagulation factor as defined in Embodiment 11.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention claimed is:

1. A process for preparing a conjugated blood coagulation factor which comprises the steps of reacting the blood coagulation factor with a water insoluble albumin binder in the presence of an optionally substituted cyclodextrin molecule, wherein said water insoluble albumin binder comprises a —$(CH_2)_{12}$— moiety.

2. The process of claim 1, wherein the cyclodextrin molecule comprises β-cyclodextrin, optionally substituted by one or more $C_{1-6}$ alkyl, each of which may be optionally substituted by one or more hydroxyl groups.

3. The process of claim 1, comprising reacting in an aqueous buffered solution.

4. The process of claim 1, wherein said blood coagulation factor is selected from the group consisting of FVII, FX, FII, FV, protein C, protein S, tPA, PAI-1, tissue factor, FXI, FXII, FXIII, FVIII sequence variants, and FIX sequence variants.

5. A blood coagulation factor conjugate selected from the group consisting of

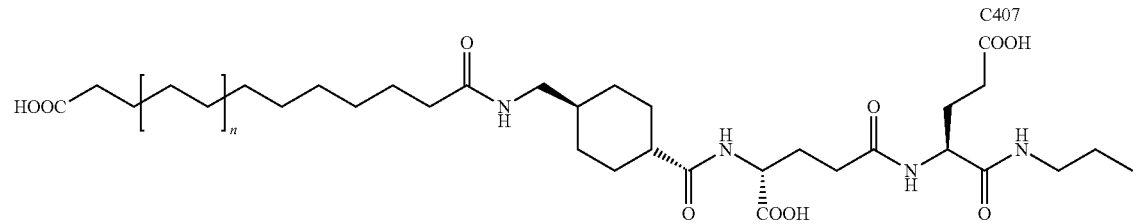

-continued
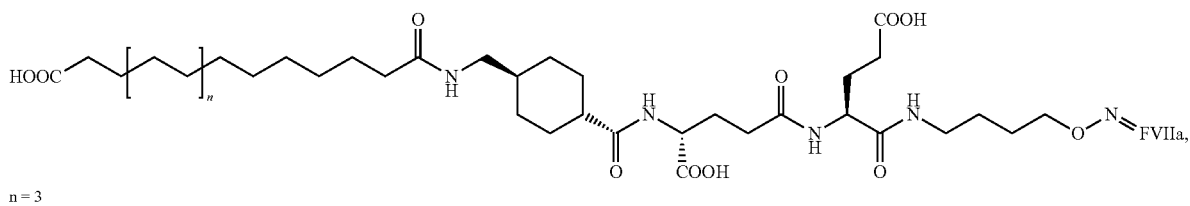
n = 3
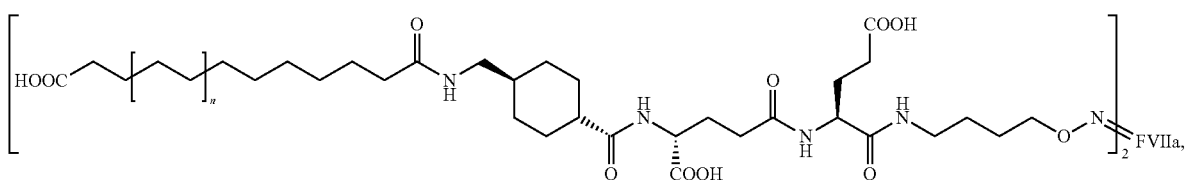
n = 3
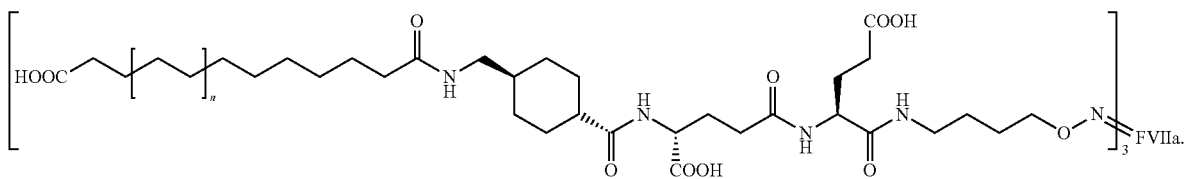
n = 3
and
n = 3
6. The process of claim 2, wherein the optionally substituted cyclodextrin is 2-hydroxyethyl-β-cyclodextrin.
7. The process of claim 3, wherein the aqueous buffered solution is a Hepes buffer.
8. The process of claim 7, wherein the Hepes buffer comprises 50 mM Hepes, 100 mM NaCl and 10 mM $CaCl_2$.
9. The process of claim 4, wherein said coagulation factor is FVII.
* * * * *